(12) United States Patent
Dettling et al.

(10) Patent No.: US 12,202,910 B2
(45) Date of Patent: Jan. 21, 2025

(54) ANTIBODIES SPECIFIC FOR FLT3 AND THEIR USES

(71) Applicant: PFIZER INC., New York, NY (US)

(72) Inventors: Danielle Elizabeth Dettling, San Francisco, CA (US); Yik Andy Yeung, South San Francisco, CA (US); Kristian Todd Poulsen, San Francisco, CA (US); Veena Krishnamoorthy, Burlingame, CA (US); Cesar Adolfo Sommer, San Mateo, CA (US)

(73) Assignee: PFIZER INC., South San Francisco, CA (US)

( * ) Notice: Subject to any disclaimer, the term of this patent is extended or adjusted under 35 U.S.C. 154(b) by 363 days.

(21) Appl. No.: 17/849,467

(22) Filed: Jun. 24, 2022

(65) Prior Publication Data

US 2023/0059489 A1   Feb. 23, 2023

Related U.S. Application Data

(62) Division of application No. 15/993,874, filed on May 31, 2018, now Pat. No. 11,421,040.

(60) Provisional application No. 62/660,908, filed on Apr. 20, 2018, provisional application No. 62/514,574, filed on Jun. 2, 2017.

(51) Int. Cl.
| | |
|---|---|
| *C07H 21/04* | (2006.01) |
| *A61P 35/00* | (2006.01) |
| *A61P 35/02* | (2006.01) |
| *C07K 16/28* | (2006.01) |
| *C07K 16/46* | (2006.01) |
| *A61K 39/00* | (2006.01) |

(52) U.S. Cl.
CPC ............ *C07K 16/461* (2013.01); *A61P 35/00* (2018.01); *A61P 35/02* (2018.01); *C07K 16/2809* (2013.01); *C07K 16/2863* (2013.01); *A61K 2039/505* (2013.01); *C07K 2317/21* (2013.01); *C07K 2317/31* (2013.01); *C07K 2317/33* (2013.01); *C07K 2317/52* (2013.01); *C07K 2317/62* (2013.01); *C07K 2317/71* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,635,388 A | 6/1997 | Bennett | |
| 7,125,659 B1 | 10/2006 | Kiyoi | |
| 8,921,528 B2 | 12/2014 | Holt et al. | |
| 9,023,996 B2 * | 5/2015 | Grosse-Hovest | .. C07K 16/2896 435/328 |
| 11,421,040 B2 | 8/2022 | Dettling et al. | |
| 2006/0128788 A1 | 12/2006 | Baumann | |
| 2006/0281755 A1 | 12/2006 | Baumann | |
| 2006/0281771 A1 | 12/2006 | Baumann | |
| 2007/0149572 A1 | 6/2007 | Ballentine | |
| 2007/0225306 A1 | 9/2007 | Choi | |
| 2008/0213251 A1 | 9/2008 | Sexton | |
| 2009/0054358 A1 | 2/2009 | Small | |
| 2009/0169562 A1 | 7/2009 | Throsby | |
| 2009/0297529 A1 | 12/2009 | Li et al. | |
| 2009/0311183 A1 | 12/2009 | Devy | |
| 2010/0278834 A1 | 11/2010 | Lanzavecchia | |
| 2011/0142851 A1 | 6/2011 | Misher | |
| 2011/0152173 A1 | 6/2011 | Lofquist | |
| 2011/0200611 A1 | 8/2011 | Sexton | |
| 2011/0268739 A1 | 11/2011 | Throsby | |
| 2011/0275094 A1 | 11/2011 | Gunawardane | |
| 2012/0328612 A1 | 12/2012 | Grosse-Hovest | |
| 2013/0052205 A1 | 2/2013 | Valmier | |
| 2013/0156764 A1 | 6/2013 | Levis | |
| 2013/0171148 A1 | 7/2013 | De Goeij | |
| 2013/0177572 A1 | 7/2013 | Chen | |
| 2013/0288373 A1 | 10/2013 | Verstraete | |
| 2014/0170149 A1 | 6/2014 | Neijssen | |
| 2014/0245490 A1 | 8/2014 | Crawford | |
| 2015/0104479 A1 | 4/2015 | Romano et al. | |
| 2015/0110819 A1 | 4/2015 | Sette | |

(Continued)

FOREIGN PATENT DOCUMENTS

| | | |
|---|---|---|
| AU | 2018275359 B2 | 7/2021 |
| CN | 104288765 A | 1/2015 |

(Continued)

OTHER PUBLICATIONS

Abu-Duhier et al., "FLT3 Internal Tandem Duplication Mutations in Adult Acute Myeloid Leukemia Define a High-Risk Group," Br J Haematol. 111 (1):190-195 (Oct. 2000).

(Continued)

*Primary Examiner* — Meera Natarajan
(74) *Attorney, Agent, or Firm* — Mintz Levin Cohn Ferris Glovsky and Popeo, P.C.

(57) ABSTRACT

The present invention provides antibodies that specifically bind to FLT3 (Fms-Like Tyrosine Kinase 3). The invention further provides bispecific antibodies that bind to FLT3 and another antigen (e.g., CD3). The invention further relates to antibody encoding nucleic acids, and methods of obtaining such antibodies (monospecific and bispecific). The invention further relates to therapeutic methods for use of these antibodies for the treatment of FLT3-mediated pathologies, including cancer such as Acute Myeloid Leukemia (AML).

8 Claims, 7 Drawing Sheets

Specification includes a Sequence Listing.

(56) References Cited

U.S. PATENT DOCUMENTS

| | | |
|---|---|---|
| 2015/0307615 A1 | 10/2015 | Panousis |
| 2016/0244750 A1 | 8/2016 | Vasquez |
| 2016/0272716 A1 | 9/2016 | Lowe |
| 2016/0297884 A1 | 10/2016 | Kuo et al. |
| 2016/0297885 A1 | 10/2016 | Kuo et al. |
| 2016/0297888 A1 | 10/2016 | Zhou et al. |
| 2016/0311903 A1 | 10/2016 | West |
| 2016/0362472 A1 | 12/2016 | Bitter |
| 2017/0037149 A1 | 2/2017 | Raum |
| 2017/0088620 A1 | 3/2017 | Nioi |
| 2017/0129961 A1 | 5/2017 | Raum |
| 2018/0346601 A1 | 12/2018 | Dettling et al. |

FOREIGN PATENT DOCUMENTS

| | | |
|---|---|---|
| EA | 12622 B1 | 10/2009 |
| EP | 3029067 A1 | 6/2016 |
| JP | A-2011-521647 | 7/2011 |
| JP | 2017513478 A | 6/2017 |
| WO | WO-2003/074059 A2 | 9/2003 |
| WO | WO-2005/110392 A1 | 11/2005 |
| WO | WO 2009/155015 A1 | 12/2009 |
| WO | WO 2011/076922 A1 | 6/2011 |
| WO | WO-2012/094115 A1 | 7/2012 |
| WO | WO-2013/040142 A2 | 3/2013 |
| WO | WO 2013/092001 A1 | 6/2013 |
| WO | WO 2013/174832 A1 | 11/2013 |
| WO | 2014011988 A2 | 1/2014 |
| WO | 2016012021 A1 | 1/2016 |
| WO | WO 2016/016859 A1 | 2/2016 |
| WO | WO 2016/145099 A1 | 9/2016 |
| WO | WO-2016/164637 A1 | 10/2016 |
| WO | WO 2017/021362 A1 | 2/2017 |
| WO | WO 2017/053889 A2 | 3/2017 |
| WO | 2018220584 A1 | 12/2018 |
| WO | WO 2018/222935 A1 | 12/2018 |

OTHER PUBLICATIONS

Almagro & Fransson, "Humanization of antibodies," Frontiers in Bioscience 2008; 13:1619-33 (Year: 2008).

Birg et al., "Expression of the FMS/KIT-Like Gene FL T3 in Human Acute Leukemias of the Myeloid and Lymphoid Lineages," Blood: 80(10): 2584-2593 (Nov. 1992).

Carow et al., "Expression of the Hematopoietic Growth Factor Receptor FL T3 (STK-1/Flk2) in Human Leukemias," Blood: 87(3): 1089-1096 (Feb. 1996).

Communication pursuant to Rules 161(1) and 162 EPC for European Patent Application 18734624.2, dated Jan. 16, 2020. 3 pages.

Human Translation of KR Office Action for KR Application No. 2022-7002509, 6 pgs.

JP Office Action for JP Application No. 2019-565897, Jun. 1, 2022, 3 pgs.

KR Office Action for KR Application No. 2022-7002509, dated Apr. 1, 2022, 7 pgs.

Translation of JP Office Action for JP Application No. 2019-565897, 3 pgs.

De Genst et al., "Antibody repertoire development in camelids," Dev Comp Immunol 2006; 30: 187-98 (Year: 2006).

Diamond et al., "Somatic mutation of the T15 heavy chain gives rise to an antibody with autoantibody specificity", Proc. Natl. Acad. Sci. USA, 1984, vol. 81, p. 5841-5844.

Durben et al., "Characterization of a Bispecific FLT3 X CD3 Antibody in an Improved, Recombinant Format for the Treatment of Leukemia," Molecular Therapy, vol. 23, p. 648-655 (2015).

Hofmann et al., "Generation, Selection and Preclinical Characterization of an Fc-Optimized FLT3 Antibody for the Treatment of Myeloid Leukemia", Leukemia, XP055041249, 26(6): 1228-1237, Published Online Jan. 6, 2012.

International Search Report for International Appln. No. PCT/IB2018/053908 completed Sep. 3, 2018. 8 pages.

Ohno et al., "Antigen-binding specificities of antibodies are primarily determined by seven residues of VH", Proc. Natl. Acad. Sci. USA, 1985, vol. 82, pp. 2945-2949, abstract.

Rudikoff et al., "Single amino acid substitution altering antigen-binding specificity", Proc. Nat. Acad. Sci. USA. Immunology. (1982) 79: p. 1979-1983, abstract.

Written Opinion of the International Searching Authority for International Appln. No. PCT/IB2018/053908 completed Sep. 3, 2018. 10 pages.

Yamamoto et al., "Activating Mutation of D835 within the Activation Loop of FL T3 in Human Hematologic Malignancies," Blood: 97(8): 2434-2439 (Apr. 2001).

Yoshinaga et al., "Ig L-chain Shuffling for Affinity Maturation of Phage Library-derived Human Anti-human MCP-1 Antibody Blocking its Chemotactic Activity," J. Biochem 2008; 143:593-601 (Year: 2008).

Fontanelli et al., "Sorafenib as Monotherapy or in Association With Cytarabine and Clofarabine for the Treatment of Relapsed/Refractory FLT3 ITD-Positive Advanced Acute Myeloid Leukemia" Clinical Lymphoma Myeloma and Leukemia, vol. 14, No. 1, Feb. 2014, pp. e13-e17 (5 pages).

Kadia et al., "New drugs in acute myeloid leukemia", Annals of Oncology, vol. 27, No. 5, pp. 770-778 (9 pages) May 2016.

Li et al., "FLT3 Antibody-Based Therapeutics for Leukemia Therapy" International Journal of Hematology, vol. 82, No. 2, 2005, pp. 108-114 (7 pages).

Li et al. "Suppression of leukemia expressing wild-type or ITD-mutant FLT3 receptor by a fully human anti-FLT3 neutralizing antibody", Blood, vol. 104, No. 4, Aug. 15, 2004, pp. 1137-1144 (8 pages).

Piloto et al., "IMC-EB10, an Anti-FLT3 Monoclonal Antibody, Prolongs Survival and Reduces Nonobese Diabetic/Severe Combined Immunodeficient Engraftment of Some Acute Lymphoblastic Leukemia Cell Lines and Primary Leukemic Samples", Cancer Research, vol. 66, No. 9, May 1, 2006, pp. 4843-4851 (9 pages).

Sherbenou et al., "The development of potential antibody-based therapies for myeloma", Blood Reviews, vol. 29, No. 2, Mar. 2015, pp. 81-91.

Small et al., "Targeting FLT3 for the Treatment of Leukemia", Seminars in Hematology, vol. 45, No. 2, Jul. 2008, pp. S17-S21, DOI: 10.1053/j.seminhematol.2008.07.007 (5 pages).

Yamamoto et al., "Isolation of human mAbs that directly modulate FMS-related tyrosine kinase 3 signaling", Cancer Science, vol. 103, No. 2, Feb. 2012, pp. 350-359, DOI: 10.1111/j.1349-7006.2011.02141.x (10 pages).

Youssoufian et al., "Targeting FMS-Related Tyrosine Kinase Receptor 3 With the Human Immunoglobulin G1 Monoclonal Antibody IMC-EB10", Cancer, vol. 116, No. 4 Supp, Feb. 15, 2010, pp. 1013-1017 (5 pages).

Chen et al. (May 12, 2017) "Targeting FLT3 by Chimeric Antigen Receptor T Cells for the Treatment of Acute Myeloid Leukemia", Leukemia, 31:1830-1834.

Chien et al. (Dec. 2, 2016) "Preclinical Development of FLT3-Redirected Chimeric Antigen Receptor T Cell Immunotherapy for Acute Myeloid Leukemia", Blood, 128(22):1072.

Philip et al. (Aug. 21, 2014) "A Highly Compact Epitope-Based Marker/Suicide Gene for Easier and Safer T-cell Therapy", Blood, 124(8):1277-1287.

* cited by examiner

SEQUENCE LISTING

```
<160> NUMBER OF SEQ ID NOS: 293

<210> SEQ ID NO 1
<211> LENGTH: 108
<212> TYPE: PRT
<213> ORGANISM: Artificial Sequence
<220> FEATURE:
<223> OTHER INFORMATION: Synthetic Construct

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ala Ser His Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Pro Pro
                85                  90                  95

Arg Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: Synthetic Construct

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Thr Val Thr Tyr Ala Gln Lys Phe
    50                  55                  60

Gln Gly Arg Val Thr Ile Thr Ala Asp Glu Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Trp Ser Gly Ala Thr Gly Ala Ser Asp Thr Trp Gly
            100                 105                 110

Gln Gly Thr Leu Val Thr Val Ser Ser
            115                 120
```

<210> SEQ ID NO 3
<211> LENGTH: 107
<212> TYPE: PRT
<213> ORGANISM: Artificial Sequence
<220> FEATURE:
<223> OTHER INFORMATION: Synthetic Construct

<400> SEQUENCE: 3

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Tyr Val Ser Ala Ser
            20                  25                  30

Leu Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Arg Ser Ser
                85                  90                  95

Thr Phe Gly Gln Gly Thr Lys Val Glu Ile Lys
            100                 105
```

<210> SEQ ID NO 4
<211> LENGTH: 120
<212> TYPE: PRT
<213> ORGANISM: Artificial Sequence
<220> FEATURE:
<223> OTHER INFORMATION: Synthetic Construct

<400> SEQUENCE: 4

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Gly Ile Ile Pro Ala Phe Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Gly Ser Tyr Ser Leu Asp Tyr Phe Asp Ile Trp Gly Gln
            100                 105                 110

Gly Thr Leu Val Thr Val Ser Ser
        115                 120
```

<210> SEQ ID NO 5
<211> LENGTH: 107
<212> TYPE: PRT
<213> ORGANISM: Artificial Sequence
<220> FEATURE:
<223> OTHER INFORMATION: Synthetic Construct

<400> SEQUENCE: 5

```
Asp Ile Gln Met Thr Gln Ser Pro Ser Ser Leu Ser Ala Ser Val Gly
1               5                   10                  15
```

-continued

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 6
<211> LENGTH: 119
<212> TYPE: PRT
<213> ORGANISM: Artificial Sequence
<220> FEATURE:
<223> OTHER INFORMATION: Synthetic Construct

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Asp Ile Ser Trp Val Arg Gln Ala Pro Gly Gln Gly Leu Glu Trp Met
        35                  40                  45

Gly Gly Ile Ile Pro Val Ser Gly Arg Ala Asn Tyr Ala Gln Lys Phe
    50                  55                  60

Gln Gly Arg Val Thr Ile Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Arg Pro Thr Tyr Trp Pro Leu Asp Tyr Trp Gly Gln Gly
            100                 105                 110

Thr Leu Val Thr Val Ser Ser
        115

<210> SEQ ID NO 7
<211> LENGTH: 110
<212> TYPE: PRT
<213> ORGANISM: Artificial Sequence
<220> FEATURE:
<223> OTHER INFORMATION: Synthetic Construct

<400> SEQUENCE: 7

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

```
Asn Thr Val Val Phe Gly Gly Gly Thr Lys Leu Thr Val Leu
            100                 105                 110
```

<210> SEQ ID NO 8
<211> LENGTH: 125
<212> TYPE: PRT
<213> ORGANISM: Artificial Sequence
<220> FEATURE:
<223> OTHER INFORMATION: Synthetic Construct

<400> SEQUENCE: 8

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Tyr Ile Gly Trp Val Arg Gln Ala Pro Gly Gln Gly Leu Glu Trp Met
        35                  40                  45

Gly Gly Ile Ile Pro Trp Phe Gly Thr Ala Asn Tyr Ala Gln Lys Phe
    50                  55                  60

Gln Gly Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ala Asp His His Asp Ser Pro Ser Gly Tyr Thr Ser Gly Gly Phe
            100                 105                 110

Asp Val Trp Gly Gln Gly Thr Leu Val Thr Val Ser Ser
        115                 120                 125
```

<210> SEQ ID NO 9
<211> LENGTH: 110
<212> TYPE: PRT
<213> ORGANISM: Artificial Sequence
<220> FEATURE:
<223> OTHER INFORMATION: Synthetic Construct

<400> SEQUENCE: 9

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu
            100                 105                 110
```

<210> SEQ ID NO 10
<211> LENGTH: 123
<212> TYPE: PRT
<213> ORGANISM: Artificial Sequence
<220> FEATURE:
<223> OTHER INFORMATION: Synthetic Construct

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ala Ser Tyr
            20                  25                  30

Ala Met Ser Trp Val Arg Gln Ala Pro Gly Lys Gly Leu Glu Trp Val
        35                  40                  45

Ser Glu Ile Ser Ser Ser Gly Gly Ser Thr Thr Tyr Ala Asp Ser Val
    50              55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Met Ala Gly Leu Gly Tyr Asp Pro Phe Asp Tyr
            100                 105                 110

Trp Gly Gln Gly Thr Leu Val Thr Val Ser Ser
            115                 120
```

<210> SEQ ID NO 11
<211> LENGTH: 110
<212> TYPE: PRT
<213> ORGANISM: Artificial Sequence
<220> FEATURE:
<223> OTHER INFORMATION: Synthetic Construct

<400> SEQUENCE: 11

```
Gln Ser Val Leu Thr Gln Pro Pro Ser Ala Ser Gly Thr Pro Gly Gln
1               5                   10                  15

Arg Val Thr Ile Ser Cys Ser Gly Ser Gly Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50              55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Gly Ser Leu
                85                  90                  95

Ser Arg Pro Val Phe Gly Thr Gly Thr Lys Leu Thr Val Leu
            100                 105                 110
```

<210> SEQ ID NO 12
<211> LENGTH: 123
<212> TYPE: PRT
<213> ORGANISM: Artificial Sequence
<220> FEATURE:
<223> OTHER INFORMATION: Synthetic Construct

<400> SEQUENCE: 12

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Ser Phe
            20                  25                  30

Ala Met Ser Trp Val Arg Gln Ala Pro Gly Lys Gly Leu Glu Trp Val
        35                  40                  45

Ser Asp Ile Ser Gly Ser Gly Ala Ser Thr Tyr Tyr Ala Asp Ser Val
    50              55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Ser Ala Ser Gly Ser Gly Ser Tyr Trp Pro Tyr Met Asp Pro
            100                 105                 110

Trp Gly Gln Gly Thr Leu Val Thr Val Ser Ser
        115                 120
```

<210> SEQ ID NO 13
<211> LENGTH: 108
<212> TYPE: PRT
<213> ORGANISM: Artificial Sequence
<220> FEATURE:
<223> OTHER INFORMATION: Synthetic Construct

<400> SEQUENCE: 13

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Pro Asn Glu
            20                  25                  30

Gln Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Pro Pro
                85                  90                  95

Leu Thr Phe Gly Gln Gly Thr Lys Val Glu Ile Lys
            100                 105
```

<210> SEQ ID NO 14
<211> LENGTH: 117
<212> TYPE: PRT
<213> ORGANISM: Artificial Sequence
<220> FEATURE:
<223> OTHER INFORMATION: Synthetic Construct

<400> SEQUENCE: 14

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Val Phe Ser Arg Tyr
            20                  25                  30

Ala Leu Ser Trp Val Arg Gln Ala Pro Gly Gln Gly Leu Glu Trp Met
        35                  40                  45

Gly Gly Ile Ile Pro Met Leu Gly Phe Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Leu Asp Phe Gly Ala Leu Asp Tyr Trp Gly Gln Gly Thr Leu
            100                 105                 110

Val Thr Val Ser Ser
        115
```

<210> SEQ ID NO 15
<211> LENGTH: 108
<212> TYPE: PRT

<213> ORGANISM: Artificial Sequence
<220> FEATURE:
<223> OTHER INFORMATION: Synthetic Construct

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Glu Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Ser Ser Pro
                85                  90                  95

Leu Thr Phe Gly Gln Gly Thr Lys Val Glu Ile Lys
            100                 105

<210> SEQ ID NO 16
<211> LENGTH: 122
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ser Phe
            20                  25                  30

Asp Ile Ser Trp Val Arg Gln Ala Pro Gly Gln Gly Leu Glu Trp Met
        35                  40                  45

Gly Arg Ile Ile Pro Ile Leu Gly Tyr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Asp Leu Gly Ala Pro Ala Gly Tyr Pro Phe Asp Pro Trp
            100                 105                 110

Gly Gln Gly Thr Leu Val Thr Val Ser Ser
        115                 120

<210> SEQ ID NO 17
<211> LENGTH: 107
<212> TYPE: PRT
<213> ORGANISM: Artificial Sequence
<220> FEATURE:
<223> OTHER INFORMATION: Synthetic Construct

<400> SEQUENCE: 17

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

```
Tyr Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Thr Ala Trp
                 85                  90                  95

Val Phe Gly Gly Gly Thr Lys Leu Thr Val Leu
             100                 105
```

<210> SEQ ID NO 18
<211> LENGTH: 121
<212> TYPE: PRT
<213> ORGANISM: Artificial Sequence
<220> FEATURE:
<223> OTHER INFORMATION: Synthetic Construct

<400> SEQUENCE: 18

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Thr Arg Trp Trp Trp Gly Asp Ala Phe Asp His Trp Gly
            100                 105                 110

Gln Gly Thr Leu Val Thr Val Ser Ser
            115                 120
```

<210> SEQ ID NO 19
<211> LENGTH: 108
<212> TYPE: PRT
<213> ORGANISM: Artificial Sequence
<220> FEATURE:
<223> OTHER INFORMATION: Synthetic Construct

<400> SEQUENCE: 19

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Pro Ser Ser
                 20                  25                  30

Gln Leu Ala Trp Tyr Gln Gln Lys Pro Gly Gln Ala Pro Arg Leu Leu
             35                  40                  45

Ile Tyr Asp Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gln Gly Thr Lys Val Glu Ile Lys
            100                 105
```

```
<210> SEQ ID NO 20
<211> LENGTH: 117
<212> TYPE: PRT
<213> ORGANISM: Artificial Sequence
<220> FEATURE:
<223> OTHER INFORMATION: Synthetic Construct

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Gln Trp Val Arg Gln Ala Pro Gly Gln Gly Leu Glu Trp Met
        35                  40                  45

Gly Gly Ile Val Gly Ser Trp Gly Leu Ala Asn Tyr Ala Gln Lys Phe
    50                  55                  60

Gln Gly Arg Val Thr Ile Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Ser Ala Phe Gly Glu Leu Ala Ser Trp Gly Gln Gly Thr Leu
            100                 105                 110

Val Thr Val Ser Ser
        115

<210> SEQ ID NO 21
<211> LENGTH: 108
<212> TYPE: PRT
<213> ORGANISM: Artificial Sequence
<220> FEATURE:
<223> OTHER INFORMATION: Synthetic Construct

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ala Val Asp Ser Ser
            20                  25                  30

Asp Leu Ala Trp Tyr Gln Lys Pro Gly Gln Ala Pro Arg Leu Leu
        35                  40                  45

Ile Tyr Asp Ala Tyr Thr Arg Pro Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Leu Glu Ile Lys
            100                 105

<210> SEQ ID NO 22
<211> LENGTH: 117
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Val Phe Ser Arg Tyr
            20                  25                  30
```

Ala Leu Ser Trp Val Arg Gln Ala Pro Gly Gln Gly Leu Glu Trp Met
        35                  40                  45

Gly Gly Ile Ile Pro Met Leu Gly Phe Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Leu Asp Phe Gly Ala Leu Asp Tyr Trp Gly Gln Gly Thr Leu
            100                 105                 110

Val Thr Val Ser Ser
            115

<210> SEQ ID NO 23
<211> LENGTH: 107
<212> TYPE: PRT
<213> ORGANISM: Artificial Sequence
<220> FEATURE:
<223> OTHER INFORMATION: Synthetic Construct

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Thr Phe Thr Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Thr Phe Gly Gln Gly Thr Arg Leu Glu Ile Lys
            100                 105

<210> SEQ ID NO 24
<211> LENGTH: 124
<212> TYPE: PRT
<213> ORGANISM: Artificial Sequence
<220> FEATURE:
<223> OTHER INFORMATION: Synthetic Construct

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp

```
                 100                 105                 110

Ile Trp Gly Gln Gly Thr Leu Val Thr Val Ser Ser
        115                 120

<210> SEQ ID NO 25
<211> LENGTH: 107
<212> TYPE: PRT
<213> ORGANISM: Artificial Sequence
<220> FEATURE:
<223> OTHER INFORMATION: Synthetic Construct

<400> SEQUENCE: 25

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Thr
            20                  25                  30

Tyr Leu Ala Trp Tyr Gln Gln Lys Pro Gly Gln Ala Pro Arg Leu Leu
        35                  40                  45

Ile Tyr Asp Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gln Gly Thr Lys Val Glu Ile Lys
            100                 105

<210> SEQ ID NO 26
<211> LENGTH: 124
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120

<210> SEQ ID NO 27
<211> LENGTH: 107
<212> TYPE: PRT
<213> ORGANISM: Artificial Sequence
<220> FEATURE:
<223> OTHER INFORMATION: Synthetic Construct

<400> SEQUENCE: 27
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Leu
                85                  90                  95

Thr Phe Gly Gln Gly Thr Lys Val Glu Ile Lys
            100                 105

<210> SEQ ID NO 28
<211> LENGTH: 116
<212> TYPE: PRT
<213> ORGANISM: Artificial Sequence
<220> FEATURE:
<223> OTHER INFORMATION: Synthetic Construct

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Glu Trp Val
        35                  40                  45

Ser Val Ile Ser Gly Ser Gly Thr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Ile Trp Asp Leu Arg Tyr Trp Gly Gln Gly Thr Leu Val
            100                 105                 110

Thr Val Ser Ser
        115

<210> SEQ ID NO 29
<211> LENGTH: 108
<212> TYPE: PRT
<213> ORGANISM: Artificial Sequence
<220> FEATURE:
<223> OTHER INFORMATION: Synthetic Construct

<400> SEQUENCE: 29

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ile Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Ser Gly Ile Pro Asp Arg Phe Ser
50                  55                  60

Gly Ser Gly Ser Gly Thr Asp Phe Thr Leu Thr Ile Ser Arg Leu Glu

```
                65                  70                  75                  80
Pro Glu Asp Phe Ala Val Tyr Tyr Cys Gln Gln Tyr Gly Gly Ser Pro
                    85                  90                  95

Tyr Thr Phe Gly Gln Gly Thr Lys Val Glu Ile Lys
                100                 105
```

<210> SEQ ID NO 30
<211> LENGTH: 120
<212> TYPE: PRT
<213> ORGANISM: Artificial Sequence
<220> FEATURE:
<223> OTHER INFORMATION: Synthetic Construct

<400> SEQUENCE: 30

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Met Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Thr Leu Ile Tyr Pro Ile Pro Phe Glu Leu Trp Gly Gln
                100                 105                 110

Gly Thr Leu Val Thr Val Ser Ser
        115                 120
```

<210> SEQ ID NO 31
<211> LENGTH: 108
<212> TYPE: PRT
<213> ORGANISM: Artificial Sequence
<220> FEATURE:
<223> OTHER INFORMATION: Synthetic Construct

<400> SEQUENCE: 31

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser His Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Phe Arg Ala Ala Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Asp Pro
                85                  90                  95

Tyr Thr Phe Gly Gln Gly Thr Lys Val Glu Ile Lys
                100                 105
```

<210> SEQ ID NO 32
<211> LENGTH: 123
<212> TYPE: PRT
<213> ORGANISM: Artificial Sequence
<220> FEATURE:

<223> OTHER INFORMATION: Synthetic Construct

<400> SEQUENCE: 32

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Val Ser Trp Val Arg Gln Ala Pro Gly Gln Gly Leu Glu Trp Met
        35                  40                  45

Gly Gly Ile Ile Pro Ile Phe Gly Ile Ala Asn Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Glu Gly Ile Gly Gly Asp Leu Arg Tyr Asp Gly Tyr Asp Ala
            100                 105                 110

Trp Gly Gln Gly Thr Leu Val Thr Val Ser Ser
        115                 120
```

<210> SEQ ID NO 33
<211> LENGTH: 107
<212> TYPE: PRT
<213> ORGANISM: Artificial Sequence
<220> FEATURE:
<223> OTHER INFORMATION: Synthetic Construct

<400> SEQUENCE: 33

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Asp Ala Ser Asp Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Trp
                85                  90                  95

Thr Phe Gly Gln Gly Thr Lys Val Glu Ile Lys
            100                 105
```

<210> SEQ ID NO 34
<211> LENGTH: 116
<212> TYPE: PRT
<213> ORGANISM: Artificial Sequence
<220> FEATURE:
<223> OTHER INFORMATION: Synthetic Construct

<400> SEQUENCE: 34

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Val Met Asn Trp Val Arg Gln Ala Pro Gly Lys Gly Leu Glu Trp Val
        35                  40                  45

Ser Ala Ile Ser Gly Ser Gly Ala Thr Thr Tyr Tyr Ala Asp Ser Val
```

```
                  50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Val Ser Gly Leu Trp Ala Gly Gly Ile Trp Gly Gln Gly Thr Leu Val
                    100                 105                 110

Thr Val Ser Ser
            115
```

<210> SEQ ID NO 35
<211> LENGTH: 110
<212> TYPE: PRT
<213> ORGANISM: Artificial Sequence
<220> FEATURE:
<223> OTHER INFORMATION: Synthetic Construct

<400> SEQUENCE: 35

```
Asn Phe Met Leu Thr Gln Pro His Ser Val Ser Glu Ser Pro Gly Lys
  1               5                  10                  15

Thr Val Thr Ile Ser Cys Thr Arg Ser Ser Gly Ser Ile Ala Ser Asn
                 20                  25                  30

Tyr Val Gln Trp Tyr Gln Gln Lys Pro Gly Gln Ala Pro Val Leu Val
             35                  40                  45

Val Tyr Asp Asp Ser Asp Arg Pro Ser Gly Ile Pro Glu Arg Phe Ser
 50                  55                  60

Gly Ser Asn Ser Gly Asn Thr Ala Thr Leu Thr Ile Ser Arg Val Glu
 65                  70                  75                  80

Ala Gly Asp Glu Ala Asp Tyr Tyr Cys Gln Val Trp Asp Ser Ser Ser
                     85                  90                  95

Asp His Trp Val Phe Gly Gly Gly Thr Lys Leu Thr Val Leu
                    100                 105                 110
```

<210> SEQ ID NO 36
<211> LENGTH: 124
<212> TYPE: PRT
<213> ORGANISM: Artificial Sequence
<220> FEATURE:
<223> OTHER INFORMATION: Synthetic Construct

<400> SEQUENCE: 36

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Gly Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Met Tyr Tyr Cys
                     85                  90                  95

Ala Arg Asp Tyr Tyr Ala Phe Ser Asp Pro Ala Tyr Gly Gly Met Asp
                    100                 105                 110

Val Trp Gly Gln Gly Thr Leu Val Thr Val Ser Ser
            115                 120
```

<210> SEQ ID NO 37
<211> LENGTH: 5
<212> TYPE: PRT
<213> ORGANISM: Artificial Sequence
<220> FEATURE:
<223> OTHER INFORMATION: Synthetic Construct

<400> SEQUENCE: 37

Ser Tyr Gly Ile Ser
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic Construct

<400> SEQUENCE: 38

Gly Gly Thr Phe Gly Ser Tyr
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic Construct

<400> SEQUENCE: 39

Gly Gly Thr Phe Gly Ser Tyr Gly Ile Ser
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Synthetic Construct

<400> SEQUENCE: 40

Gly Ile Ile Pro Ile Phe Gly Thr Val Thr Tyr Ala Gln Lys Phe Gln
1               5                   10                  15

Gly

<210> SEQ ID NO 41
<211> LENGTH: 6
<212> TYPE: PRT
<213> ORGANISM: Artificial Sequence
<220> FEATURE:
<223> OTHER INFORMATION: Synthetic Construct

<400> SEQUENCE: 41

Ile Pro Ile Phe Gly Thr
1               5

<210> SEQ ID NO 42
<211> LENGTH: 12
<212> TYPE: PRT
<213> ORGANISM: Artificial Sequence
<220> FEATURE:
<223> OTHER INFORMATION: Synthetic Construct

<400> SEQUENCE: 42

Asp Ser Trp Ser Gly Ala Thr Gly Ala Ser Asp Thr
1               5                   10

<210> SEQ ID NO 43
<211> LENGTH: 5
<212> TYPE: PRT
<213> ORGANISM: Artificial Sequence
<220> FEATURE:
<223> OTHER INFORMATION: Synthetic Construct

<400> SEQUENCE: 43

Ser Tyr Thr Ile Ser
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic Construct

<400> SEQUENCE: 44

Gly Gly Thr Phe Ser Ser Tyr
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic Construct

<400> SEQUENCE: 45

Gly Gly Thr Phe Ser Ser Tyr Thr Ile Ser
1               5                   10

<210> SEQ ID NO 46
<211> LENGTH: 17
<212> TYPE: PRT
<213> ORGANISM: Artificial Sequence
<220> FEATURE:
<223> OTHER INFORMATION: Synthetic Construct

<400> SEQUENCE: 46

Gly Ile Ile Pro Ala Phe Gly Ile Ala Asn Tyr Ala Gln Lys Phe Gln
1               5                   10                  15

Gly

<210> SEQ ID NO 47
<211> LENGTH: 6
<212> TYPE: PRT
<213> ORGANISM: Artificial Sequence
<220> FEATURE:
<223> OTHER INFORMATION: Synthetic Construct

<400> SEQUENCE: 47

Ile Pro Ala Phe Gly Ile
1               5

<210> SEQ ID NO 48
<211> LENGTH: 11
<212> TYPE: PRT
<213> ORGANISM: Artificial Sequence
<220> FEATURE:
<223> OTHER INFORMATION: Synthetic Construct

<400> SEQUENCE: 48

Gly Gly Ser Tyr Ser Leu Asp Tyr Phe Asp Ile

```
1               5                   10
```

<210> SEQ ID NO 49
<211> LENGTH: 5
<212> TYPE: PRT
<213> ORGANISM: Artificial Sequence
<220> FEATURE:
<223> OTHER INFORMATION: Synthetic Construct

<400> SEQUENCE: 49

```
Ser Tyr Asp Ile Ser
1               5
```

<210> SEQ ID NO 50
<211> LENGTH: 10
<212> TYPE: PRT
<213> ORGANISM: Artificial Sequence
<220> FEATURE:
<223> OTHER INFORMATION: Synthetic Construct

<400> SEQUENCE: 50

```
Gly Gly Thr Phe Ser Ser Tyr Asp Ile Ser
1               5                   10
```

<210> SEQ ID NO 51
<211> LENGTH: 17
<212> TYPE: PRT
<213> ORGANISM: Artificial Sequence
<220> FEATURE:
<223> OTHER INFORMATION: Synthetic Construct

<400> SEQUENCE: 51

```
Gly Ile Ile Pro Val Ser Gly Arg Ala Asn Tyr Ala Gln Lys Phe Gln
1               5                   10                  15

Gly
```

<210> SEQ ID NO 52
<211> LENGTH: 6
<212> TYPE: PRT
<213> ORGANISM: Artificial Sequence
<220> FEATURE:
<223> OTHER INFORMATION: Synthetic Construct

<400> SEQUENCE: 52

```
Ile Pro Val Ser Gly Arg
1               5
```

<210> SEQ ID NO 53
<211> LENGTH: 10
<212> TYPE: PRT
<213> ORGANISM: Artificial Sequence
<220> FEATURE:
<223> OTHER INFORMATION: Synthetic Construct

<400> SEQUENCE: 53

```
Val Arg Pro Thr Tyr Trp Pro Leu Asp Tyr
1               5                   10
```

<210> SEQ ID NO 54
<211> LENGTH: 5
<212> TYPE: PRT
<213> ORGANISM: Artificial Sequence
<220> FEATURE:
<223> OTHER INFORMATION: Synthetic Construct

<400> SEQUENCE: 54

Ser Tyr Tyr Ile Gly
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic Construct

<400> SEQUENCE: 55

Gly Gly Thr Phe Ser Ser Tyr
1               5

<210> SEQ ID NO 56
<211> LENGTH: 10
<212> TYPE: PRT
<213> ORGANISM: Artificial Sequence
<220> FEATURE:
<223> OTHER INFORMATION: Synthetic Construct

<400> SEQUENCE: 56

Gly Gly Thr Phe Ser Ser Tyr Tyr Ile Gly
1               5                   10

<210> SEQ ID NO 57
<211> LENGTH: 17
<212> TYPE: PRT
<213> ORGANISM: Artificial Sequence
<220> FEATURE:
<223> OTHER INFORMATION: Synthetic Construct

<400> SEQUENCE: 57

Gly Ile Ile Pro Trp Phe Gly Thr Ala Asn Tyr Ala Gln Lys Phe Gln
1               5                   10                  15

Gly

<210> SEQ ID NO 58
<211> LENGTH: 6
<212> TYPE: PRT
<213> ORGANISM: Artificial Sequence
<220> FEATURE:
<223> OTHER INFORMATION: Synthetic Construct

<400> SEQUENCE: 58

Ile Pro Trp Phe Gly Thr
1               5

<210> SEQ ID NO 59
<211> LENGTH: 16
<212> TYPE: PRT
<213> ORGANISM: Artificial Sequence
<220> FEATURE:
<223> OTHER INFORMATION: Synthetic Construct

<400> SEQUENCE: 59

Asp His His Asp Ser Pro Ser Gly Tyr Thr Ser Gly Gly Phe Asp Val
1               5                   10                  15

<210> SEQ ID NO 60
<211> LENGTH: 5
<212> TYPE: PRT
<213> ORGANISM: Artificial Sequence
<220> FEATURE:
<223> OTHER INFORMATION: Synthetic Construct

<400> SEQUENCE: 60

Ser Tyr Ala Met Ser
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic Construct

<400> SEQUENCE: 61

Gly Phe Ile Phe Ser Ser Phe
1               5

<210> SEQ ID NO 62
<211> LENGTH: 10
<212> TYPE: PRT
<213> ORGANISM: Artificial Sequence
<220> FEATURE:
<223> OTHER INFORMATION: Synthetic Construct

<400> SEQUENCE: 62

Gly Phe Ile Phe Ala Ser Tyr Ala Met Ser
1               5                   10

<210> SEQ ID NO 63
<211> LENGTH: 17
<212> TYPE: PRT
<213> ORGANISM: Artificial Sequence
<220> FEATURE:
<223> OTHER INFORMATION: Synthetic Construct

<400> SEQUENCE: 63

Glu Ile Ser Ser Ser Gly Gly Ser Thr Thr Tyr Ala Asp Ser Val Lys
1               5                   10                  15

Gly

<210> SEQ ID NO 64
<211> LENGTH: 6
<212> TYPE: PRT
<213> ORGANISM: Artificial Sequence
<220> FEATURE:
<223> OTHER INFORMATION: Synthetic Construct

<400> SEQUENCE: 64

Ser Ser Ser Gly Gly Ser
1               5

<210> SEQ ID NO 65
<211> LENGTH: 14
<212> TYPE: PRT
<213> ORGANISM: Artificial Sequence
<220> FEATURE:
<223> OTHER INFORMATION: Synthetic Construct

<400> SEQUENCE: 65

Asp Arg Val Met Ala Gly Leu Gly Tyr Asp Pro Phe Asp Tyr
1               5                   10

<210> SEQ ID NO 66
<211> LENGTH: 5
<212> TYPE: PRT
<213> ORGANISM: Artificial Sequence
<220> FEATURE:
<223> OTHER INFORMATION: Synthetic Construct

```
<400> SEQUENCE: 66

Ser Phe Ala Met Ser
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic Construct

<400> SEQUENCE: 67

Gly Phe Ile Phe Ser Ser Phe
1               5

<210> SEQ ID NO 68
<211> LENGTH: 10
<212> TYPE: PRT
<213> ORGANISM: Artificial Sequence
<220> FEATURE:
<223> OTHER INFORMATION: Synthetic Construct

<400> SEQUENCE: 68

Gly Phe Ile Phe Ser Ser Phe Ala Met Ser
1               5                   10

<210> SEQ ID NO 69
<211> LENGTH: 17
<212> TYPE: PRT
<213> ORGANISM: Artificial Sequence
<220> FEATURE:
<223> OTHER INFORMATION: Synthetic Construct

<400> SEQUENCE: 69

Asp Ile Ser Gly Ser Gly Ala Ser Thr Tyr Tyr Ala Asp Ser Val Lys
1               5                   10                  15
Gly

<210> SEQ ID NO 70
<211> LENGTH: 6
<212> TYPE: PRT
<213> ORGANISM: Artificial Sequence
<220> FEATURE:
<223> OTHER INFORMATION: Synthetic Construct

<400> SEQUENCE: 70

Ser Gly Ser Gly Ala Ser
1               5

<210> SEQ ID NO 71
<211> LENGTH: 14
<212> TYPE: PRT
<213> ORGANISM: Artificial Sequence
<220> FEATURE:
<223> OTHER INFORMATION: Synthetic Construct

<400> SEQUENCE: 71

Ala Ser Gly Gly Ser Gly Ser Tyr Trp Pro Tyr Met Asp Pro
1               5                   10

<210> SEQ ID NO 72
<211> LENGTH: 5
<212> TYPE: PRT
<213> ORGANISM: Artificial Sequence
<220> FEATURE:
<223> OTHER INFORMATION: Synthetic Construct
```

```
<400> SEQUENCE: 72

Arg Tyr Ala Leu Ser
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic Construct

<400> SEQUENCE: 73

Gly Gly Val Phe Ser Arg Tyr
1               5

<210> SEQ ID NO 74
<211> LENGTH: 10
<212> TYPE: PRT
<213> ORGANISM: Artificial Sequence
<220> FEATURE:
<223> OTHER INFORMATION: Synthetic Construct

<400> SEQUENCE: 74

Gly Gly Val Phe Ser Arg Tyr Ala Leu Ser
1               5                   10

<210> SEQ ID NO 75
<211> LENGTH: 17
<212> TYPE: PRT
<213> ORGANISM: Artificial Sequence
<220> FEATURE:
<223> OTHER INFORMATION: Synthetic Construct

<400> SEQUENCE: 75

Gly Ile Ile Pro Met Leu Gly Phe Ala Asn Tyr Ala Gln Lys Phe Gln
1               5                   10                  15

Gly

<210> SEQ ID NO 76
<211> LENGTH: 6
<212> TYPE: PRT
<213> ORGANISM: Artificial Sequence
<220> FEATURE:
<223> OTHER INFORMATION: Synthetic Construct

<400> SEQUENCE: 76

Ile Pro Met Leu Gly Phe
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic Construct

<400> SEQUENCE: 77

Leu Asp Phe Gly Ala Leu Asp Tyr
1               5

<210> SEQ ID NO 78
<211> LENGTH: 5
<212> TYPE: PRT
<213> ORGANISM: Artificial Sequence
<220> FEATURE:
```

```
<223> OTHER INFORMATION: Synthetic Construct

<400> SEQUENCE: 78

Ser Phe Asp Ile Ser
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic Construct

<400> SEQUENCE: 79

Gly Gly Thr Phe Arg Ser Phe
1               5

<210> SEQ ID NO 80
<211> LENGTH: 10
<212> TYPE: PRT
<213> ORGANISM: Artificial Sequence
<220> FEATURE:
<223> OTHER INFORMATION: Synthetic Construct

<400> SEQUENCE: 80

Gly Gly Thr Phe Arg Ser Phe Asp Ile Ser
1               5                   10

<210> SEQ ID NO 81
<211> LENGTH: 17
<212> TYPE: PRT
<213> ORGANISM: Artificial Sequence
<220> FEATURE:
<223> OTHER INFORMATION: Synthetic Construct

<400> SEQUENCE: 81

Arg Ile Ile Pro Ile Leu Gly Tyr Ala Asn Tyr Ala Gln Lys Phe Gln
1               5                   10                  15

Gly

<210> SEQ ID NO 82
<211> LENGTH: 6
<212> TYPE: PRT
<213> ORGANISM: Artificial Sequence
<220> FEATURE:
<223> OTHER INFORMATION: Synthetic Construct

<400> SEQUENCE: 82

Ile Pro Ile Leu Gly Tyr
1               5

<210> SEQ ID NO 83
<211> LENGTH: 13
<212> TYPE: PRT
<213> ORGANISM: Artificial Sequence
<220> FEATURE:
<223> OTHER INFORMATION: Synthetic Construct

<400> SEQUENCE: 83

Asp Leu Gly Ala Pro Trp Ala Gly Tyr Pro Phe Asp Pro
1               5                   10

<210> SEQ ID NO 84
<211> LENGTH: 5
<212> TYPE: PRT
<213> ORGANISM: Artificial Sequence
```

```
<220> FEATURE:
<223> OTHER INFORMATION: Synthetic Construct

<400> SEQUENCE: 84

Ser Tyr Ala Met His
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic Construct

<400> SEQUENCE: 85

Gly Phe Thr Phe Ser Ser Tyr
1               5

<210> SEQ ID NO 86
<211> LENGTH: 10
<212> TYPE: PRT
<213> ORGANISM: Artificial Sequence
<220> FEATURE:
<223> OTHER INFORMATION: Synthetic Construct

<400> SEQUENCE: 86

Gly Phe Thr Phe Ser Ser Tyr Ala Met His
1               5                   10

<210> SEQ ID NO 87
<211> LENGTH: 17
<212> TYPE: PRT
<213> ORGANISM: Artificial Sequence
<220> FEATURE:
<223> OTHER INFORMATION: Synthetic Construct

<400> SEQUENCE: 87

Ala Ile Ser Gly Ser Gly Gly Ser Thr Tyr Tyr Ala Asp Ser Val Lys
1               5                   10                  15
Gly

<210> SEQ ID NO 88
<211> LENGTH: 6
<212> TYPE: PRT
<213> ORGANISM: Artificial Sequence
<220> FEATURE:
<223> OTHER INFORMATION: Synthetic Construct

<400> SEQUENCE: 88

Ser Gly Ser Gly Gly Ser
1               5

<210> SEQ ID NO 89
<211> LENGTH: 12
<212> TYPE: PRT
<213> ORGANISM: Artificial Sequence
<220> FEATURE:
<223> OTHER INFORMATION: Synthetic Construct

<400> SEQUENCE: 89

Gly Thr Arg Trp Trp Trp Gly Asp Ala Phe Asp His
1               5                   10

<210> SEQ ID NO 90
<211> LENGTH: 5
<212> TYPE: PRT
```

```
<213> ORGANISM: Artificial Sequence
<220> FEATURE:
<223> OTHER INFORMATION: Synthetic Construct

<400> SEQUENCE: 90

Ser Tyr Ala Ile Gln
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic Construct

<400> SEQUENCE: 91

Gly Gly Thr Phe Ser Ser Tyr
1               5

<210> SEQ ID NO 92
<211> LENGTH: 10
<212> TYPE: PRT
<213> ORGANISM: Artificial Sequence
<220> FEATURE:
<223> OTHER INFORMATION: Synthetic Construct

<400> SEQUENCE: 92

Gly Gly Thr Phe Ser Ser Tyr Ala Ile Gln
1               5                   10

<210> SEQ ID NO 93
<211> LENGTH: 17
<212> TYPE: PRT
<213> ORGANISM: Artificial Sequence
<220> FEATURE:
<223> OTHER INFORMATION: Synthetic Construct

<400> SEQUENCE: 93

Gly Ile Val Gly Ser Trp Gly Leu Ala Asn Tyr Ala Gln Lys Phe Gln
1               5                   10                  15

Gly

<210> SEQ ID NO 94
<211> LENGTH: 6
<212> TYPE: PRT
<213> ORGANISM: Artificial Sequence
<220> FEATURE:
<223> OTHER INFORMATION: Synthetic Construct

<400> SEQUENCE: 94

Val Gly Ser Trp Gly Leu
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic Construct

<400> SEQUENCE: 95

Ser Ala Phe Gly Glu Leu Ala Ser
1               5

<210> SEQ ID NO 96
<211> LENGTH: 5
```

```
<212> TYPE: PRT
<213> ORGANISM: Artificial Sequence
<220> FEATURE:
<223> OTHER INFORMATION: Synthetic Construct

<400> SEQUENCE: 96

Arg Tyr Ala Leu Ser
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic Construct

<400> SEQUENCE: 97

Gly Gly Val Phe Ser Arg Tyr
1               5

<210> SEQ ID NO 98
<211> LENGTH: 10
<212> TYPE: PRT
<213> ORGANISM: Artificial Sequence
<220> FEATURE:
<223> OTHER INFORMATION: Synthetic Construct

<400> SEQUENCE: 98

Gly Gly Val Phe Ser Arg Tyr Ala Leu Ser
1               5                   10

<210> SEQ ID NO 99
<211> LENGTH: 17
<212> TYPE: PRT
<213> ORGANISM: Artificial Sequence
<220> FEATURE:
<223> OTHER INFORMATION: Synthetic Construct

<400> SEQUENCE: 99

Gly Ile Ile Pro Met Leu Gly Phe Ala Asn Tyr Ala Gln Lys Phe Gln
1               5                   10                  15

Gly

<210> SEQ ID NO 100
<211> LENGTH: 6
<212> TYPE: PRT
<213> ORGANISM: Artificial Sequence
<220> FEATURE:
<223> OTHER INFORMATION: Synthetic Construct

<400> SEQUENCE: 100

Ile Pro Met Leu Gly Phe
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic Construct

<400> SEQUENCE: 101

Leu Asp Phe Gly Ala Leu Asp Tyr
1               5

<210> SEQ ID NO 102
```

```
<211> LENGTH: 5
<212> TYPE: PRT
<213> ORGANISM: Artificial Sequence
<220> FEATURE:
<223> OTHER INFORMATION: Synthetic Construct

<400> SEQUENCE: 102

Ser Tyr Ala Met Asn
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic Construct

<400> SEQUENCE: 103

Gly Phe Thr Phe Ser Ser Tyr
1               5

<210> SEQ ID NO 104
<211> LENGTH: 10
<212> TYPE: PRT
<213> ORGANISM: Artificial Sequence
<220> FEATURE:
<223> OTHER INFORMATION: Synthetic Construct

<400> SEQUENCE: 104

Gly Phe Thr Phe Ser Ser Tyr Ala Met Asn
1               5                   10

<210> SEQ ID NO 105
<211> LENGTH: 17
<212> TYPE: PRT
<213> ORGANISM: Artificial Sequence
<220> FEATURE:
<223> OTHER INFORMATION: Synthetic Construct

<400> SEQUENCE: 105

Ser Ile Ser Gly Gly Gly Arg Ser Thr Tyr Tyr Ala Asp Ser Val Lys
1               5                   10                  15
Gly

<210> SEQ ID NO 106
<211> LENGTH: 6
<212> TYPE: PRT
<213> ORGANISM: Artificial Sequence
<220> FEATURE:
<223> OTHER INFORMATION: Synthetic Construct

<400> SEQUENCE: 106

Ser Gly Gly Gly Arg Ser
1               5

<210> SEQ ID NO 107
<211> LENGTH: 15
<212> TYPE: PRT
<213> ORGANISM: Artificial Sequence
<220> FEATURE:
<223> OTHER INFORMATION: Synthetic Construct

<400> SEQUENCE: 107

Asp Leu Ser Pro Ser Asp Val Gly Trp Gly Tyr Gly Phe Asp Ile
1               5                   10                  15
```

```
<210> SEQ ID NO 108
<211> LENGTH: 5
<212> TYPE: PRT
<213> ORGANISM: Artificial Sequence
<220> FEATURE:
<223> OTHER INFORMATION: Synthetic Construct

<400> SEQUENCE: 108

Ser Tyr Ala Met Asn
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic Construct

<400> SEQUENCE: 109

Gly Phe Thr Phe Ser Ser Tyr
1               5

<210> SEQ ID NO 110
<211> LENGTH: 10
<212> TYPE: PRT
<213> ORGANISM: Artificial Sequence
<220> FEATURE:
<223> OTHER INFORMATION: Synthetic Construct

<400> SEQUENCE: 110

Gly Phe Thr Phe Ser Ser Tyr Ala Met Asn
1               5                   10

<210> SEQ ID NO 111
<211> LENGTH: 17
<212> TYPE: PRT
<213> ORGANISM: Artificial Sequence
<220> FEATURE:
<223> OTHER INFORMATION: Synthetic Construct

<400> SEQUENCE: 111

Ser Ile Ser Gly Gly Gly Arg Ser Thr Tyr Tyr Ala Asp Ser Val Lys
1               5                   10                  15

Gly

<210> SEQ ID NO 112
<211> LENGTH: 6
<212> TYPE: PRT
<213> ORGANISM: Artificial Sequence
<220> FEATURE:
<223> OTHER INFORMATION: Synthetic Construct

<400> SEQUENCE: 112

Ser Gly Gly Gly Arg Ser
1               5

<210> SEQ ID NO 113
<211> LENGTH: 15
<212> TYPE: PRT
<213> ORGANISM: Artificial Sequence
<220> FEATURE:
<223> OTHER INFORMATION: Synthetic Construct

<400> SEQUENCE: 113

Asp Leu Ser Pro Ser Asp Val Gly Trp Gly Tyr Gly Phe Asp Ile
1               5                   10                  15
```

<210> SEQ ID NO 114
<211> LENGTH: 5
<212> TYPE: PRT
<213> ORGANISM: Artificial Sequence
<220> FEATURE:
<223> OTHER INFORMATION: Synthetic Construct

<400> SEQUENCE: 114

Asn Tyr Ala Met Asn
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic Construct

<400> SEQUENCE: 115

Gly Phe Thr Phe Asn Asn Tyr
1               5

<210> SEQ ID NO 116
<211> LENGTH: 10
<212> TYPE: PRT
<213> ORGANISM: Artificial Sequence
<220> FEATURE:
<223> OTHER INFORMATION: Synthetic Construct

<400> SEQUENCE: 116

Gly Phe Thr Phe Asn Asn Tyr Ala Met Asn
1               5                   10

<210> SEQ ID NO 117
<211> LENGTH: 17
<212> TYPE: PRT
<213> ORGANISM: Artificial Sequence
<220> FEATURE:
<223> OTHER INFORMATION: Synthetic Construct

<400> SEQUENCE: 117

Val Ile Ser Gly Ser Gly Gly Thr Thr Tyr Tyr Ala Asp Ser Val Lys
1               5                   10                  15

Gly

<210> SEQ ID NO 118
<211> LENGTH: 6
<212> TYPE: PRT
<213> ORGANISM: Artificial Sequence
<220> FEATURE:
<223> OTHER INFORMATION: Synthetic Construct

<400> SEQUENCE: 118

Ser Gly Ser Gly Gly Thr
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic Construct

<400> SEQUENCE: 119

Gly Ile Trp Asp Leu Arg Tyr
1               5

<210> SEQ ID NO 120
<211> LENGTH: 5
<212> TYPE: PRT
<213> ORGANISM: Artificial Sequence
<220> FEATURE:
<223> OTHER INFORMATION: Synthetic Construct

<400> SEQUENCE: 120

Ser Tyr Ala Ile Ser
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic Construct

<400> SEQUENCE: 121

Gly Gly Thr Phe Met Ser Tyr
1               5

<210> SEQ ID NO 122
<211> LENGTH: 10
<212> TYPE: PRT
<213> ORGANISM: Artificial Sequence
<220> FEATURE:
<223> OTHER INFORMATION: Synthetic Construct

<400> SEQUENCE: 122

Gly Gly Thr Phe Met Ser Tyr Ala Ile Ser
1               5                   10

<210> SEQ ID NO 123
<211> LENGTH: 17
<212> TYPE: PRT
<213> ORGANISM: Artificial Sequence
<220> FEATURE:
<223> OTHER INFORMATION: Synthetic Construct

<400> SEQUENCE: 123

Gly Ile Ile Pro Ile Phe Gly Ile Ala Asn Tyr Ala Gln Lys Phe Gln
1               5                   10                  15

Gly

<210> SEQ ID NO 124
<211> LENGTH: 6
<212> TYPE: PRT
<213> ORGANISM: Artificial Sequence
<220> FEATURE:
<223> OTHER INFORMATION: Synthetic Construct

<400> SEQUENCE: 124

Ile Pro Ile Phe Gly Ile
1               5

<210> SEQ ID NO 125
<211> LENGTH: 11
<212> TYPE: PRT
<213> ORGANISM: Artificial Sequence
<220> FEATURE:
<223> OTHER INFORMATION: Synthetic Construct

<400> SEQUENCE: 125

Glu Thr Leu Ile Tyr Pro Ile Pro Phe Glu Leu

<210> SEQ ID NO 126
<211> LENGTH: 5
<212> TYPE: PRT
<213> ORGANISM: Artificial Sequence
<220> FEATURE:
<223> OTHER INFORMATION: Synthetic Construct

<400> SEQUENCE: 126

Ser Tyr Ala Val Ser
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic Construct

<400> SEQUENCE: 127

Gly Gly Thr Phe Ser Ser Tyr
1               5

<210> SEQ ID NO 128
<211> LENGTH: 10
<212> TYPE: PRT
<213> ORGANISM: Artificial Sequence
<220> FEATURE:
<223> OTHER INFORMATION: Synthetic Construct

<400> SEQUENCE: 128

Gly Gly Thr Phe Ser Ser Tyr Ala Val Ser
1               5                   10

<210> SEQ ID NO 129
<211> LENGTH: 17
<212> TYPE: PRT
<213> ORGANISM: Artificial Sequence
<220> FEATURE:
<223> OTHER INFORMATION: Synthetic Construct

<400> SEQUENCE: 129

Gly Ile Ile Pro Ile Phe Gly Ile Ala Asn Tyr Ala Gln Lys Phe Gln
1               5                   10                  15

Gly

<210> SEQ ID NO 130
<211> LENGTH: 6
<212> TYPE: PRT
<213> ORGANISM: Artificial Sequence
<220> FEATURE:
<223> OTHER INFORMATION: Synthetic Construct

<400> SEQUENCE: 130

Ile Pro Ile Phe Gly Ile
1               5

<210> SEQ ID NO 131
<211> LENGTH: 14
<212> TYPE: PRT
<213> ORGANISM: Artificial Sequence
<220> FEATURE:
<223> OTHER INFORMATION: Synthetic Construct

<400> SEQUENCE: 131

```
Glu Gly Ile Gly Gly Asp Leu Arg Tyr Asp Gly Tyr Asp Ala
1               5                   10
```

<210> SEQ ID NO 132
<211> LENGTH: 5
<212> TYPE: PRT
<213> ORGANISM: Artificial Sequence
<220> FEATURE:
<223> OTHER INFORMATION: Synthetic Construct

<400> SEQUENCE: 132

```
Asn Tyr Val Met Asn
1               5
```

<210> SEQ ID NO 133
<211> LENGTH: 7
<212> TYPE: PRT
<213> ORGANISM: Artificial Sequence
<220> FEATURE:
<223> OTHER INFORMATION: Synthetic Construct

<400> SEQUENCE: 133

```
Gly Phe Thr Phe Ser Asn Tyr
1               5
```

<210> SEQ ID NO 134
<211> LENGTH: 10
<212> TYPE: PRT
<213> ORGANISM: Artificial Sequence
<220> FEATURE:
<223> OTHER INFORMATION: Synthetic Construct

<400> SEQUENCE: 134

```
Gly Phe Thr Phe Ser Asn Tyr Val Met Asn
1               5                   10
```

<210> SEQ ID NO 135
<211> LENGTH: 17
<212> TYPE: PRT
<213> ORGANISM: Artificial Sequence
<220> FEATURE:
<223> OTHER INFORMATION: Synthetic Construct

<400> SEQUENCE: 135

```
Ala Ile Ser Gly Ser Gly Ala Thr Thr Tyr Tyr Ala Asp Ser Val Lys
1               5                   10                  15

Gly
```

<210> SEQ ID NO 136
<211> LENGTH: 6
<212> TYPE: PRT
<213> ORGANISM: Artificial Sequence
<220> FEATURE:
<223> OTHER INFORMATION: Synthetic Construct

<400> SEQUENCE: 136

```
Ser Gly Ser Gly Ala Thr
1               5
```

<210> SEQ ID NO 137
<211> LENGTH: 7
<212> TYPE: PRT
<213> ORGANISM: Artificial Sequence
<220> FEATURE:
<223> OTHER INFORMATION: Synthetic Construct

<400> SEQUENCE: 137

Gly Leu Trp Ala Gly Gly Ile
1               5

<210> SEQ ID NO 138
<211> LENGTH: 5
<212> TYPE: PRT
<213> ORGANISM: Artificial Sequence
<220> FEATURE:
<223> OTHER INFORMATION: Synthetic Construct

<400> SEQUENCE: 138

Ser Tyr Ala Met Ser
1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic Construct

<400> SEQUENCE: 139

Gly Phe Thr Phe Ser Ser Tyr
1               5

<210> SEQ ID NO 140
<211> LENGTH: 10
<212> TYPE: PRT
<213> ORGANISM: Artificial Sequence
<220> FEATURE:
<223> OTHER INFORMATION: Synthetic Construct

<400> SEQUENCE: 140

Gly Phe Thr Phe Ser Ser Tyr Ala Met Ser
1               5                   10

<210> SEQ ID NO 141
<211> LENGTH: 17
<212> TYPE: PRT
<213> ORGANISM: Artificial Sequence
<220> FEATURE:
<223> OTHER INFORMATION: Synthetic Construct

<400> SEQUENCE: 141

Ala Ile Gly Gly Ser Gly Gly Ser Thr Tyr Tyr Ala Asp Ser Val Lys
1               5                   10                  15
Gly

<210> SEQ ID NO 142
<211> LENGTH: 6
<212> TYPE: PRT
<213> ORGANISM: Artificial Sequence
<220> FEATURE:
<223> OTHER INFORMATION: Synthetic Construct

<400> SEQUENCE: 142

Gly Gly Ser Gly Gly Ser
1               5

<210> SEQ ID NO 143
<211> LENGTH: 15
<212> TYPE: PRT
<213> ORGANISM: Artificial Sequence
<220> FEATURE:
<223> OTHER INFORMATION: Synthetic Construct

```
<400> SEQUENCE: 143

Asp Tyr Tyr Ala Phe Ser Asp Pro Ala Tyr Gly Gly Met Asp Val
1               5                   10                  15

<210> SEQ ID NO 144
<211> LENGTH: 12
<212> TYPE: PRT
<213> ORGANISM: Artificial Sequence
<220> FEATURE:
<223> OTHER INFORMATION: Synthetic Construct

<400> SEQUENCE: 144

Arg Ala Ser His Ser Val Ser Ser Ser Tyr Leu Ala
1               5                   10

<210> SEQ ID NO 145
<211> LENGTH: 7
<212> TYPE: PRT
<213> ORGANISM: Artificial Sequence
<220> FEATURE:
<223> OTHER INFORMATION: Synthetic Construct

<400> SEQUENCE: 145

Gly Ala Ser Ser Arg Ala Thr
1               5

<210> SEQ ID NO 146
<211> LENGTH: 9
<212> TYPE: PRT
<213> ORGANISM: Artificial Sequence
<220> FEATURE:
<223> OTHER INFORMATION: Synthetic Construct

<400> SEQUENCE: 146

Gln Gln Tyr Gly Ser Pro Pro Arg Thr
1               5

<210> SEQ ID NO 147
<211> LENGTH: 12
<212> TYPE: PRT
<213> ORGANISM: Artificial Sequence
<220> FEATURE:
<223> OTHER INFORMATION: Synthetic Construct

<400> SEQUENCE: 147

Arg Ala Ser Gln Tyr Val Ser Ala Ser Leu Leu Ala
1               5                   10

<210> SEQ ID NO 148
<211> LENGTH: 7
<212> TYPE: PRT
<213> ORGANISM: Artificial Sequence
<220> FEATURE:
<223> OTHER INFORMATION: Synthetic Construct

<400> SEQUENCE: 148

Gly Ala Ser Thr Arg Ala Thr
1               5

<210> SEQ ID NO 149
<211> LENGTH: 8
<212> TYPE: PRT
<213> ORGANISM: Artificial Sequence
<220> FEATURE:
<223> OTHER INFORMATION: Synthetic Construct

<400> SEQUENCE: 149
```

```
Gln Gln Tyr Ala Arg Ser Ser Thr
1               5
```

<210> SEQ ID NO 150
<211> LENGTH: 11
<212> TYPE: PRT
<213> ORGANISM: Artificial Sequence
<220> FEATURE:
<223> OTHER INFORMATION: Synthetic Construct

<400> SEQUENCE: 150

```
Arg Ala Ser Gln Ser Ile Ser Ser Tyr Leu Asn
1               5                   10
```

<210> SEQ ID NO 151
<211> LENGTH: 7
<212> TYPE: PRT
<213> ORGANISM: Artificial Sequence
<220> FEATURE:
<223> OTHER INFORMATION: Synthetic Construct

<400> SEQUENCE: 151

```
Ala Ala Ser Ser Leu Gln Ser
1               5
```

<210> SEQ ID NO 152
<211> LENGTH: 9
<212> TYPE: PRT
<213> ORGANISM: Artificial Sequence
<220> FEATURE:
<223> OTHER INFORMATION: Synthetic Construct

<400> SEQUENCE: 152

```
Gln Gln Ser Tyr Ser Thr Pro Leu Thr
1               5
```

<210> SEQ ID NO 153
<211> LENGTH: 14
<212> TYPE: PRT
<213> ORGANISM: Artificial Sequence
<220> FEATURE:
<223> OTHER INFORMATION: Synthetic Construct

<400> SEQUENCE: 153

```
Thr Gly Thr Ser Ser Asp Val Gly Gly Tyr Asn Tyr Val Ser
1               5                   10
```

<210> SEQ ID NO 154
<211> LENGTH: 7
<212> TYPE: PRT
<213> ORGANISM: Artificial Sequence
<220> FEATURE:
<223> OTHER INFORMATION: Synthetic Construct

<400> SEQUENCE: 154

```
Glu Val Ser Lys Arg Pro Ser
1               5
```

<210> SEQ ID NO 155
<211> LENGTH: 10
<212> TYPE: PRT
<213> ORGANISM: Artificial Sequence
<220> FEATURE:
<223> OTHER INFORMATION: Synthetic Construct

<400> SEQUENCE: 155

Ser Ser Tyr Ala Gly Ser Asn Thr Val Val
1               5                   10

<210> SEQ ID NO 156
<211> LENGTH: 13
<212> TYPE: PRT
<213> ORGANISM: Artificial Sequence
<220> FEATURE:
<223> OTHER INFORMATION: Synthetic Construct

<400> SEQUENCE: 156

Ser Gly Ser Ser Ser Asn Ile Gly Ser Asn Tyr Val Tyr
1               5                   10

<210> SEQ ID NO 157
<211> LENGTH: 7
<212> TYPE: PRT
<213> ORGANISM: Artificial Sequence
<220> FEATURE:
<223> OTHER INFORMATION: Synthetic Construct

<400> SEQUENCE: 157

Arg Asn Asn Gln Arg Pro Ser
1               5

<210> SEQ ID NO 158
<211> LENGTH: 11
<212> TYPE: PRT
<213> ORGANISM: Artificial Sequence
<220> FEATURE:
<223> OTHER INFORMATION: Synthetic Construct

<400> SEQUENCE: 158

Ala Ala Trp Asp Asp Ser Leu Ser Gly Val Val
1               5                   10

<210> SEQ ID NO 159
<211> LENGTH: 13
<212> TYPE: PRT
<213> ORGANISM: Artificial Sequence
<220> FEATURE:
<223> OTHER INFORMATION: Synthetic Construct

<400> SEQUENCE: 159

Ser Gly Ser Gly Ser Asn Ile Gly Ser Asn Tyr Val Tyr
1               5                   10

<210> SEQ ID NO 160
<211> LENGTH: 7
<212> TYPE: PRT
<213> ORGANISM: Artificial Sequence
<220> FEATURE:
<223> OTHER INFORMATION: Synthetic Construct

<400> SEQUENCE: 160

Arg Asn Asn Gln Arg Pro Ser
1               5

<210> SEQ ID NO 161
<211> LENGTH: 11
<212> TYPE: PRT
<213> ORGANISM: Artificial Sequence
<220> FEATURE:
<223> OTHER INFORMATION: Synthetic Construct

<400> SEQUENCE: 161

Ala Ala Trp Asp Gly Ser Leu Ser Arg Pro Val 1               5                  10

<210> SEQ ID NO 162
<211> LENGTH: 12
<212> TYPE: PRT
<213> ORGANISM: Artificial Sequence
<220> FEATURE:
<223> OTHER INFORMATION: Synthetic Construct

<400> SEQUENCE: 162

Arg Ala Ser Gln Ser Val Pro Asn Glu Gln Leu Ala
1               5                  10

<210> SEQ ID NO 163
<211> LENGTH: 7
<212> TYPE: PRT
<213> ORGANISM: Artificial Sequence
<220> FEATURE:
<223> OTHER INFORMATION: Synthetic Construct

<400> SEQUENCE: 163

Asp Ala Ser Ser Arg Ala Thr
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic Construct

<400> SEQUENCE: 164

Gln Gln Tyr Gly Ser Pro Pro Leu Thr
1               5

<210> SEQ ID NO 165
<211> LENGTH: 12
<212> TYPE: PRT
<213> ORGANISM: Artificial Sequence
<220> FEATURE:
<223> OTHER INFORMATION: Synthetic Construct

<400> SEQUENCE: 165

Arg Ala Ser Gln Ser Val Ser Ser Ser Glu Leu Ala
1               5                  10

<210> SEQ ID NO 166
<211> LENGTH: 7
<212> TYPE: PRT
<213> ORGANISM: Artificial Sequence
<220> FEATURE:
<223> OTHER INFORMATION: Synthetic Construct

<400> SEQUENCE: 166

Asp Ala Ser Ser Arg Ala Thr
1               5

<210> SEQ ID NO 167
<211> LENGTH: 9
<212> TYPE: PRT
<213> ORGANISM: Artificial Sequence
<220> FEATURE:
<223> OTHER INFORMATION: Synthetic Construct

<400> SEQUENCE: 167

Gln Gln Tyr Asp Ser Ser Pro Leu Thr
1               5

<210> SEQ ID NO 168
<211> LENGTH: 11
<212> TYPE: PRT
<213> ORGANISM: Artificial Sequence
<220> FEATURE:
<223> OTHER INFORMATION: Synthetic Construct

<400> SEQUENCE: 168

Gly Gly Asn Asn Ile Gly Ser Lys Ser Val His
1               5                   10

<210> SEQ ID NO 169
<211> LENGTH: 7
<212> TYPE: PRT
<213> ORGANISM: Artificial Sequence
<220> FEATURE:
<223> OTHER INFORMATION: Synthetic Construct

<400> SEQUENCE: 169

Tyr Asp Ser Asp Arg Pro Ser
1               5

<210> SEQ ID NO 170
<211> LENGTH: 10
<212> TYPE: PRT
<213> ORGANISM: Artificial Sequence
<220> FEATURE:
<223> OTHER INFORMATION: Synthetic Construct

<400> SEQUENCE: 170

Gln Val Trp Asp Ser Ser Thr Ala Trp Val
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Synthetic Construct

<400> SEQUENCE: 171

Arg Ala Ser Gln Ser Val Pro Ser Ser Gln Leu Ala
1               5                   10

<210> SEQ ID NO 172
<211> LENGTH: 7
<212> TYPE: PRT
<213> ORGANISM: Artificial Sequence
<220> FEATURE:
<223> OTHER INFORMATION: Synthetic Construct

<400> SEQUENCE: 172

Asp Ala Ser Ser Arg Ala Thr
1               5

<210> SEQ ID NO 173
<211> LENGTH: 9
<212> TYPE: PRT
<213> ORGANISM: Artificial Sequence
<220> FEATURE:
<223> OTHER INFORMATION: Synthetic Construct

<400> SEQUENCE: 173

Gln Gln Tyr Gly Ser Ser Pro Leu Thr
1               5

```
<210> SEQ ID NO 174
<211> LENGTH: 12
<212> TYPE: PRT
<213> ORGANISM: Artificial Sequence
<220> FEATURE:
<223> OTHER INFORMATION: Synthetic Construct

<400> SEQUENCE: 174

Arg Ala Ser Gln Ala Val Asp Ser Ser Asp Leu Ala
1               5                   10

<210> SEQ ID NO 175
<211> LENGTH: 7
<212> TYPE: PRT
<213> ORGANISM: Artificial Sequence
<220> FEATURE:
<223> OTHER INFORMATION: Synthetic Construct

<400> SEQUENCE: 175

Asp Ala Tyr Thr Arg Pro Ser
1               5

<210> SEQ ID NO 176
<211> LENGTH: 9
<212> TYPE: PRT
<213> ORGANISM: Artificial Sequence
<220> FEATURE:
<223> OTHER INFORMATION: Synthetic Construct

<400> SEQUENCE: 176

Gln Gln Tyr Gly Ser Ser Pro Leu Thr
1               5

<210> SEQ ID NO 177
<211> LENGTH: 11
<212> TYPE: PRT
<213> ORGANISM: Artificial Sequence
<220> FEATURE:
<223> OTHER INFORMATION: Synthetic Construct

<400> SEQUENCE: 177

Arg Ala Ser Gln Ser Val Ser Ser Asn Leu Ala
1               5                   10

<210> SEQ ID NO 178
<211> LENGTH: 7
<212> TYPE: PRT
<213> ORGANISM: Artificial Sequence
<220> FEATURE:
<223> OTHER INFORMATION: Synthetic Construct

<400> SEQUENCE: 178

Asp Thr Phe Thr Arg Ala Thr
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic Construct

<400> SEQUENCE: 179

Gln Gln Tyr Gly Ser Ser Pro Pro Thr
1               5
```

```
<210> SEQ ID NO 180
<211> LENGTH: 12
<212> TYPE: PRT
<213> ORGANISM: Artificial Sequence
<220> FEATURE:
<223> OTHER INFORMATION: Synthetic Construct

<400> SEQUENCE: 180

Arg Ala Ser Gln Ser Val Ser Asn Thr Tyr Leu Ala
1               5                   10

<210> SEQ ID NO 181
<211> LENGTH: 7
<212> TYPE: PRT
<213> ORGANISM: Artificial Sequence
<220> FEATURE:
<223> OTHER INFORMATION: Synthetic Construct

<400> SEQUENCE: 181

Asp Thr Ser Ser Arg Ala Thr
1               5

<210> SEQ ID NO 182
<211> LENGTH: 8
<212> TYPE: PRT
<213> ORGANISM: Artificial Sequence
<220> FEATURE:
<223> OTHER INFORMATION: Synthetic Construct

<400> SEQUENCE: 182

Gln Gln Tyr Gly Ser Ser Leu Thr
1               5

<210> SEQ ID NO 183
<211> LENGTH: 11
<212> TYPE: PRT
<213> ORGANISM: Artificial Sequence
<220> FEATURE:
<223> OTHER INFORMATION: Synthetic Construct

<400> SEQUENCE: 183

Arg Ala Ser Gln Ser Ile Ser Thr Tyr Leu Asn
1               5                   10

<210> SEQ ID NO 184
<211> LENGTH: 7
<212> TYPE: PRT
<213> ORGANISM: Artificial Sequence
<220> FEATURE:
<223> OTHER INFORMATION: Synthetic Construct

<400> SEQUENCE: 184

Ala Ala Ser Asn Leu Gln Ser
1               5

<210> SEQ ID NO 185
<211> LENGTH: 9
<212> TYPE: PRT
<213> ORGANISM: Artificial Sequence
<220> FEATURE:
<223> OTHER INFORMATION: Synthetic Construct

<400> SEQUENCE: 185

Gln Gln Ser Tyr Ser Ile Pro Leu Thr
1               5

<210> SEQ ID NO 186
```

```
<211> LENGTH: 12
<212> TYPE: PRT
<213> ORGANISM: Artificial Sequence
<220> FEATURE:
<223> OTHER INFORMATION: Synthetic Construct

<400> SEQUENCE: 186

Arg Ala Ser Gln Ile Val Ser Ser Ser Tyr Leu Ala
1               5                   10

<210> SEQ ID NO 187
<211> LENGTH: 7
<212> TYPE: PRT
<213> ORGANISM: Artificial Sequence
<220> FEATURE:
<223> OTHER INFORMATION: Synthetic Construct

<400> SEQUENCE: 187

Gly Ala Ser Ser Arg Ala Ser
1               5

<210> SEQ ID NO 188
<211> LENGTH: 9
<212> TYPE: PRT
<213> ORGANISM: Artificial Sequence
<220> FEATURE:
<223> OTHER INFORMATION: Synthetic Construct

<400> SEQUENCE: 188

Gln Gln Tyr Gly Gly Ser Pro Tyr Thr
1               5

<210> SEQ ID NO 189
<211> LENGTH: 12
<212> TYPE: PRT
<213> ORGANISM: Artificial Sequence
<220> FEATURE:
<223> OTHER INFORMATION: Synthetic Construct

<400> SEQUENCE: 189

Arg Ala Ser Gln Ser Val Ser His Ser Tyr Leu Ala
1               5                   10

<210> SEQ ID NO 190
<211> LENGTH: 7
<212> TYPE: PRT
<213> ORGANISM: Artificial Sequence
<220> FEATURE:
<223> OTHER INFORMATION: Synthetic Construct

<400> SEQUENCE: 190

Gly Ala Ser Phe Arg Ala Ala
1               5

<210> SEQ ID NO 191
<211> LENGTH: 9
<212> TYPE: PRT
<213> ORGANISM: Artificial Sequence
<220> FEATURE:
<223> OTHER INFORMATION: Synthetic Construct

<400> SEQUENCE: 191

Gln Gln Tyr Gly Ser Asp Pro Tyr Thr
1               5

<210> SEQ ID NO 192
<211> LENGTH: 11
```

```
<212> TYPE: PRT
<213> ORGANISM: Artificial Sequence
<220> FEATURE:
<223> OTHER INFORMATION: Synthetic Construct

<400> SEQUENCE: 192

Arg Ala Ser Gln Ser Ile Ser Ser Tyr Leu Asn
1               5                   10

<210> SEQ ID NO 193
<211> LENGTH: 7
<212> TYPE: PRT
<213> ORGANISM: Artificial Sequence
<220> FEATURE:
<223> OTHER INFORMATION: Synthetic Construct

<400> SEQUENCE: 193

Asp Ala Ser Asp Leu Gln Arg
1               5

<210> SEQ ID NO 194
<211> LENGTH: 9
<212> TYPE: PRT
<213> ORGANISM: Artificial Sequence
<220> FEATURE:
<223> OTHER INFORMATION: Synthetic Construct

<400> SEQUENCE: 194

Gln Gln Ser Tyr Asn Thr Pro Trp Thr
1               5

<210> SEQ ID NO 195
<211> LENGTH: 13
<212> TYPE: PRT
<213> ORGANISM: Artificial Sequence
<220> FEATURE:
<223> OTHER INFORMATION: Synthetic Construct

<400> SEQUENCE: 195

Thr Arg Ser Ser Gly Ser Ile Ala Ser Asn Tyr Val Gln
1               5                   10

<210> SEQ ID NO 196
<211> LENGTH: 7
<212> TYPE: PRT
<213> ORGANISM: Artificial Sequence
<220> FEATURE:
<223> OTHER INFORMATION: Synthetic Construct

<400> SEQUENCE: 196

Asp Asp Ser Asp Arg Pro Ser
1               5

<210> SEQ ID NO 197
<211> LENGTH: 11
<212> TYPE: PRT
<213> ORGANISM: Artificial Sequence
<220> FEATURE:
<223> OTHER INFORMATION: Synthetic Construct

<400> SEQUENCE: 197

Gln Val Trp Asp Ser Ser Ser Asp His Trp Val
1               5                   10

<210> SEQ ID NO 198
<211> LENGTH: 255
<212> TYPE: PRT
```

-continued

<213> ORGANISM: Homo sapiens

<400> SEQUENCE: 198

Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
            20                  25                  30

Ile Lys Cys Val Leu Ile Asn His Lys Asn Asn Asp Ser Ser Val Gly
        35                  40                  45

Lys Ser Ser Tyr Pro Met Val Ser Glu Ser Pro Glu Asp Leu Gly
    50                  55                  60

Cys Ala Leu Arg Pro Gln Ser Ser Gly Thr Val Tyr Glu Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr
                245                 250                 255

<210> SEQ ID NO 199
<211> LENGTH: 135
<212> TYPE: PRT
<213> ORGANISM: Homo sapiens

<400> SEQUENCE: 199

Asn Gln Asp Leu Pro Val Ile Lys Cys Val Leu Ile Asn His Lys Asn
1               5                   10                  15

Asn Asp Ser Ser Val Gly Lys Ser Ser Tyr Pro Met Val Ser Glu
            20                  25                  30

Ser Pro Glu Asp Leu Gly Cys Ala Leu Arg Pro Gln Ser Ser Gly Thr
    35                  40                  45

Val Tyr Glu Ala Ala Val Glu Val Asp Val Ser Ala Ser Ile Thr
50                  55                  60

Leu Gln Val Leu Val Asp Ala Pro Gly Asn Ile Ser Cys Leu Trp Val
65                  70                  75                  80

Phe Lys His Ser Ser Leu Asn Cys Gln Pro His Phe Asp Leu Gln Asn
                85                  90                  95

Arg Gly Val Val Ser Met Val Ile Leu Lys Met Thr Glu Thr Gln Ala

```
                    100                 105                 110
Gly Glu Tyr Leu Leu Phe Ile Gln Ser Glu Ala Thr Asn Tyr Thr Ile
            115                 120                 125

Leu Phe Thr Val Ser Ile Arg
            130                 135

<210> SEQ ID NO 200
<211> LENGTH: 82
<212> TYPE: PRT
<213> ORGANISM: Homo sapiens

<400> SEQUENCE: 200

Asn Thr Leu Leu Tyr Leu Arg Arg Pro Tyr Phe Arg Lys Met Glu Asn
1               5                   10                  15

Gln Asp Ala Leu Val Cys Ile Ser Glu Ser Val Pro Glu Pro Ile Val
            20                  25                  30

Glu Trp Val Leu Cys Asp Ser Gln Gly Glu Ser Cys Lys Glu Glu Ser
        35                  40                  45

Pro Ala Val Val Lys Lys Glu Glu Lys Val Leu His Glu Leu Phe Gly
    50                  55                  60

Thr Asp Ile Arg Cys Cys Ala Arg Asn Glu Leu Gly Arg Glu Cys Thr
65                  70                  75                  80

Arg Leu

<210> SEQ ID NO 201
<211> LENGTH: 102
<212> TYPE: PRT
<213> ORGANISM: Homo sapiens

<400> SEQUENCE: 201

Phe Thr Ile Asp Leu Asn Gln Thr Pro Gln Thr Thr Leu Pro Gln Leu
1               5                   10                  15

Phe Leu Lys Val Gly Glu Pro Leu Trp Ile Arg Cys Lys Ala Val His
            20                  25                  30

Val Asn His Gly Phe Gly Leu Thr Trp Glu Leu Glu Asn Lys Ala Leu
        35                  40                  45

Glu Glu Gly Asn Tyr Phe Glu Met Ser Thr Tyr Ser Thr Asn Arg Thr
    50                  55                  60

Met Ile Arg Ile Leu Phe Ala Phe Val Ser Ser Val Ala Arg Asn Asp
65                  70                  75                  80

Thr Gly Tyr Tyr Thr Cys Ser Ser Ser Lys His Pro Ser Gln Ser Ala
                85                  90                  95

Leu Val Thr Ile Val Glu
            100

<210> SEQ ID NO 202
<211> LENGTH: 88
<212> TYPE: PRT
<213> ORGANISM: Homo sapiens

<400> SEQUENCE: 202

Lys Gly Phe Ile Asn Ala Thr Asn Ser Ser Glu Asp Tyr Glu Ile Asp
1               5                   10                  15

Gln Tyr Glu Glu Phe Cys Phe Ser Val Arg Phe Lys Ala Tyr Pro Gln
            20                  25                  30

Ile Arg Cys Thr Trp Thr Phe Ser Arg Lys Ser Phe Pro Cys Glu Gln
        35                  40                  45
```

```
<210> SEQ ID NO 203
<211> LENGTH: 107
<212> TYPE: PRT
<213> ORGANISM: Homo sapiens

<400> SEQUENCE: 203

Ile Arg Arg Lys Pro Gln Val Leu Ala Glu Ala Ser Ala Ser Gln Ala
1               5                   10                  15

Ser Cys Phe Ser Asp Gly Tyr Pro Leu Pro Ser Trp Thr Trp Lys Lys
            20                  25                  30

Cys Ser Asp Lys Ser Pro Asn Cys Thr Glu Glu Ile Thr Glu Gly Val
        35                  40                  45

Trp Asn Arg Lys Ala Asn Arg Lys Val Phe Gly Gln Trp Val Ser Ser
    50                  55                  60

Ser Thr Leu Asn Met Ser Glu Ala Ile Lys Gly Phe Leu Val Lys Cys
65                  70                  75                  80

Cys Ala Tyr Asn Ser Leu Gly Thr Ser Cys Glu Thr Ile Leu Leu Asn
                85                  90                  95

Ser Pro Gly Pro Phe Pro Phe Ile Gln Asp Asn
            100                 105

<210> SEQ ID NO 204
<211> LENGTH: 108
<212> TYPE: PRT
<213> ORGANISM: Artificial Sequence
<220> FEATURE:
<223> OTHER INFORMATION: Synthetic Construct

<400> SEQUENCE: 204

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser His Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Phe Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Glu Pro
                85                  90                  95

Tyr Thr Phe Gly Gln Gly Thr Lys Val Glu Ile Lys
            100                 105

<210> SEQ ID NO 205
<211> LENGTH: 123
<212> TYPE: PRT
<213> ORGANISM: Artificial Sequence
<220> FEATURE:
<223> OTHER INFORMATION: Synthetic Construct

<400> SEQUENCE: 205
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Val Ser Trp Val Arg Gln Ala Pro Gly Gln Gly Leu Glu Trp Met
            35                  40                  45

Gly Gly Ile Ile Pro Ile Phe Gly Ile Ala Asn Tyr Ala Gln Lys Phe
        50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Ile Glu Gly Ile Gly Gly Asp Leu Arg Tyr Glu Gly Tyr Asp Ala
            100                 105                 110

Trp Gly Gln Gly Thr Leu Val Thr Val Ser Ser
            115                 120
```

<210> SEQ ID NO 206
<211> LENGTH: 109
<212> TYPE: PRT
<213> ORGANISM: Artificial Sequence
<220> FEATURE:
<223> OTHER INFORMATION: Synthetic Construct

<400> SEQUENCE: 206

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Gln Leu Ala Trp Tyr Gln Gln Lys Pro Gly Gln Ala Pro Arg Leu Leu
            35                  40                  45

Ile Tyr Asp Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
            85                  90                  95

Leu Ile Thr Phe Gly Gln Gly Thr Lys Val Glu Ile Lys
            100                 105
```

<210> SEQ ID NO 207
<211> LENGTH: 117
<212> TYPE: PRT
<213> ORGANISM: Artificial Sequence
<220> FEATURE:
<223> OTHER INFORMATION: Synthetic Construct

<400> SEQUENCE: 207

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Tyr Ile Thr Trp Val Arg Gln Ala Pro Gly Gln Gly Leu Glu Trp Met
            35                  40                  45

Gly Arg Ile Met Pro Ala Phe Gly Trp Thr Asn Tyr Ala Gln Lys Phe
        50                  55                  60

Gln Gly Arg Val Thr Ile Thr Thr Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Ser Asp Glu Phe Gly Ala Phe Asp Val Trp Gly Gln Gly Thr Leu
            100                 105                 110

Val Thr Val Ser Ser
        115

<210> SEQ ID NO 208
<211> LENGTH: 108
<212> TYPE: PRT
<213> ORGANISM: Artificial Sequence
<220> FEATURE:
<223> OTHER INFORMATION: Synthetic Construct

<400> SEQUENCE: 208

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ala Val Asp Ser Ser
            20                  25                  30

Asp Leu Ala Trp Tyr Gln His Lys Pro Gly Gln Ala Pro Arg Leu Leu
        35                  40                  45

Ile Tyr Asp Ala Tyr Thr Arg Pro Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Leu Glu Ile Lys
            100                 105

<210> SEQ ID NO 209
<211> LENGTH: 117
<212> TYPE: PRT
<213> ORGANISM: Artificial Sequence
<220> FEATURE:
<223> OTHER INFORMATION: Synthetic Construct

<400> SEQUENCE: 209

Gln Val Gln Leu Val Gln Ser Gly Ala Glu Val Lys Lys Pro Gly Ser
1               5                   10                  15

Ser Val Lys Val Ser Cys Lys Ala Ser Gly Gly Val Phe Ser Arg Tyr
            20                  25                  30

Ala Leu Ser Trp Val Arg Gln Ala Pro Gly Gln Gly Leu Glu Trp Met
        35                  40                  45

Gly Gly Ile Ile Pro Met Leu Gly Phe Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Leu Asp Phe Gly Ala Leu Asp Tyr Trp Gly Gln Gly Thr Leu
            100                 105                 110

Val Thr Val Ser Ser
        115

<210> SEQ ID NO 210
<211> LENGTH: 106
<212> TYPE: PRT
```

<213> ORGANISM: Artificial Sequence
<220> FEATURE:
<223> OTHER INFORMATION: Synthetic Construct

<400> SEQUENCE: 210

Asp Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Tyr Thr Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Pro Tyr Thr
                85                  90                  95

Phe Gly Gln Gly Thr Lys Val Glu Ile Lys
            100                 105

<210> SEQ ID NO 211
<211> LENGTH: 121
<212> TYPE: PRT
<213> ORGANISM: Artificial Sequence
<220> FEATURE:
<223> OTHER INFORMATION: Synthetic Construct

<400> SEQUENCE: 211

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Asp Ile Ser Trp Val Arg Gln Ala Pro Gly Gln Gly Leu Glu Trp Met
        35                  40                  45

Gly Arg Ile Ile Pro Ser Phe Gly Ala Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Asp Gly Glu Gly Trp Thr Pro Pro Phe Gly Tyr Trp Gly
            100                 105                 110

Gln Gly Thr Leu Val Thr Val Ser Ser
        115                 120

<210> SEQ ID NO 212
<211> LENGTH: 107
<212> TYPE: PRT
<213> ORGANISM: Artificial Sequence
<220> FEATURE:
<223> OTHER INFORMATION: Synthetic Construct

<400> SEQUENCE: 212

Asp Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

```
Tyr Asp Thr Phe Thr Arg Ala Thr Gly Ile Pro Ala Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Thr Phe Gly Gln Gly Thr Arg Leu Glu Ile Lys
            100                 105

<210> SEQ ID NO 213
<211> LENGTH: 124
<212> TYPE: PRT
<213> ORGANISM: Artificial Sequence
<220> FEATURE:
<223> OTHER INFORMATION: Synthetic Construct

<400> SEQUENCE: 213

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Ser Ile Ser Gly Gly Gly Arg Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120

<210> SEQ ID NO 214
<211> LENGTH: 107
<212> TYPE: PRT
<213> ORGANISM: Artificial Sequence
<220> FEATURE:
<223> OTHER INFORMATION: Synthetic Construct

<400> SEQUENCE: 214

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Asp Thr Phe Thr Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Gly Ser Ser Pro Pro
                85                  90                  95

Thr Phe Gly Gln Gly Thr Arg Leu Glu Ile Lys
            100                 105
```

```
<210> SEQ ID NO 215
<211> LENGTH: 124
<212> TYPE: PRT
<213> ORGANISM: Artificial Sequence
<220> FEATURE:
<223> OTHER INFORMATION: Synthetic Construct

<400> SEQUENCE: 215

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120

<210> SEQ ID NO 216
<211> LENGTH: 107
<212> TYPE: PRT
<213> ORGANISM: Artificial Sequence
<220> FEATURE:
<223> OTHER INFORMATION: Synthetic Construct

<400> SEQUENCE: 216

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Val Ser Asp Leu
            20                  25                  30

Leu Ala Trp Tyr Gln Gln Lys Pro Gly Gln Ala Pro Arg Leu Leu Ile
        35                  40                  45

Tyr Asp Ala Tyr Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ala Ser Ser Pro Ile
                85                  90                  95

Thr Phe Gly Gln Gly Thr Arg Leu Glu Ile Lys
            100                 105

<210> SEQ ID NO 217
<211> LENGTH: 124
<212> TYPE: PRT
<213> ORGANISM: Artificial Sequence
<220> FEATURE:
<223> OTHER INFORMATION: Synthetic Construct

<400> SEQUENCE: 217

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Asn Trp Val Arg Gln Ala Pro Gly Lys Gly Leu Glu Trp Val
            35                  40                  45

Ser Ser Ile Ser Gly Gly Gly Arg Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
                100                 105                 110

Ile Trp Gly Gln Gly Thr Leu Val Thr Val Ser Ser
            115                 120
```

<210> SEQ ID NO 218
<211> LENGTH: 107
<212> TYPE: PRT
<213> ORGANISM: Artificial Sequence
<220> FEATURE:
<223> OTHER INFORMATION: Synthetic Construct

<400> SEQUENCE: 218

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Lys Val Ser Asp Leu
                20                  25                  30

Leu Ala Trp Tyr Gln Gln Lys Pro Gly Gln Ala Pro Arg Leu Leu Ile
            35                  40                  45

Tyr Asp Ala Tyr Thr Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Tyr Thr Gly Ser Pro Ile
                85                  90                  95

Thr Phe Gly Gln Gly Thr Arg Leu Glu Ile Lys
                100                 105
```

<210> SEQ ID NO 219
<211> LENGTH: 124
<212> TYPE: PRT
<213> ORGANISM: Artificial Sequence
<220> FEATURE:
<223> OTHER INFORMATION: Synthetic Construct

<400> SEQUENCE: 219

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Ser Ile Ser Gly Gly Gly Arg Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
```

-continued

```
                100                 105                 110

Ile Trp Gly Gln Gly Thr Leu Val Thr Val Ser Ser
            115                 120

<210> SEQ ID NO 220
<211> LENGTH: 107
<212> TYPE: PRT
<213> ORGANISM: Artificial Sequence
<220> FEATURE:
<223> OTHER INFORMATION: Synthetic Construct

<400> SEQUENCE: 220

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Leu Ser Val Ser Asp Leu
            20                  25                  30

Leu Ala Trp Tyr Gln Gln Lys Pro Gly Gln Ala Pro Arg Leu Leu Ile
        35                  40                  45

Tyr Asp Ala Tyr Ser Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ser Ser Asn Pro Ile
                85                  90                  95

Thr Phe Gly Gln Gly Thr Arg Leu Glu Ile Lys
            100                 105

<210> SEQ ID NO 221
<211> LENGTH: 124
<212> TYPE: PRT
<213> ORGANISM: Artificial Sequence
<220> FEATURE:
<223> OTHER INFORMATION: Synthetic Construct

<400> SEQUENCE: 221

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
            115                 120

<210> SEQ ID NO 222
<211> LENGTH: 107
<212> TYPE: PRT
<213> ORGANISM: Artificial Sequence
<220> FEATURE:
<223> OTHER INFORMATION: Synthetic Construct

<400> SEQUENCE: 222
```

-continued

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gly Ser Val Ser Asp Leu
            20                  25                  30

Leu Ala Trp Tyr Gln Gln Lys Pro Gly Gln Ala Pro Arg Leu Leu Ile
        35                  40                  45

Tyr Asp Ala Tyr Ser Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ala Ser Tyr Pro Ile
                85                  90                  95

Thr Phe Gly Gln Gly Thr Arg Leu Glu Ile Lys
            100                 105

<210> SEQ ID NO 223
<211> LENGTH: 124
<212> TYPE: PRT
<213> ORGANISM: Artificial Sequence
<220> FEATURE:
<223> OTHER INFORMATION: Synthetic Construct

<400> SEQUENCE: 223

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120

<210> SEQ ID NO 224
<211> LENGTH: 107
<212> TYPE: PRT
<213> ORGANISM: Artificial Sequence
<220> FEATURE:
<223> OTHER INFORMATION: Synthetic Construct

<400> SEQUENCE: 224

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asp Leu
            20                  25                  30

Leu Ala Trp Tyr Gln Gln Lys Pro Gly Gln Ala Pro Arg Leu Leu Ile
        35                  40                  45

Tyr Asp Ala Phe Ser Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro

```
                    65                  70                  75                  80
Glu Asp Phe Ala Val Tyr Tyr Cys Gln Gln Tyr Gly Thr Pro Pro Ile
                    85                  90                  95

Thr Phe Gly Gln Gly Thr Arg Leu Glu Ile Lys
                100                 105

<210> SEQ ID NO 225
<211> LENGTH: 124
<212> TYPE: PRT
<213> ORGANISM: Artificial Sequence
<220> FEATURE:
<223> OTHER INFORMATION: Synthetic Construct

<400> SEQUENCE: 225

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Ser Ile Ser Gly Gly Gly Arg Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120

<210> SEQ ID NO 226
<211> LENGTH: 107
<212> TYPE: PRT
<213> ORGANISM: Artificial Sequence
<220> FEATURE:
<223> OTHER INFORMATION: Synthetic Construct

<400> SEQUENCE: 226

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ser Asp Leu
                20                  25                  30

Leu Ala Trp Tyr Gln Gln Lys Pro Gly Gln Ala Pro Arg Leu Leu Ile
            35                  40                  45

Tyr Asp Ala Tyr Ser Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ser Ala Ser Pro Ile
                85                  90                  95

Thr Phe Gly Gln Gly Thr Arg Leu Glu Ile Lys
            100                 105

<210> SEQ ID NO 227
<211> LENGTH: 124
<212> TYPE: PRT
<213> ORGANISM: Artificial Sequence
<220> FEATURE:
```

<223> OTHER INFORMATION: Synthetic Construct

<400> SEQUENCE: 227

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120

<210> SEQ ID NO 228
<211> LENGTH: 107
<212> TYPE: PRT
<213> ORGANISM: Artificial Sequence
<220> FEATURE:
<223> OTHER INFORMATION: Synthetic Construct

<400> SEQUENCE: 228

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Thr Phe Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Gly Ser Ser Pro Pro
                85                  90                  95

Thr Phe Gly Gln Gly Thr Arg Leu Glu Ile Lys
            100                 105

<210> SEQ ID NO 229
<211> LENGTH: 124
<212> TYPE: PRT
<213> ORGANISM: Artificial Sequence
<220> FEATURE:
<223> OTHER INFORMATION: Synthetic Construct

<400> SEQUENCE: 229

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Gly Gly Arg Ser Thr Tyr Tyr Ala Asp Ser Val

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Asp Leu Ser Pro Ser Asp Val Gly Trp Gly Tyr Gly Phe Asp
                100                 105                 110

Ile Trp Gly Gln Gly Thr Leu Val Thr Val Ser Ser
            115                 120
```

<210> SEQ ID NO 230
<211> LENGTH: 107
<212> TYPE: PRT
<213> ORGANISM: Artificial Sequence
<220> FEATURE:
<223> OTHER INFORMATION: Synthetic Construct

<400> SEQUENCE: 230

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Leu
                 20                  25                  30

Leu Ala Trp Tyr Gln Gln Lys Pro Gly Gln Ala Pro Arg Leu Leu Ile
             35                  40                  45

Tyr Asp Ala Tyr Thr Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Tyr Thr Gly Ser Pro Ile
                 85                  90                  95

Thr Phe Gly Gln Gly Thr Arg Leu Glu Ile Lys
                100                 105
```

<210> SEQ ID NO 231
<211> LENGTH: 124
<212> TYPE: PRT
<213> ORGANISM: Artificial Sequence
<220> FEATURE:
<223> OTHER INFORMATION: Synthetic Construct

<400> SEQUENCE: 231

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Asn Trp Val Arg Gln Ala Pro Gly Lys Gly Leu Glu Trp Val
             35                  40                  45

Ser Ala Ile Ser Gly Gly Gly Arg Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Ser Pro Ser Asp Val Gly Trp Gly Tyr Gly Phe Asp
                100                 105                 110

Ile Trp Gly Gln Gly Thr Leu Val Thr Val Ser Ser
            115                 120
```

```
<210> SEQ ID NO 232
<211> LENGTH: 107
<212> TYPE: PRT
<213> ORGANISM: Artificial Sequence
<220> FEATURE:
<223> OTHER INFORMATION: Synthetic Construct

<400> SEQUENCE: 232

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Leu
            20                  25                  30

Leu Ala Trp Tyr Gln Gln Lys Pro Gly Gln Ala Pro Arg Leu Leu Ile
        35                  40                  45

Tyr Asp Ala Tyr Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Thr Gly Ser Pro Ile
                85                  90                  95

Thr Phe Gly Gln Gly Thr Arg Leu Glu Ile Lys
            100                 105

<210> SEQ ID NO 233
<211> LENGTH: 124
<212> TYPE: PRT
<213> ORGANISM: Artificial Sequence
<220> FEATURE:
<223> OTHER INFORMATION: Synthetic Construct

<400> SEQUENCE: 233

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120

<210> SEQ ID NO 234
<211> LENGTH: 8
<212> TYPE: PRT
<213> ORGANISM: Artificial Sequence
<220> FEATURE:
<223> OTHER INFORMATION: Synthetic Construct

<400> SEQUENCE: 234

Lys Gln Ser Tyr Asp Leu Phe Thr
1               5
```

```
<210> SEQ ID NO 235
<211> LENGTH: 165
<212> TYPE: PRT
<213> ORGANISM: Homo sapiens

<400> SEQUENCE: 235

Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
            20                  25                  30

Ile Lys Cys Val Leu Ile Asn His Lys Asn Asn Asp Ser Ser Val Gly
        35                  40                  45

Lys Ser Ser Ser Tyr Pro Met Val Ser Glu Ser Pro Glu Asp Leu Gly
    50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
    130                 135                 140

Ile Gln Ser Glu Ala Thr Asn Tyr Thr Ile Leu Phe Thr Val Ser Ile
145                 150                 155                 160

Arg Asn Thr Leu Leu
                165

<210> SEQ ID NO 236
<211> LENGTH: 255
<212> TYPE: PRT
<213> ORGANISM: Homo sapiens

<400> SEQUENCE: 236

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
```

```
                    165                 170                 175
Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp
                245                 250                 255

<210> SEQ ID NO 237
<211> LENGTH: 255
<212> TYPE: PRT
<213> ORGANISM: Homo sapiens

<400> SEQUENCE: 237

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe
                245                 250                 255

<210> SEQ ID NO 238
<211> LENGTH: 255
<212> TYPE: PRT
<213> ORGANISM: Homo sapiens
```

<400> SEQUENCE: 238

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser
                245                 250                 255
```

<210> SEQ ID NO 239
<211> LENGTH: 255
<212> TYPE: PRT
<213> ORGANISM: Artificial Sequence
<220> FEATURE:
<223> OTHER INFORMATION: Synthetic Construct

<400> SEQUENCE: 239

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Arg Val Arg Cys Pro Arg Cys Pro Ala Pro
```

```
                100               105                110
Pro Val Ala Gly Pro Ser Val Phe Leu Phe Pro Lys Pro Lys Asp
            115                 120                 125
Thr Leu Met Ile Ser Arg Thr Pro Glu Val Thr Cys Val Val Ala
        130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ser Ser Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp
                245                 250                 255
```

<210> SEQ ID NO 240
<211> LENGTH: 255
<212> TYPE: DNA
<213> ORGANISM: Artificial Sequence
<220> FEATURE:
<223> OTHER INFORMATION: Synthetic Construct

<400> SEQUENCE: 240

```
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cggctgtcct acagtcctca     180
ggactctact ccctcagcag cgtagtgacc gtgccctcca gcaacttcgg cacccagacc     240
tacacctgca acgta                                                      255
```

<210> SEQ ID NO 241
<211> LENGTH: 255
<212> TYPE: PRT
<213> ORGANISM: Artificial Sequence
<220> FEATURE:
<223> OTHER INFORMATION: Synthetic Construct

<400> SEQUENCE: 241

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Glu Val Glu Cys Pro Glu Cys Pro Ala Pro
                100                 105                 110
```

```
Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Ala
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Glu Val Lys Gly Phe Tyr Pro Ser Asp
                245                 250                 255

<210> SEQ ID NO 242
<211> LENGTH: 255
<212> TYPE: DNA
<213> ORGANISM: Artificial Sequence
<220> FEATURE:
<223> OTHER INFORMATION: Synthetic Construct

<400> SEQUENCE: 242
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cggctgtcct acagtcctca     180
ggactctact ccctcagcag cgtagtgacc gtgccctcca gcaacttcgg cacccagacc     240
tacacctgca acgta                                                      255

<210> SEQ ID NO 243
<211> LENGTH: 107
<212> TYPE: PRT
<213> ORGANISM: Artificial Sequence
<220> FEATURE:
<223> OTHER INFORMATION: Synthetic Construct

<400> SEQUENCE: 243

Gly Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 244
<211> LENGTH: 255
<212> TYPE: DNA
<213> ORGANISM: Artificial Sequence
<220> FEATURE:
<223> OTHER INFORMATION: Synthetic Construct

<400> SEQUENCE: 244

```
ggaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctac                                                     255
```

<210> SEQ ID NO 245
<211> LENGTH: 14
<212> TYPE: PRT
<213> ORGANISM: Artificial Sequence
<220> FEATURE:
<223> OTHER INFORMATION: Synthetic Construct

<400> SEQUENCE: 245

```
Glu Gly Ile Gly Gly Asp Leu Arg Tyr Glu Gly Tyr Asp Ala
1               5                   10
```

<210> SEQ ID NO 246
<211> LENGTH: 10
<212> TYPE: PRT
<213> ORGANISM: Artificial Sequence
<220> FEATURE:
<223> OTHER INFORMATION: Synthetic Construct

<400> SEQUENCE: 246

```
Gly Gly Thr Phe Ser Ser Tyr Tyr Ile Thr
1               5                   10
```

<210> SEQ ID NO 247
<211> LENGTH: 5
<212> TYPE: PRT
<213> ORGANISM: Artificial Sequence
<220> FEATURE:
<223> OTHER INFORMATION: Synthetic Construct

<400> SEQUENCE: 247

```
Ser Tyr Tyr Ile Thr
1               5
```

<210> SEQ ID NO 248
<211> LENGTH: 17
<212> TYPE: PRT
<213> ORGANISM: Artificial Sequence
<220> FEATURE:
<223> OTHER INFORMATION: Synthetic Construct

<400> SEQUENCE: 248

```
Arg Ile Met Pro Ala Phe Gly Trp Thr Asn Tyr Ala Gln Lys Phe Gln
1               5                   10                  15

Gly
```

<210> SEQ ID NO 249
<211> LENGTH: 6
<212> TYPE: PRT
<213> ORGANISM: Artificial Sequence

```
<220> FEATURE:
<223> OTHER INFORMATION: Synthetic Construct

<400> SEQUENCE: 249

Met Pro Ala Phe Gly Trp
1               5

<210> SEQ ID NO 250
<211> LENGTH: 8
<212> TYPE: PRT
<213> ORGANISM: Artificial Sequence
<220> FEATURE:
<223> OTHER INFORMATION: Synthetic Construct

<400> SEQUENCE: 250

Asp Glu Phe Gly Ala Phe Asp Val
1               5

<210> SEQ ID NO 251
<211> LENGTH: 18
<212> TYPE: PRT
<213> ORGANISM: Artificial Sequence
<220> FEATURE:
<223> OTHER INFORMATION: Synthetic Construct

<400> SEQUENCE: 251

Gly Gly Ile Ile Pro Met Leu Gly Phe Ala Asn Tyr Ala Gln Lys Phe
1               5                   10                  15

Gln Gly

<210> SEQ ID NO 252
<211> LENGTH: 6
<212> TYPE: PRT
<213> ORGANISM: Artificial Sequence
<220> FEATURE:
<223> OTHER INFORMATION: Synthetic Construct

<400> SEQUENCE: 252

Ile Pro Ser Phe Gly Ala
1               5

<210> SEQ ID NO 253
<211> LENGTH: 17
<212> TYPE: PRT
<213> ORGANISM: Artificial Sequence
<220> FEATURE:
<223> OTHER INFORMATION: Synthetic Construct

<400> SEQUENCE: 253

Arg Ile Ile Pro Ser Phe Gly Ala Ala Asn Tyr Ala Gln Lys Phe Gln
1               5                   10                  15

Gly

<210> SEQ ID NO 254
<211> LENGTH: 12
<212> TYPE: PRT
<213> ORGANISM: Artificial Sequence
<220> FEATURE:
<223> OTHER INFORMATION: Synthetic Construct

<400> SEQUENCE: 254

Asp Asp Gly Glu Gly Trp Thr Pro Pro Phe Gly Tyr
1               5                   10

<210> SEQ ID NO 255
```

```
<211> LENGTH: 17
<212> TYPE: PRT
<213> ORGANISM: Artificial Sequence
<220> FEATURE:
<223> OTHER INFORMATION: Synthetic Construct

<400> SEQUENCE: 255

Ala Ile Ser Gly Gly Gly Arg Ser Thr Tyr Tyr Ala Asp Ser Val Lys
1               5                   10                  15
Gly

<210> SEQ ID NO 256
<211> LENGTH: 9
<212> TYPE: PRT
<213> ORGANISM: Artificial Sequence
<220> FEATURE:
<223> OTHER INFORMATION: Synthetic Construct

<400> SEQUENCE: 256

Gln Gln Tyr Gly Ser Glu Pro Tyr Thr
1               5

<210> SEQ ID NO 257
<211> LENGTH: 12
<212> TYPE: PRT
<213> ORGANISM: Artificial Sequence
<220> FEATURE:
<223> OTHER INFORMATION: Synthetic Construct

<400> SEQUENCE: 257

Arg Ala Ser Gln Ser Val Thr Ser Ser Gln Leu Ala
1               5                   10

<210> SEQ ID NO 258
<211> LENGTH: 10
<212> TYPE: PRT
<213> ORGANISM: Artificial Sequence
<220> FEATURE:
<223> OTHER INFORMATION: Synthetic Construct

<400> SEQUENCE: 258

Gln Gln Tyr Gly Ser Ser Leu Leu Ile Thr
1               5                   10

<210> SEQ ID NO 259
<211> LENGTH: 7
<212> TYPE: PRT
<213> ORGANISM: Artificial Sequence
<220> FEATURE:
<223> OTHER INFORMATION: Synthetic Construct

<400> SEQUENCE: 259

Asp Ala Tyr Thr Arg Ala Thr
1               5

<210> SEQ ID NO 260
<211> LENGTH: 8
<212> TYPE: PRT
<213> ORGANISM: Artificial Sequence
<220> FEATURE:
<223> OTHER INFORMATION: Synthetic Construct

<400> SEQUENCE: 260

Gln Gln Tyr Gly Ser Pro Tyr Thr
1               5
```

```
<210> SEQ ID NO 261
<211> LENGTH: 11
<212> TYPE: PRT
<213> ORGANISM: Artificial Sequence
<220> FEATURE:
<223> OTHER INFORMATION: Synthetic Construct

<400> SEQUENCE: 261

Arg Ala Ser Gln Asp Val Ser Asp Leu Leu Ala
1               5                   10

<210> SEQ ID NO 262
<211> LENGTH: 9
<212> TYPE: PRT
<213> ORGANISM: Artificial Sequence
<220> FEATURE:
<223> OTHER INFORMATION: Synthetic Construct

<400> SEQUENCE: 262

Gln Gln Tyr Ala Ser Ser Pro Ile Thr
1               5

<210> SEQ ID NO 263
<211> LENGTH: 11
<212> TYPE: PRT
<213> ORGANISM: Artificial Sequence
<220> FEATURE:
<223> OTHER INFORMATION: Synthetic Construct

<400> SEQUENCE: 263

Arg Ala Ser Gln Lys Val Ser Asp Leu Leu Ala
1               5                   10

<210> SEQ ID NO 264
<211> LENGTH: 9
<212> TYPE: PRT
<213> ORGANISM: Artificial Sequence
<220> FEATURE:
<223> OTHER INFORMATION: Synthetic Construct

<400> SEQUENCE: 264

Gln Gln Tyr Thr Gly Ser Pro Ile Thr
1               5

<210> SEQ ID NO 265
<211> LENGTH: 11
<212> TYPE: PRT
<213> ORGANISM: Artificial Sequence
<220> FEATURE:
<223> OTHER INFORMATION: Synthetic Construct

<400> SEQUENCE: 265

Arg Ala Ser Leu Ser Val Ser Asp Leu Leu Ala
1               5                   10

<210> SEQ ID NO 266
<211> LENGTH: 7
<212> TYPE: PRT
<213> ORGANISM: Artificial Sequence
<220> FEATURE:
<223> OTHER INFORMATION: Synthetic Construct

<400> SEQUENCE: 266

Asp Ala Tyr Ser Arg Ala Thr
1               5

<210> SEQ ID NO 267
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 267

Gln Gln Tyr Ser Ser Asn Pro Ile Thr
1               5

<210> SEQ ID NO 268
<211> LENGTH: 11
<212> TYPE: PRT
<213> ORGANISM: Artificial Sequence
<220> FEATURE:
<223> OTHER INFORMATION: Synthetic Construct

<400> SEQUENCE: 268

Arg Ala Ser Gly Ser Val Ser Asp Leu Leu Ala
1               5                   10

<210> SEQ ID NO 269
<211> LENGTH: 9
<212> TYPE: PRT
<213> ORGANISM: Artificial Sequence
<220> FEATURE:
<223> OTHER INFORMATION: Synthetic Construct

<400> SEQUENCE: 269

Gln Gln Tyr Ala Ser Tyr Pro Ile Thr
1               5

<210> SEQ ID NO 270
<211> LENGTH: 11
<212> TYPE: PRT
<213> ORGANISM: Artificial Sequence
<220> FEATURE:
<223> OTHER INFORMATION: Synthetic Construct

<400> SEQUENCE: 270

Arg Ala Ser Gln Ser Val Ser Asp Leu Leu Ala
1               5                   10

<210> SEQ ID NO 271
<211> LENGTH: 7
<212> TYPE: PRT
<213> ORGANISM: Artificial Sequence
<220> FEATURE:
<223> OTHER INFORMATION: Synthetic Construct

<400> SEQUENCE: 271

Asp Ala Phe Ser Arg Ala Thr
1               5

<210> SEQ ID NO 272
<211> LENGTH: 9
<212> TYPE: PRT
<213> ORGANISM: Artificial Sequence
<220> FEATURE:
<223> OTHER INFORMATION: Synthetic Construct

<400> SEQUENCE: 272

Gln Gln Tyr Gly Thr Pro Pro Ile Thr
1               5

<210> SEQ ID NO 273
<211> LENGTH: 11
```

<212> TYPE: PRT
<213> ORGANISM: Artificial Sequence
<220> FEATURE:
<223> OTHER INFORMATION: Synthetic Construct

<400> SEQUENCE: 273

Arg Ala Ser Glu Ser Val Ser Asp Leu Leu Ala
1               5                   10

<210> SEQ ID NO 274
<211> LENGTH: 9
<212> TYPE: PRT
<213> ORGANISM: Artificial Sequence
<220> FEATURE:
<223> OTHER INFORMATION: Synthetic Construct

<400> SEQUENCE: 274

Gln Gln Tyr Ser Ala Ser Pro Ile Thr
1               5

<210> SEQ ID NO 275
<211> LENGTH: 11
<212> TYPE: PRT
<213> ORGANISM: Artificial Sequence
<220> FEATURE:
<223> OTHER INFORMATION: Synthetic Construct

<400> SEQUENCE: 275

Arg Ala Ser Gln Ser Val Ser Ser Leu Leu Ala
1               5                   10

<210> SEQ ID NO 276
<211> LENGTH: 135
<212> TYPE: PRT
<213> ORGANISM: Artificial Sequence
<220> FEATURE:
<223> OTHER INFORMATION: Synthetic Construct

<400> SEQUENCE: 276

Asn Gln Asp Leu Pro Val Ile Lys Cys Val Leu Ile Asn His Lys Asn
1               5                   10                  15

Asn Asp Ser Ser Val Gly Lys Ser Ser Tyr Pro Met Val Ser Glu
            20                  25                  30

Ser Pro Glu Asp Leu Gly Cys Ala Leu Arg Pro Gln Ser Ser Gly Thr
        35                  40                  45

Val Tyr Glu Ala Ala Ala Val Glu Val Asp Ser Ala Ser Ile Thr
    50                  55                  60

Leu Gln Val Leu Val Asp Ala Pro Gly Asn Ile Ser Cys Leu Trp Val
65                  70                  75                  80

Phe Lys His Ser Ser Leu Asn Cys Gln Pro His Phe Asp Leu Gln Asn
                85                  90                  95

Arg Gly Val Val Ser Met Val Ile Leu Lys Met Thr Glu Thr Gln Ala
            100                 105                 110

Gly Glu Tyr Leu Leu Phe Ile Gln Ser Glu Ala Thr Asn Tyr Thr Ile
        115                 120                 125

Leu Phe Thr Val Ser Ile Arg
    130                 135

<210> SEQ ID NO 277
<211> LENGTH: 82
<212> TYPE: PRT
<213> ORGANISM: Artificial Sequence
<220> FEATURE:

<223> OTHER INFORMATION: Synthetic Construct

<400> SEQUENCE: 277

Asn Thr Leu Leu Tyr Leu Arg Arg Pro Tyr Phe Arg Lys Met Glu Asn
1               5                   10                  15

Gln Asp Ala Leu Val Cys Ile Ser Glu Ser Val Pro Glu Pro Ile Val
            20                  25                  30

Glu Trp Val Leu Cys Asp Ser Gln Gly Glu Ser Cys Lys Glu Glu Ser
        35                  40                  45

Pro Ala Val Val Lys Lys Glu Glu Lys Val Leu His Glu Leu Phe Gly
    50                  55                  60

Thr Asp Ile Arg Cys Cys Ala Arg Asn Glu Leu Gly Arg Glu Cys Thr
65                  70                  75                  80

Arg Leu

<210> SEQ ID NO 278
<211> LENGTH: 102
<212> TYPE: PRT
<213> ORGANISM: Artificial Sequence
<220> FEATURE:
<223> OTHER INFORMATION: Synthetic Construct

<400> SEQUENCE: 278

Phe Thr Ile Asp Leu Asn Gln Thr Pro Gln Thr Thr Leu Pro Gln Leu
1               5                   10                  15

Phe Leu Lys Val Gly Glu Pro Leu Trp Ile Arg Cys Lys Ala Val His
            20                  25                  30

Val Asn His Gly Phe Gly Leu Thr Trp Glu Leu Glu Asn Lys Ala Leu
        35                  40                  45

Glu Glu Gly Asn Tyr Phe Glu Met Ser Thr Tyr Ser Thr Asn Arg Thr
    50                  55                  60

Met Ile Arg Ile Leu Phe Ala Phe Val Ser Val Ala Arg Asn Asp
65                  70                  75                  80

Thr Gly Tyr Tyr Thr Cys Ser Ser Ser Lys His Pro Ser Gln Ser Ala
                85                  90                  95

Leu Val Thr Ile Val Glu
            100

<210> SEQ ID NO 279
<211> LENGTH: 88
<212> TYPE: PRT
<213> ORGANISM: Artificial Sequence
<220> FEATURE:
<223> OTHER INFORMATION: Synthetic Construct

<400> SEQUENCE: 279

Lys Gly Phe Ile Asn Ala Thr Asn Ser Ser Glu Asp Tyr Glu Ile Asp
1               5                   10                  15

Gln Tyr Glu Glu Phe Cys Phe Ser Val Arg Phe Lys Ala Tyr Pro Gln
            20                  25                  30

Ile Arg Cys Thr Trp Thr Phe Ser Arg Lys Ser Phe Pro Cys Glu Gln
        35                  40                  45

Lys Gly Leu Asp Asn Gly Tyr Ser Ile Ser Lys Phe Cys Asn His Lys
    50                  55                  60

His Gln Pro Gly Glu Tyr Ile Phe His Ala Glu Asn Asp Asp Ala Gln
65                  70                  75                  80

Phe Thr Lys Met Phe Thr Leu Asn
                85

<210> SEQ ID NO 280
<211> LENGTH: 107
<212> TYPE: PRT
<213> ORGANISM: Artificial Sequence
<220> FEATURE:
<223> OTHER INFORMATION: Synthetic Construct

<400> SEQUENCE: 280

```
Ile Arg Arg Lys Pro Gln Val Leu Ala Glu Ala Ser Ala Ser Gln Ala
1               5                   10                  15

Ser Cys Phe Ser Asp Gly Tyr Pro Leu Pro Ser Trp Thr Trp Lys Lys
            20                  25                  30

Cys Ser Asp Lys Ser Pro Asn Cys Thr Glu Ile Thr Glu Gly Val
        35                  40                  45

Trp Asn Arg Lys Ala Asn Arg Lys Val Phe Gly Gln Trp Val Ser Ser
    50                  55                  60

Ser Thr Leu Asn Met Ser Glu Ala Ile Lys Gly Phe Leu Val Lys Cys
65                  70                  75                  80

Cys Ala Tyr Asn Ser Leu Gly Thr Ser Cys Glu Thr Ile Leu Leu Asn
                85                  90                  95

Ser Pro Gly Pro Phe Pro Phe Ile Gln Asp Asn
            100                 105
```

<210> SEQ ID NO 281
<211> LENGTH: 112
<212> TYPE: PRT
<213> ORGANISM: Artificial Sequence
<220> FEATURE:
<223> OTHER INFORMATION: Synthetic Construct

<400> SEQUENCE: 281

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Val
            20                  25                  30

Arg Ser Arg Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asp Leu Phe Thr Phe Gly Ser Gly Thr Lys Leu Glu Ile Lys
            100                 105                 110
```

<210> SEQ ID NO 282
<211> LENGTH: 121
<212> TYPE: PRT
<213> ORGANISM: Artificial Sequence
<220> FEATURE:
<223> OTHER INFORMATION: Synthetic Construct

<400> SEQUENCE: 282

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30
```

```
Tyr Met Thr Trp Val Arg Gln Ala Pro Gly Lys Gly Leu Glu Trp Val
         35                  40                  45

Ala Phe Ile Arg Asn Arg Ala Arg Gly Tyr Thr Ser Asp His Asn Pro
 50                  55                  60

Ser Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                 85                  90                  95

Tyr Cys Ala Arg Asp Arg Pro Ser Tyr Tyr Val Leu Asp Tyr Trp Gly
                100                 105                 110

Gln Gly Thr Thr Val Thr Val Ser Ser
            115                 120

<210> SEQ ID NO 283
<211> LENGTH: 255
<212> TYPE: DNA
<213> ORGANISM: Artificial Sequence
<220> FEATURE:
<223> OTHER INFORMATION: Synthetic Construct

<400> SEQUENCE: 283
gacattgtga tgactcaatc ccccgactcc ctggctgtgt ccctcggcga acgcgcaact    60
atcaactgta aaagcagcca gtccctgttc aacgtccggt cgaggaagaa ctacctggcc   120
tggtatcagc agaaacctgg gcagccgccg aagcttctga tctcatgggc ctcaactcgg   180
gaaagcggag tgccagatag attctccgga tctggctccg gaaccgactt caccctgacg   240
atttcgagct gcaa                                                    255

<210> SEQ ID NO 284
<211> LENGTH: 255
<212> TYPE: DNA
<213> ORGANISM: Artificial Sequence
<220> FEATURE:
<223> OTHER INFORMATION: Synthetic Construct

<400> SEQUENCE: 284
gaagtccaac ttgtcgaatc gggaggaggc cttgtgcaac ccggtggatc cctgaggctg    60
tcatgcgcgg cctcgggctt cacctttttcc gattactaca tgacctgggt cagacaggcc   120
cctggaaagg ggttggaatg ggtggcattc atccggaata gagcccgcgg atacacttcc   180
gaccacaacc ccagcgtgaa ggggcggttc accattagcc gcgacaacgc caagaactcc   240
ctctacctcc aaatg                                                   255

<210> SEQ ID NO 285
<211> LENGTH: 6
<212> TYPE: PRT
<213> ORGANISM: Artificial Sequence
<220> FEATURE:
<223> OTHER INFORMATION: Synthetic Construct

<400> SEQUENCE: 285

Ser Asp Tyr Tyr Met Thr
 1               5

<210> SEQ ID NO 286
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 286

Gly Phe Thr Phe Ser Asp Tyr
1               5

<210> SEQ ID NO 287
<211> LENGTH: 10
<212> TYPE: PRT
<213> ORGANISM: Artificial Sequence
<220> FEATURE:
<223> OTHER INFORMATION: Synthetic Construct

<400> SEQUENCE: 287

Gly Phe Thr Phe Ser Asp Tyr Tyr Met Thr
1               5                   10

<210> SEQ ID NO 288
<211> LENGTH: 8
<212> TYPE: PRT
<213> ORGANISM: Artificial Sequence
<220> FEATURE:
<223> OTHER INFORMATION: Synthetic Construct

<400> SEQUENCE: 288

Arg Asn Arg Ala Arg Gly Tyr Thr
1               5

<210> SEQ ID NO 289
<211> LENGTH: 19
<212> TYPE: PRT
<213> ORGANISM: Artificial Sequence
<220> FEATURE:
<223> OTHER INFORMATION: Synthetic Construct

<400> SEQUENCE: 289

Phe Ile Arg Asn Arg Ala Arg Gly Tyr Thr Ser Asp His Asn Pro Ser
1               5                   10                  15

Val Lys Gly

<210> SEQ ID NO 290
<211> LENGTH: 10
<212> TYPE: PRT
<213> ORGANISM: Artificial Sequence
<220> FEATURE:
<223> OTHER INFORMATION: Synthetic Construct

<400> SEQUENCE: 290

Asp Arg Pro Ser Tyr Tyr Val Leu Asp Tyr
1               5                   10

<210> SEQ ID NO 291
<211> LENGTH: 17
<212> TYPE: PRT
<213> ORGANISM: Artificial Sequence
<220> FEATURE:
<223> OTHER INFORMATION: Synthetic Construct

<400> SEQUENCE: 291

Lys Ser Ser Gln Ser Leu Phe Asn Val Arg Ser Arg Lys Asn Tyr Leu
1               5                   10                  15

Ala

<210> SEQ ID NO 292
<211> LENGTH: 7
<212> TYPE: PRT
<213> ORGANISM: Artificial Sequence
```

```
<220> FEATURE:
<223> OTHER INFORMATION: Synthetic Construct

<400> SEQUENCE: 292

Trp Ala Ser Thr Arg Glu Ser
1               5

<210> SEQ ID NO 293
<211> LENGTH: 114
<212> TYPE: PRT
<213> ORGANISM: Homo sapiens

<400> SEQUENCE: 293

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser
```

ANTIBODIES SPECIFIC FOR FLT3 AND THEIR USES

This application is a divisional of U.S. patent application Ser. No. 15/993,874, filed May 31, 2018, now issued as U.S. Pat. No. 11,421,040, which claims the benefit of U.S. Provisional Application No. 62/514,574 filed Jun. 2, 2017, and U.S. Provisional Application No. 62/660,908 filed Apr. 20, 2018, the contents of which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC72360A_SEQListing_ST25. txt" created on May 22, 2018 and having a size of 141 KB. The sequence listing contained in this .txt file is part of the specification and is herein incorporated by reference in its entirety.

FIELD

The present invention relates to antibodies, e.g., full length antibodies or antigen binding fragments thereof, that specifically bind to Fms-Like Tyrosine Kinase 3 (FLT3). The invention further relates to heteromultimeric antibodies (e.g., bispecific antibodies) comprising FLT3 antibody on one arm. Compositions comprising the FLT3 antibodies, methods for producing and purifying such antibodies, and their use in diagnostics and therapeutics are also provided.

BACKGROUND

Flt3 (also known as CD135, FLK3, STK1), a well-characterized target antigen for Acute Myeloid Leukemia (AML), is over-expressed on AML patient blasts compared to healthy cells, and is expressed on the majority of patient cells (see, e.g., Carow et al, Blood: 87(3) (February 1996); and Birg et al., Blood: 80(10) (November 1992)). Further, Flt3 is the most frequently mutated gene in AML patients, and mutations resulting in constitutive activation of the receptor are associated with poor prognosis (see, e.g., Abu-Duhier et al. Br J Haematol., 111(1):190-5 (October 2000), Yamamoto et al., Blood: 97 (8) (April 2001)).

The presence of an oncogenic driver on the surface of leukemic blasts provides an opportunity for the development of a targeted therapy. Small-molecule Flt3 inhibitors have shown activity in clinical trials; however, the responses are usually transient due to the acquisition of resistance. Additionally, kinase inhibitors treat only a percentage of patients expressing the mutated form of Flt3, highlighting the urgent need for improved therapies.

Flt3 bispecific antibody in the form of T-cell engaging bispecific approach has also been developed recently since Flt3 has relatively low expression on tumor cells in comparison to other tumor antigens. However, a limitation of many bispecific formats is that they are of small molecular weight, and of short half-life, thus requiring continuous infusion. Accordingly, there remains a need for antibodies (e.g., monospecific or bispecific) treating cancer such as AML with improved efficacy and safety profile, and suitable for use with human patients.

SUMMARY

The invention disclosed herein is directed to antibodies (e.g., monospecific or bispecific antibodies) that specifically bind to Fms-Like Tyrosine Kinase 3 (FLT3). In particular, the inventors of the present invention have discovered that the FLT3 antibodies as described herein in the full-length bispecific format have longer half-life, minimized Fc-interaction, and minimized non-specific cytokine release in vivo via interaction with immune cells. Further, FLT3 antibodies targeting domain 4 of the FLT3 protein as described herein in the full-length bispecific format are found to be more effective at AML cell depletion compared to other domains, including domains 1, 2, 3, and 5 in the bispecific format noted.

Accordingly, in one aspect, the invention provides an isolated antibody which specifically binds to FLT3, wherein the antibody comprises (a) a heavy chain variable (VH) region comprising (i) a VH complementarity determining region one (CDR1) comprising the sequence shown in SEQ ID NO: 37, 38, 39, 43, 44, 45, 49, 50, 54, 55, 56, 60, 61, 62, 66, 67, 68, 72, 73, 74, 78, 79, 80, 84, 85, 86, 90, 91, 92, 96, 97, 98, 102, 103, 104, 108, 109, 110, 114, 115, 116, 120, 121, 122, 126, 127, 128, 132, 133, 134, 138, 139, 140, 246, or 247; (ii) a VH CDR2 comprising the sequence shown in SEQ ID NO: 40, 41, 46, 47, 51, 52, 57, 58, 63, 64, 69, 70, 75, 76, 81, 82, 87, 88, 93, 94, 99, 100, 105, 106, 111, 112, 117, 118, 123, 124, 129, 130, 135, 136, 141, 142, 248, 249, 251, 252, 253, or 255; and iii) a VH CDR3 comprising the sequence shown in SEQ ID NO: 42, 48, 53, 59, 65, 71, 77, 83, 89, 95, 101, 107, 113, 119, 125, 131, 137, 143, 245, 250, or 254; and/or a light chain variable (VL) region comprising (i) a VL CDR1 comprising the sequence shown in SEQ ID NO: 144, 147, 150, 153, 156, 159, 162, 165, 168, 171, 174, 177, 180, 183, 186, 189, 192, 195, 257, 261, 263, 265, 268, 270, 273, or 275; (ii) a VL CDR2 comprising the sequence shown in SEQ ID NO: 145, 148, 151, 154, 157, 160, 163, 166, 169, 172, 175, 178, 181, 184, 187, 190, 193, 196, 259, 266, or 271; and (iii) a VL CDR3 comprising the sequence shown in SEQ ID NO: 146, 149, 152, 155, 158, 161, 164, 167, 170, 173, 176, 179, 182, 185, 188, 191, 194, 197, 256, 258, 260, 262, 264, 267, 269, 272, or 274.

In another aspect, provided is an isolated antibody which specifically binds to FLT3, wherein the antibody comprises: a VH region comprising a VH CDR1, VH CDR2, and VH CDR3 of the VH sequence shown in SEQ ID NO: 2, 4, 6, 8, 10, 12, 14, 16, 18, 20, 22, 24, 26, 28, 30, 32, 34, 36, 205, 207, 209, 211, 213, 215, 217, 219, 221, 223, 225, 227, 229, 231, or 233; and/or a VL region comprising VL CDR1, VL CDR2, and VL CDR3 of the VL sequence shown in SEQ ID NO: 1, 3, 5, 7, 9, 11, 13, 15, 17, 19, 21, 23, 25, 27, 29, 31, 33, 35, 204, 206, 208, 210, 212, 214, 216, 218, 220, 222, 224, 226, 228, 230, or 232. In some embodiments, the antibody comprises: a VH region comprising a VH CDR1, VH CDR2, and VH CDR3 of the VH sequence shown in SEQ ID NO: 229; and/or a VL region comprising VL CDR1, VL CDR2, and VL CDR3 of the VL sequence shown in SEQ ID NO: 228. In some embodiments, the VH region as described herein comprises a variant with one or several conservative amino acid substitutions in residues that are not within a CDR and/or the VL region as described herein comprises a variant with one or several amino acid substitutions in amino acids that are not within a CDR. For example, in some embodiments, the VH or VL region can comprise an amino acid sequence described above or a variant thereof with no more than 10, 9, 8, 7, 6, 5, 4, 3, 2, or 1 conservative substitutions in residues that are not within a CDR.

In some embodiments, provided is an isolated antibody which specifically binds to FLT3, wherein the antibody comprises: a VH region comprising the sequence shown in SEQ ID NO: 215, 229, or 231; and/or a VL region comprising the sequence shown in SEQ ID NO: 214, 228, or 230. In some embodiments, provided is an isolated antibody which specifically binds to FLT3, wherein the antibody comprises: a VH region comprising the sequence shown in SEQ ID NO: 229; and/or a VL region comprising the sequence shown in SEQ ID NO: 228.

In some embodiments, provided is an antibody which specifically binds to FLT3 and competes with an isolated antibody provided herein which specifically binds to FLT3.

In another aspect, provided is a bispecific antibody wherein the bispecific antibody is a full-length antibody, comprising a first antibody variable domain of the bispecific antibody specifically binding to a target antigen, and comprising a second antibody variable domain of the bispecific antibody capable of recruiting the activity of a human immune effector cell by specifically binding to an effector antigen located on the human immune effector cell, wherein the first antibody variable domain binds to domain 4 of FLT3 comprising SEQ ID NO: 279 or domain 5 of FLT3 comprising SEQ ID NO: 280.

In another aspect, provided is a bispecific antibody wherein the bispecific antibody is a full-length antibody, comprising a first antibody variable domain of the bispecific antibody specifically binding to a target antigen (e.g., FLT3), and comprising a second antibody variable domain of the bispecific antibody capable of recruiting the activity of a human immune effector cell by specifically binding to an effector antigen (e.g., Cluster of differentiation 3 (CD3)) located on the human immune effector cell. In some embodiments, the first antibody variable domain comprises a heavy chain variable (VH) region comprising a VH CDR1, VH CDR2, and VH CDR3 of the VH sequence shown in SEQ ID NO: 2, 4, 6, 8, 10, 12, 14, 16, 18, 20, 22, 24, 26, 28, 30, 32, 34, 36, 205, 207, 209, 211, 213, 215, 217, 219, 221, 223, 225, 227, 229, 231, or 233; and/or a light chain variable (VL) region comprising VL CDR1, VL CDR2, and VL CDR3 of the VL sequence shown in SEQ ID NO: 1, 3, 5, 7, 9, 11, 13, 15, 17, 19, 21, 23, 25, 27, 29, 31, 33, 35, 204, 206, 208, 210, 212, 214, 216, 218, 220, 222, 224, 226, 228, 230, or 232. In some embodiments, the first antibody variable domain comprises (a) a heavy chain variable (VH) region comprising (i) a VH complementarity determining region one (CDR1) comprising the sequence shown in SEQ ID NO: 37, 38, 39, 43, 44, 45, 49, 50, 54, 55, 56, 60, 61, 62, 66, 67, 68, 72, 73, 74, 78, 79, 80, 84, 85, 86, 90, 91, 92, 96, 97, 98, 102, 103, 104, 108, 109, 110, 114, 115, 116, 120, 121, 122, 126, 127, 128, 132, 133, 134, 138, 139, 140, 246, or 247; (ii) a VH CDR2 comprising the sequence shown in SEQ ID NO: 40, 41, 46, 47, 51, 52, 57, 58, 63, 64, 69, 70, 75, 76, 81, 82, 87, 88, 93, 94, 99, 100, 105, 106, 111, 112, 117, 118, 123, 124, 129, 130, 135, 136, 141, 142, 248, 249, 251, 252, 253, or 255; and iii) a VH CDR3 comprising the sequence shown in SEQ ID NO: 42, 48, 53, 59, 65, 71, 77, 83, 89, 95, 101, 107, 113, 119, 125, 131, 137, 143, 245, 250, or 254; and/or (b) a light chain variable (VL) region comprising (i) a VL CDR1 comprising the sequence shown in SEQ ID NO: 144, 147, 150, 153, 156, 159, 162, 165, 168, 171, 174, 177, 180, 183, 186, 189, 192, 195, 257, 261, 263, 265, 268, 270, 273, or 275; (ii) a VL CDR2 comprising the sequence shown in SEQ ID NO: 145, 148, 151, 154, 157, 160, 163, 166, 169, 172, 175, 178, 181, 184, 187, 190, 193, 196, 259, 266, or 271; and (iii) a VL CDR3 comprising the sequence shown in SEQ ID NO: 146, 149, 152, 155, 158, 161, 164, 167, 170, 173, 176, 179, 182, 185, 188, 191, 194, 197, 256, 258, 260, 262, 264, 267, 269, 272, or 274.

In some embodiments, the second antibody variable domain comprises the VH and/or VL region specific against CD3. For example, the second antibody variable domain comprises a heavy chain variable (VH) region comprising a VH CDR1, VH CDR2, and VH CDR3 of the VH sequence shown in SEQ ID NO:282; and/or a light chain variable (VL) region comprising a VL CDR1, VL CDR2, and VL CDR3 of the VL sequence shown in SEQ ID NO: 281.

In some embodiments, the first antibody variable domain comprises a heavy chain variable (VH) region comprising a VH CDR1, VH CDR2, and VH CDR3 of the VH sequence shown in SEQ ID NO: 229; and/or a light chain variable (VL) region comprising VL CDR1, VL CDR2, and VL CDR3 of the VL sequence shown in SEQ ID NO: 228; and a second antibody variable domain comprising a heavy chain variable (VH) region comprising a VH CDR1, VH CDR2, and VH CDR3 of the VH sequence shown in SEQ ID NO:282; and/or a light chain variable (VL) region comprising a VL CDR1, VL CDR2, and VL CDR3 of the VL sequence shown in SEQ ID NO: 281.

In some embodiments, the second antibody variable domain comprises (a) a VH region comprising (i) a VH CDR1 comprising the sequence shown in SEQ ID NO: 285, 286, or 287; (ii) a VH CDR2 comprising the sequence shown in SEQ ID NO: 288 or 289; and iii) a VH CDR3 comprising the sequence shown in SEQ ID NO: 290; and/or a VL region comprising (i) a VL CDR1 comprising the sequence shown in SEQ ID NO: 291; (ii) a VL CDR2 comprising the sequence shown in SEQ ID NO: 292; and (iii) a VL CDR3 comprising the sequence shown in SEQ ID NO: 234.

In some embodiments, the antibodies described herein comprise a constant region. In some embodiments, the antibodies described herein are of the human IgG1, IgG2 or IgG2Δa, IgG3, or IgG4 subclass. In some embodiments, the antibodies described herein comprise a glycosylated constant region. In some embodiments, the antibodies described herein comprise a constant region having decreased binding affinity to one or more human Fc gamma receptor(s).

In some embodiments, both the first and the second antibody variable domains of the bispecific antibody comprise amino acid modifications at positions 223, 225, and 228 (e.g., (C223E or C223R), (E225R), and (P228E or P228R)) in the hinge region and at position 409 or 368 (e.g., K409R or L368E (EU numbering scheme)) in the CH3 region of human IgG2 (SEQ ID NO: 290).

In some embodiments, both the first and the second antibody variable domains of the bispecific antibody comprise amino acid modifications at position 265 (e.g., D265A) of the human IgG2.

In some embodiments, both the first and the second antibody variable domains of the bispecific antibody comprise amino acid modifications at one or more of positions 265 (e.g., D265A), 330 (e.g., A330S), and 331 (e.g., P331S) of the human IgG2. In some embodiments, both the first and the second antibody variable domains of the bispecific antibody comprise amino acid modifications at each of positions 265 (e.g., D265A), 330 (e.g., A330S), and 331 (e.g., P331S) of the human IgG2.

In other embodiments, the invention provides pharmaceutical compositions comprising any of the antibodies described herein.

The invention also provides cell lines that recombinantly produce any of the antibodies described herein.

The invention also provides nucleic acids encoding any of the antibodies described herein. The invention also provides nucleic acids encoding a heavy chain variable region and/or a light chain variable region of any of the antibodies described herein.

The invention also provides a host cell comprising a nucleic acid or vector provided herein. Also provided is a method of producing an antibody (e.g. monospecific or bispecific) provided herein, comprising culturing a host cell provided herein under conditions that result in production of the antibody, and isolating the antibody from the host cell or culture.

The invention also provides kits comprising an effective amount of any of the antibodies or antibody conjugates described herein.

Also provided is an antibody or bispecific antibody provided herein for use as a medicament.

The invention also provides methods of treating subjects in need thereof comprising providing the isolated antibodies or bispecific antibodies described herein, and administering said antibodies to said subject.

Also provided are methods of treating a condition associated with malignant cells expressing FLT3 in a subject comprising administering to a subject in need thereof an effective amount of a pharmaceutical composition comprising the antibodies as described herein. In some embodiments, the condition is a cancer. In some embodiments, the cancer is an FLT3 related cancer (e.g., any cancer with FLT3 expression) selected from the group consisting of multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other hematopoietic cells related cancer.

In another aspect, the invention provides a method of inhibiting tumor growth or progression in a subject who has malignant cells expressing FLT3, comprising administering to the subject in need thereof an effective amount of a pharmaceutical composition comprising the isolated antibodies or bispecific antibodies, as described herein.

In another aspect, the invention provides a method of inhibiting metastasis of malignant cells expressing FLT3 in a subject, comprising administering to the subject in need thereof an effective amount of the pharmaceutical composition comprising the isolated antibodies or bispecific antibodies, as described herein.

In another aspect, the invention provides a method of inducing tumor regression in a subject who has malignant cells expressing FLT3, comprising administering to the subject in need thereof an effective amount of the pharmaceutical composition of a pharmaceutical composition comprising the isolated antibodies or bispecific antibodies, as described herein.

In some embodiments, the methods as described herein further comprise administering an effective amount of a second therapeutic agent. In some embodiments, the second therapeutic agent is a biotherapeutic agent, for example, an antibody.

In some embodiments, the second therapeutic agent is a cytokine, TNFα (Tumor Necrosis Factor alpha), a PAP (phosphatidic acid phosphatase) inhibitor, an oncolytic virus, a kinase inhibitor, an IDO (Indoleamine-pyrrole 2,3-dioxygenase) inhibitor, a glutaminase GLS1 inhibitor, a CAR (Chimeric Antigen Receptor)-T cell or T cell therapy, a TLR (Toll-Like Receptor) Agonist (e.g., TLR3, TLR4, TLR5, TLR7, TLR9), or a tumor vaccine. In some embodiments, the cytokine is IL-15 (Interleukin-15).

BRIEF DESCRIPTION OF THE FIGURES/DRAWINGS

Figure 4A:
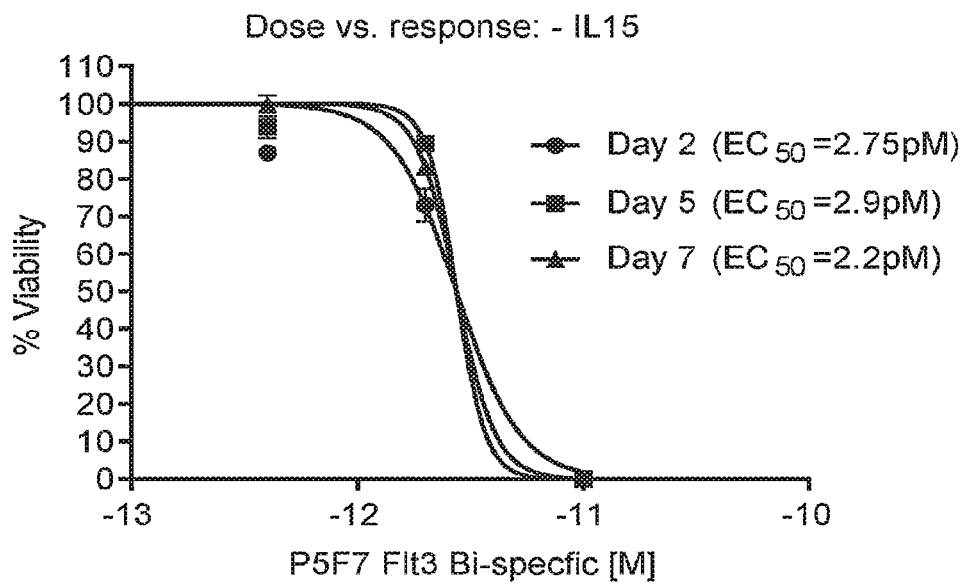
Figure 4B:
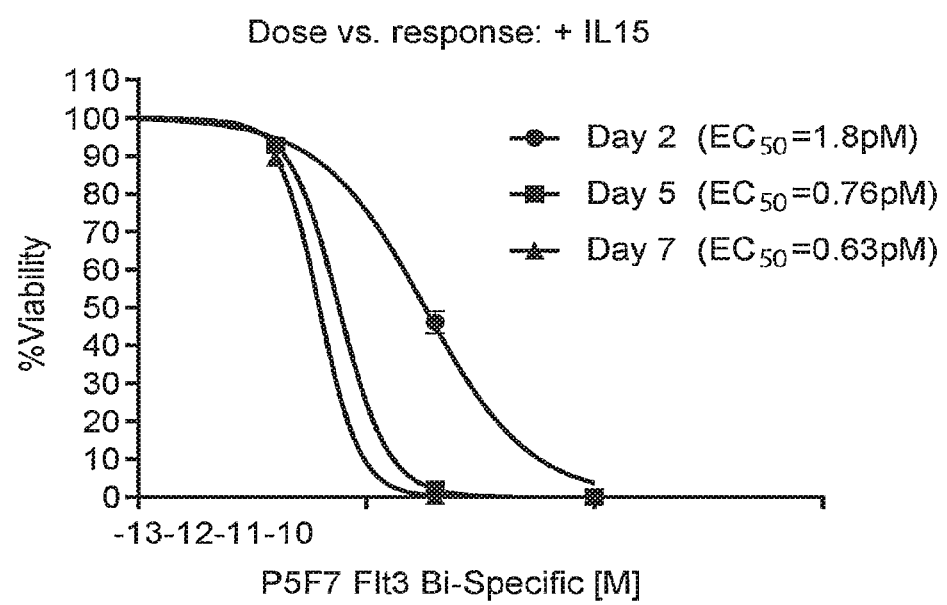
Figure 5A:
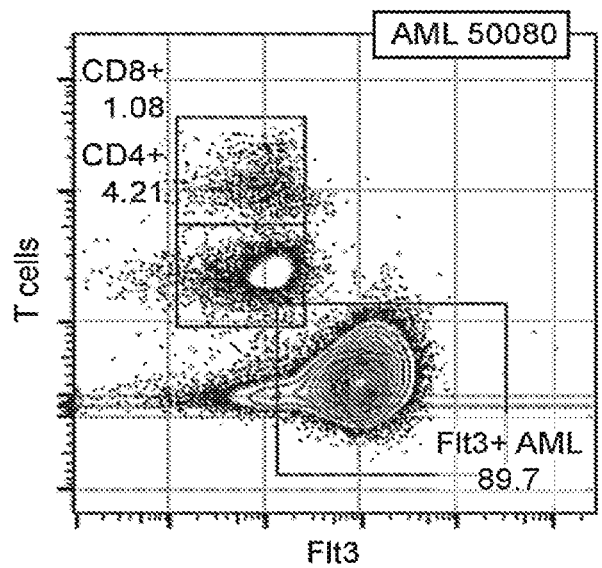
Figure 5B:
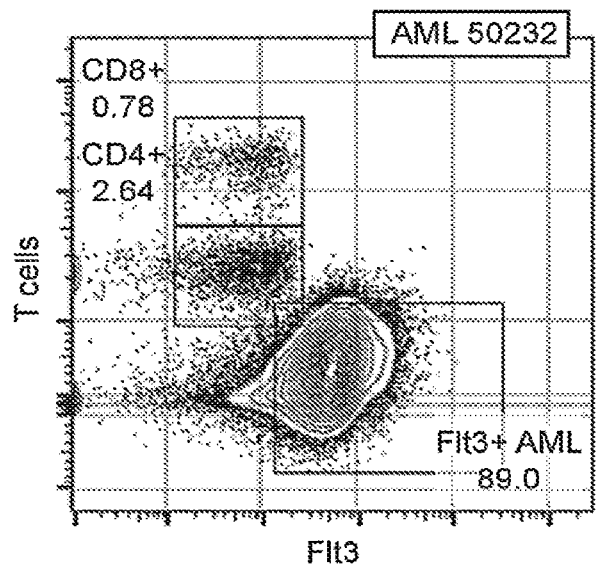
Figure 5C:
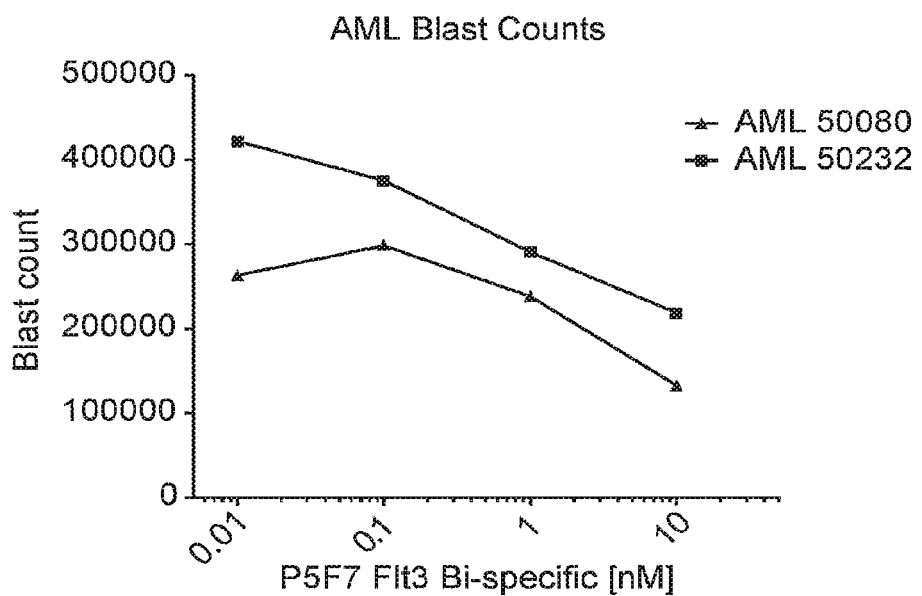
Figure 5D:
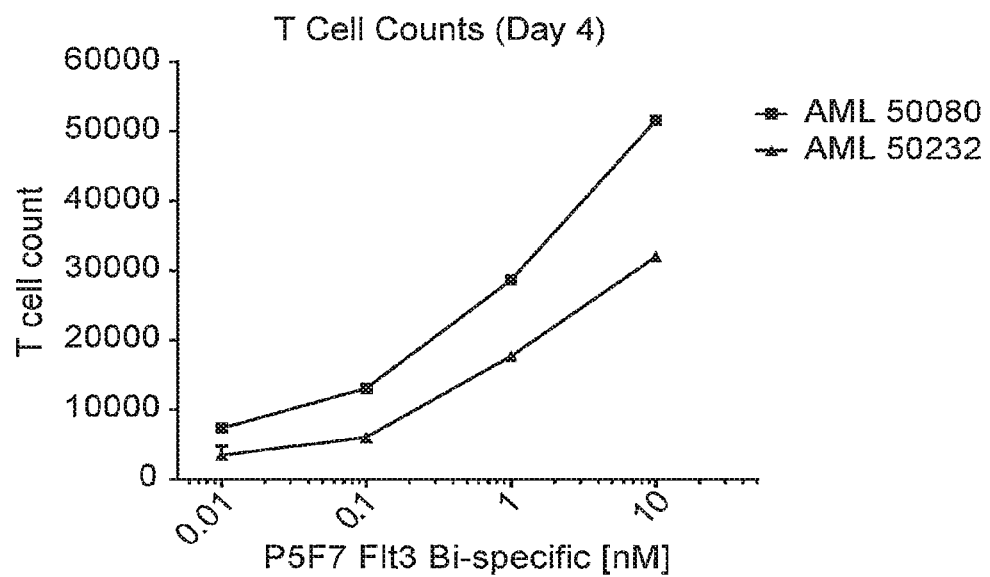
Figure 5E:
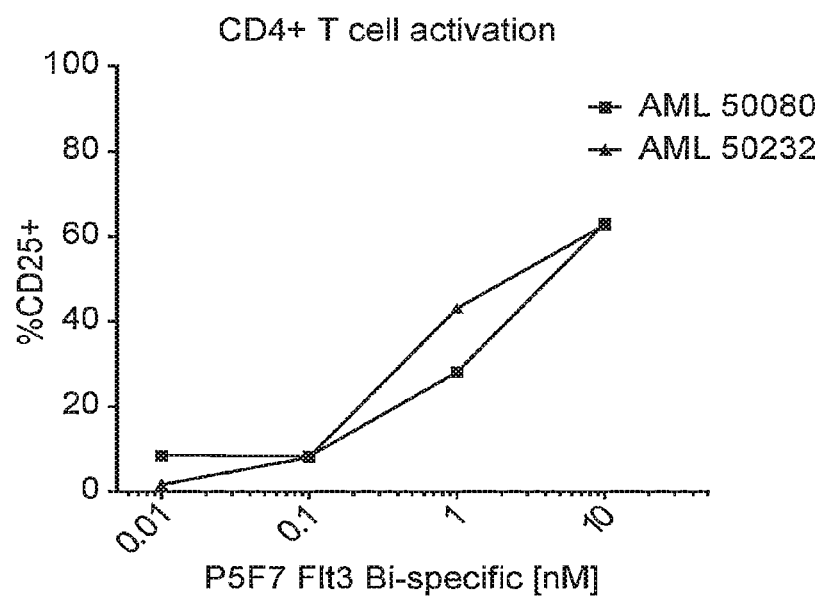
Figure 5F:
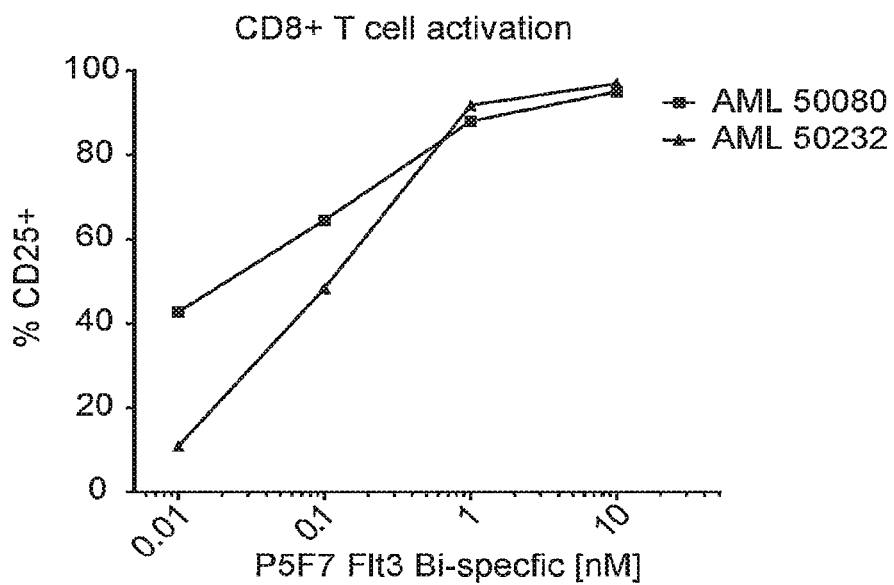

FIG. 4A and FIG. 4B demonstrate decreased $EC_{50}$ values for the FLT3/CD3 bispecific antibody (P5F7) in the absence or presence of IL15, respectively.

FIGS. 5A, 5B, 5C, 5D, 5E, and 5F demonstrate the killing of two primary AML samples in bone marrow aspirates ex vivo induced by increasing concentrations of FLT3/CD3 bispecific (P5F7) in the presence of autologous T cells. A concentration-dependent increase in total T cells and activated T cells, as determined by percent CD25+ cells, is depicted.

DETAILED DESCRIPTION

The invention disclosed herein provides antibodies (e.g., monospecific or bispecific) that specifically bind to FLT3 (e.g., human FLT3). The invention also provides polynucleotides encoding these antibodies, compositions comprising these antibodies, and methods of making and using these antibodies. The invention also provides methods for treating a condition associated with FLT3-mediated pathologies in a subject, such as cancer. In particular, the inventors of the present invention have discovered that the FLT3 antibodies as described herein in the full-length bispecific format have longer half-life, minimized Fc-interaction, and minimized non-specific cytokine release in vivo via interaction with the immune cells. Further, the FLT3 antibodies targeting domain 4 of the FLT3 protein as described herein in the full-length bispecific format are found to be more effective at AML cell depletion compared to other domains, including domains 1, 2, 3, and 5 in the bispecific format.

General Techniques

The practice of the present invention will employ, unless otherwise indicated, conventional techniques of molecular biology (including recombinant techniques), microbiology, cell biology, biochemistry, immunology, virology, monoclonal antibody generation and engineering, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also antigen binding fragments thereof (such as Fab, Fab', F(ab')$_2$, Fv), single chain (ScFv) and domain antibodies (including, for example, shark and camelid antibodies), and fusion proteins comprising an antibody, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding fragment" or "antigen binding portion" of an antibody, as used herein, refers to one or more fragments of an intact antibody that retain the ability to specifically bind to a given antigen (e.g., FLT3). Antigen binding functions of an antibody can be performed by fragments of an intact antibody. Examples of binding fragments encompassed within the term "antigen binding fragment" of an antibody include Fab; Fab'; F(ab')$_2$; an Fd fragment consisting of the VH and CH1 domains; an Fv fragment consisting of the VL and VH domains of a single arm of an antibody; a single domain antibody (dAb) fragment (Ward et al., Nature 341:544-546, 1989), and an isolated complementarity determining region (CDR).

An antibody or a polypeptide that "preferentially binds" or "specifically binds" (used interchangeably herein) to a target (e.g., FLT3 protein) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an FLT3 epitope is an antibody that binds this epitope with greater affinity, avidity, more readily, and/or with greater duration than it binds to other FLT3 epitopes or non-FLT3 epitopes. It is also understood that by reading this definition, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda MD)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256:495, 1975, or may be made by recombinant DNA methods such as described in U.S. Pat. No. 4,816,567. The monoclonal antibodies may also be isolated from phage libraries generated using the techniques described in McCafferty et al., Nature 348:552-554, 1990, for example.

As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., Nature Biotechnology, 14:309-314, 1996; Sheets et al., Proc. Natl. Acad. Sci. (USA) 95:6157-6162, 1998; Hoogenboom and Winter, J. Mol. Biol., 227:381, 1991; Marks et al., J. Mol. Biol., 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boerner et al., J. Immunol., 147 (1):86-95, 1991; and U.S. Pat. No. 5,750,373.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The terms "polypeptide", "oligopeptide", "peptide" and "protein" are used interchangeably herein to refer to chains of amino acids of any length. For example, the chain may be relatively short (e.g., 10-100 amino acids), or longer. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

A "monovalent antibody" comprises one antigen binding site per molecule (e.g., IgG or Fab). In some instances, a monovalent antibody can have more than one antigen binding sites, but the binding sites are from different antigens.

A "monospecific antibody" comprises two identical antigen binding sites per molecule (e.g. IgG) such that the two binding sites bind identical epitope on the antigen. Thus, they compete with each other on binding to one antigen molecule. Most antibodies found in nature are monospecific. In some instances, a monospecific antibody can also be a monovalent antibody (e.g. Fab)

A "bivalent antibody" comprises two antigen binding sites per molecule (e.g., IgG). In some instances, the two binding sites have the same antigen specificities. However, bivalent antibodies may be bispecific.

A "bispecific" or "dual-specific" is a hybrid antibody having two different antigen binding sites. The two antigen binding sites of a bispecific antibody bind to two different epitopes, which may reside on the same or different protein targets.

A "bifunctional" is antibody is an antibody having identical antigen binding sites (i.e., identical amino acid sequences) in the two arms but each binding site can recognize two different antigens.

A "heteromultimer", "heteromultimeric complex", or "heteromultimeric polypeptide" is a molecule comprising at least a first polypeptide and a second polypeptide, wherein the second polypeptide differs in amino acid sequence from the first polypeptide by at least one amino acid residue. The heteromultimer can comprise a "heterodimer" formed by the first and second polypeptide or can form higher order tertiary structures where polypeptides in addition to the first and second polypeptide are present.

A "heterodimer," "heterodimeric protein," "heterodimeric complex," or "heteromultimeric polypeptide" is a molecule comprising a first polypeptide and a second polypeptide, wherein the second polypeptide differs in amino acid sequence from the first polypeptide by at least one amino acid residue.

The "hinge region," "hinge sequence", and variations thereof, as used herein, includes the meaning known in the art, which is illustrated in, for example, Janeway et al., ImmunoBiology: the immune system in health and disease, (Elsevier Science Ltd., NY) (4th ed., 1999); Bloom et al., *Protein Science* (1997), 6:407-415; Humphreys et al., *J. Immunol. Methods* (1997), 209:193-202.

The "immunoglobulin-like hinge region," "immunoglobulin-like hinge sequence," and variations thereof, as used herein, refer to the hinge region and hinge sequence of an immunoglobulin-like or an antibody-like molecule (e.g., immunoadhesins). In some embodiments, the immunoglobulin-like hinge region can be from or derived from any IgG1, IgG2, IgG3, or IgG4 subtype, or from IgA, IgE, IgD or IgM, including chimeric forms thereof, e.g., a chimeric IgG1/2 hinge region.

The term "immune effector cell" or "effector cell as used herein refers to a cell within the natural repertoire of cells in the human immune system which can be activated to affect the viability of a target cell. The viability of a target cell can include cell survival, proliferation, and/or ability to interact with other cells.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007).

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As known in the art, a "constant region" of an antibody refers to the constant region of the antibody light chain or the constant region of the antibody heavy chain, either alone or in combination.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant regions, CH2 and CH3.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Ann. Rev. Immunol., 9:457-92, 1991; Capel et al., Immunomethods, 4:25-34, 1994; and de Haas et al., J. Lab. Clin. Med., 126:330-41, 1995. "FcR" also includes the neonatal receptor, FcRn, which is responsible for the transfer of maternal IgGs to the fetus (Guyer et al., J. Immunol., 117:587, 1976; and Kim et al., J. Immunol., 24:249, 1994).

The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

The term "effector function" refers to the biological activities attributable to the Fc region of an antibody. Examples of antibody effector functions include, but are not limited to, antibody-dependent cell-mediated cytotoxicity (ADCC), Fc receptor binding, complement dependent cytotoxicity (CDC), phagocytosis, C1q binding, and down regulation of cell surface receptors (e.g., B cell receptor; BCR). See, e.g., U.S. Pat No. 6,737,056. Such effector functions generally require the Fc region to be combined with a binding domain (e.g., an antibody variable domain) and can be assessed using various assays known in the art for evaluating such antibody effector functions. An exemplary measurement of effector function is through Fcγ3 and/or C1q binding.

As used herein "antibody-dependent cell-mediated cytotoxicity" or "ADCC" refers to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, *PNAS (USA)*, 95:652-656.

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g.

as described in Gazzano-Santoro et al., *J. Immunol. Methods,* 202: 163 (1996), may be performed.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of FLT3 expressing tumor, remission of an FLT3 associated disease (e.g., cancer), decreasing symptoms resulting from an FLT3 associated disease (e.g., cancer), increasing the quality of life of those suffering from an FLT3 associated disease (e.g., cancer), decreasing the dose of other medications required to treat an FLT3 associated disease (e.g., cancer), delaying the progression of an FLT3 associated disease (e.g., cancer), curing an FLT3 associated disease (e.g., cancer), and/or prolong survival of patients having an FLT3 associated disease (e.g., cancer).

"Ameliorating" means a lessening or improvement of one or more symptoms as compared to not administering an FLT3 antibody (monospecific or bispecific). "Ameliorating" also includes shortening or reduction in duration of a symptom.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various FLT3 associated diseases or conditions (such as for example multiple myeloma), decreasing the dose of other medications required to treat the disease, enhancing the effect of another medication, and/or delaying the progression of the FLT3 associated disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, PA, 1990; and Remington, The Science and Practice of Pharmacy 21st Ed. Mack Publishing, 2005).

The term "acyl donor glutamine-containing tag" or "glutamine tag" as used herein refers to a polypeptide or a protein containing one or more Gln residue(s) that acts as a transglutaminase amine acceptor. See, e.g., WO2012059882 and WO2015015448.

The term "$k_{on}$" or "$k_a$", as used herein, refers to the rate constant for association of an antibody to an antigen. Specifically, the rate constants ($k_{on}/k_a$ and $k_{off}/k_d$) and equilibrium dissociation constants are measured using whole antibody (i.e. bivalent) and monomeric FLT3 proteins (e.g., Histidine-tagged FLT3 fusion protein).

The term "$k_{off}$" or "$k_d$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range. Generally speaking, the term "about" refers to the indicated value of the variable and to all values of the variable that are within the experimental error of the indicated value (e.g. within the 95% confidence interval for the mean) or within 10 percent of the indicated value, whichever is greater. Where the term "about" is used within the context of a time period (years, months, weeks, days etc.), the term "about" means that period of time plus or minus one amount of the next subordinate time period (e.g. about 1 year means 11-13 months; about 6 months means 6 months plus or minus 1 week; about 1 week means 6-8 days; etc.), or within 10 percent of the indicated value, whichever is greater.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the present invention. The materials, methods, and examples are illustrative only and not intended to be limiting.

FLT3 Antibodies and Methods of Making Thereof

The present invention provides an antibody that binds to FLT3 [e.g., human FLT3 (e.g., accession number: NP_004110 or SEQ ID NO: 235)] and characterized by any one or more of the following characteristics: (a) treat, prevent, ameliorate one or more symptoms of a condition associated with malignant cells expressing FLT3 in a subject (e.g., cancer such as AML); (b) inhibit tumor growth or progression in a subject (who has a malignant tumor expressing FLT3); (c) inhibit metastasis of cancer (malignant) cells expressing FLT3 in a subject (who has one or more malignant cells expressing FLT3); (d) induce regression (e.g., long-term regression) of a tumor expressing FLT3; (e) exert cytotoxic activity in malignant cells expressing FLT3; (f) block FLT3 interaction with other yet to be identified factors; and/or (g) induce bystander effect that kill or inhibit growth of non-FLT3 expressing malignant cells in the vicinity.

In one aspect, provided is an isolated antibody which specifically binds to FLT3, wherein the antibody comprises (a) a heavy chain variable (VH) region comprising (i) a VH complementarity determining region one (CDR1) comprising the sequence shown in 37, 38, 39, 43, 44, 45, 49, 50, 54, 55, 56, 60, 61, 62, 66, 67, 68, 72, 73, 74, 78, 79, 80, 84, 85, 86, 90, 91, 92, 96, 97, 98, 102, 103, 104, 108, 109, 110, 114, 115, 116, 120, 121, 122, 126, 127, 128, 132, 133, 134, 138, 139, 140, 246, or 247; (ii) a VH CDR2 comprising the sequence shown in SEQ ID NO: 40, 41, 46, 47, 51, 52, 57, 58, 63, 64, 69, 70, 75, 76, 81, 82, 87, 88, 93, 94, 99, 100, 105, 106, 111, 112, 117, 118, 123, 124, 129, 130, 135, 136, 141, 142, 248, 249, 251, 252, 253, or 255; and iii) a VH CDR3 comprising the sequence shown in SEQ ID NO: 42, 48, 53, 59, 65, 71, 77, 83, 89, 95, 101, 107, 113, 119, 125, 131, 137, 143, 245, 250, or 254; and/or a light chain variable (VL) region comprising (i) a VL CDR1 comprising the sequence shown in SEQ ID NO: 144, 147, 150, 153, 156, 159, 162, 165, 168, 171, 174, 177, 180, 183, 186, 189, 192, 195, 257, 261, 263, 265, 268, 270, 273, or 275; (ii) a VL CDR2 comprising the sequence shown in SEQ ID NO: 145, 148, 151, 154, 157, 160, 163, 166, 169, 172, 175, 178, 181, 184, 187, 190, 193, 196, 259, 266, or 271; and (iii) a VL CDR3 comprising the sequence shown in SEQ ID NO: 146, 149, 152, 155, 158, 161, 164, 167, 170, 173, 176, 179, 182, 185, 188, 191, 194, 197, 256, 258, 260, 262, 264, 267, 269, 272, or 274.

In another aspect, provided is an isolated antibody which specifically binds to FLT3, wherein the antibody comprises: a VH region comprising a VH CDR1, VH CDR2, and VH CDR3 of the VH sequence shown in SEQ ID NO: 2, 4, 6, 8, 10, 12, 14, 16, 18, 20, 22, 24, 26, 28, 30, 32, 34, 36, 205, 207, 209, 211, 213, 215, 217, 219, 221, 223, 225, 227, 229, 231, or 233; and/or a VL region comprising VL CDR1, VL CDR2, and VL CDR3 of the VL sequence shown in SEQ ID NO: 1, 3, 5, 7, 9, 11, 13, 15, 17, 19, 21, 23, 25, 27, 29, 31, 33, 35, 204, 206, 208, 210, 212, 214, 216, 218, 220, 222, 224, 226, 228, 230, or 232. In some embodiments, the antibody comprises: a VH region comprising a VH CDR1, VH CDR2, and VH CDR3 of the VH sequence shown in SEQ ID NO. 229; and/or a VL region comprising VL CDR1, VL CDR2, and VL CDR3 of the VL sequence shown in SEQ ID NO: 228.

In some embodiments, provided is an antibody having any one of partial light chain sequence as listed in Table 1 and/or any one of partial heavy chain sequence as listed in Table 1. In Table 1, the underlined sequences are CDR sequences according to Kabat and in bold according to Chothia, except for the heavy chain CDR2 sequences of P4F6, P4C7, P3A1, P5A3, P9B5, P9F1, P1B4, P1B11, P7H3, P3E10, P1A5, P5F7, P4H11, P15F7, P12B6, P8B6, P14G2, and P7F9, the Chothia CDR sequence is underlined and the Kabat CDR sequence is in bold.

TABLE 1

| mAb | Light Chain | Heavy Chain |
| --- | --- | --- |
| P4F6 | EIVLTQSPGTLSLSPGERATLSCR ASHSVSSSYLAWYQQKPGQAPR LLIYGASSRATGIPDRFSGSGSG TDFTLTISRLEPEDFAVYYCQQY GSPPRTFGQGTKVEIK (SEQ ID NO: 1) | QVQLVQSGAEVKKPGSSVKVSCK ASGGTFGSYGISWVRQAPGQGLE WMGIIPIFGTVTYAQKFQGRVTIT ADESTRTAYMELSSLRSEDTAVYY CARDSWSGATGASDTWGQGTLV TVSS (SEQ ID NO: 2) |
| P4C7 | EIVLTQSPGTLSLSPGERATLSCR ASQYVSASLLAWYQQKPGQAP RLLIYGASTRATGIPDRFSGSGS GTDFTLTISRLEPEDFAVYYCQQ YARSSTFGQGTKVEIK (SEQ ID NO: 3) | QVQLVQSGAEVKKPGSSVKVSCK ASGGTFSSYTISWVRQAPGQGLE WMGIIPAFGIANYAQKFQGRVTI TADKSTSTAYMELSSLRSEDTAVY YCAKGGSYSLDYFDIWGQGTLVT VSS (SEQ ID NO: 4) |
| P3A1 | DIQMTQSPSSLSASVGDRVTITC RASQSISSYLNWYQQKPGKAPK LLIYAASSLQSGVPSRFSGSGSG TDFTLTISSLQPEDFATYYCQQSY STPLTFGQGTKVEIK (SEQ ID NO: 5) | QVQLVQSGAEVKKPGSSVKVSCK ASGGTFSSYDISWVRQAPGQGLE WMGIIPVSGRANYAQKFQGRVT ITTDKSTSTAYMELSSLRSEDTAVY YCARVRPTYWPLDYWGQGTLVTV SS (SEQ ID NO: 6) |

TABLE 1-continued

| mAb | Light Chain | Heavy Chain |
| --- | --- | --- |
| P5A3 | QSALTQPASVSGSPGQSITISCT GTSSDVGGYNYVSWYQQHPGK APKLMIYEVSKRPSGVPDRFSGS KSGNTASLTVSGLQAEDEADYYCSSYAGSNTVVFGGGTKLTVL (SEQ ID NO: 7) | QVQLVQSGAEVKKPGSSVKVSCK ASGGTFSSYYIGWVRQAPGQGLE WMGGIIPWFGTANYAQKFQGRVT ITADKSTNTAYMELSSLRSEDTAV YYCAADHHDSPSGYTSGGFDVW GQGTLVTVSS (SEQ ID NO: 8) |
| P9B5 | QSVLTQPPSASGTPGQRVTISCS GSSSNIGSNYVYWYQQLPGTAP KLLIYRNNQRPSGVPDRFSGSKS GTSASLAISGLRSEDEADYYCAA WDDSLSGVVFGGGTKLTVL (SEQ ID NO: 9) | EVQLLESGGGLVQPGGSLRLSCA ASGFIFASYAMSWVRQAPGKGLE WVSEISSSGGSTTYADSVKGRFTI SRDNSKNTLYLQMNSLRAEDTAV YYCARDRVMAGLGYDPFDYWGQ GTLVTVSS (SEQ ID NO: 10) |
| P9F1 | QSVLTQPPSASGTPGQRVTISCS GSGSNIGSNYVYWYQQLPGTAP KLLIYRNNQRPSGVPDRFSGSKS GTSASLAISGLRSEDEADYYCAA WDGSLSRPVFGTGTKLTVL (SEQ ID NO: 11) | EVQLLESGGGLVQPGGSLRLSCA ASGFIFSSFAMSWVRQAPGKGLE WVSDISGSGASTTYADSVKGRFTI SRDNSKNTLYLQMNSLRAEDTAV YYCASASGGGSGSYWPYMDPWGQ GTLVTVSS (SEQ ID NO: 12) |
| P1B4 | EIVLTQSPGTLSLSPGERATLSCR ASQSVPNEQLAWYQQKPGQAP RLLIYDASSRATGIPDRFSGSGS GTDFTLTISRLEPEDFAVYYCQQ YGSPPLTFGQGTKVEIK (SEQ ID NO: 13) | QVQLVQSGAEVKKPGSSVKVSCK ASGGVFSRYALSWVRQAPGQGLE WMGGIIPMLGFANYAQKFQGRVT ITADESTSTAYMELSSLRSEDTAV YYCATLDFGALDYWGQGTLVTVS S (SEQ ID NO: 14) |
| P1B11 | EIVLTQSPGTLSLSPGERATLSCR ASQSVSSSELAWYQQKPGQAP RLLIYDASSRATGIPDRFSGSGS GTDFTLTISRLEPEDFAVYYCQQ YDSSPLTFGQGTKVEIK(SEQ ID NO: 15) | QVQLVQSGAEVKKPGSSVKVSCK ASGGTFRSFDISWVRQAPGQGLE WMGRIIPILGYANYAQKFQGRVTI TADESTSTAYMELSSLRSEDTAVY YCASDLGAPWAGYPFDPWGQGT LVTVSS (SEQ ID NO: 16) |
| P7H3 | QSVLTQPPSVSVAPGKTARITCG GNNIGSKSVHWYQQKPGQAPVL VIYYDSDRPSGIPERFSGSNSGN TATLTISRVEAGDEADYYCQVWD SSTAWVFGGGTKLTVL (SEQ ID NO: 17) | EVQLLESGGGLVQPGGSLRLSCA ASGFTFSSYAMHWVRQAPGKGLE WVSAISGSGGSTTYADSVKGRFTI SRDNSKNTLYLQMNSLRAEDTAV YYCARGTRWWWGDAFDHWGQG TLVTVSS (SEQ ID NO: 18) |
| P3E10 | EIVLTQSPGTLSLSPGERATLSCR ASQSVPSSQLAWYQQKPGQAP RLLIYDASSRATGIPDRFSGSGS GTDFTLTISRLEPEDFAVYYCQQ YGSSPLTFGQGTKVEIK (SEQ ID NO: 19) | QVQLVQSGAEVKKPGSSVKVSCK ASGGTFSSYAIQWVRQAPGQGLE WMGGIVGSWGLANYAQKFQGRV TITTDKSTSTAYMELSSLRSEDTAV YYCATSAFGELASWGQGTLVTVS S (SEQ ID NO: 20) |
| P1A5 | EIVLTQSPGTLSLSPGERATLSCR ASQAVDSSDLAWYQQKPGQAP RLLIYDAYTRPSGIPDRFSGSGS GTDFTLTISRLEPEDFAVYYCQQ YGSSPLTFGGGTKLEIK (SEQ ID NO: 21) | QVQLVQSGAEVKKPGSSVKVSCK ASGGVFSRYALSWVRQAPGQGLE WMGGIIPMLGFANYAQKFQGRVT ITADESTSTAYMELSSLRSEDTAV YYCATLDFGALDYWGQGTLVTVS S (SEQ ID NO: 22) |
| P5F7 | EIVLTQSPATLSLSPGERATLSCR ASQSVSSNLAWYQQKPGQAPRL LIYDTFTRATGIPARFSGSGSGTD FTLTISRLEPEDFAVYYCQQYGS SPPTFGQGTRLEIK (SEQ ID NO: 23) | EVQLLESGGGLVQPGGSLRLSCA ASGFTFSSYAMNWVRQAPGKGLE WVSSISGGGRSTYYADSVKGRFTI SRDNSKNTLYLQMNSLRAEDTAV YYCARDLSPSDVGWGYGFDIWG QGTLVTVSS (SEQ ID NO: 24) |
| P4H11 | EIVLTQSPGTLSLSPGERATLSCR ASQSVSNTYLAWYQQKPGQAP RLLIYDTSSRATGIPDRFSGSGS GTDFTLTISRLEPEDFAVYYCQQ YGSSLTFGQGTKVEIK(SEQ ID NO: 25) | EVQLLESGGGLVQPGGSLRLSCA ASGFTFSSYAMNWVRQAPGKGLE WVSSISGGGRSTYYADSVKGRFTI SRDNSKNTLYLQMNSLRAEDTAV YYCARDLSPSDVGWGYGFDIWG QGTLVTVSS (SEQ ID NO: 26) |
| P15F7 | DIQMTQSPSSLSASVGDRVTITC RASQSISTYLNWYQQKPGKAPK LLIYAASNLQSGVPSRFSGSGSG TDFTLTISSLQPEDFATYYCQQSY SIPLTFGQGTKVEIK (SEQ ID NO: 27) | EVQLLESGGGLVQPGGSLRLSCA ASGFTFNNYAMNWVRQAPGKGL EWVSVISGSGGTTYYADSVKGRF TISRDNSKNTLYLQMNSLRAEDTA VYYCASGIWDLRYWGQGTLVTVS S (SEQ ID NO: 28) |

TABLE 1-continued

| mAb | Light Chain | Heavy Chain |
|---|---|---|
| P12B6 | EIVLTQSPGTLSLSPGERATLSCR ASQIVSSSYLAWYQQKPGQAPR LLIYGASSRASGIPDRFSGSGSG TDFTLTISRLEPEDFAVYYCQQY GGSPYTFGQGTKVEIK (SEQ ID NO: 29) | QVQLVQSGAEVKKPGSSVKVSCK ASGGTFMSYAISWVRQAPGQGLE WMGGIIPIFGIANYAQKFQGRVTIT ADKSTSTAYMELSSLRSEDTAVYY CARETLIYPIPFELWGQGTLVTVS S (SEQ ID NO: 30) |
| P8B6 | EIVLTQSPGTLSLSPGERATLSCR ASQSVSHSYLAWYQQKPGQAP RLLIYGASFRAAGIPDRFSGSGS GTDFTLTISRLEPEDFAVYYCQQ YGSDPYTFGQGTKVEIK (SEQ ID NO: 31) | QVQLVQSGAEVKKPGSSVKVSCK ASGGTFSSYAVSWVRQAPGQGLE WMGGIIPIFGIANYAQKFQGRVTIT ADTSTSTAYMELSSLRSEDTAVYY CAIEGIGGDLRYDGYDAWGQGTL VTVSS (SEQ ID NO: 32) |
| P14G2 | DIQMTQSPSSLSASVGDRVTITC RASQSISSYLNWYQQKPGKAPK LLIYDASDLQRGVPSRFSGSGS TDFTLTISSLQPEDFATYYCQQSY NTPWTFGQGTKVEIK (SEQ ID NO: 33) | EVQLLESGGGLVQPGGSLRLSCA ASGFTFSNYVMNWVRQAPGKGLE WVSAISGSGATTYYADSVKGRFTI SRDNSKNTLYLQMNSLRAEDTAV YYCVSGLWAGGIWGQGTLVTVSS (SEQ ID NO: 34) |
| P7F9 | NFMLTQPHSVSESPGKTVTISCT RSSGSIASNYVQWYQQKPGQAP VLWYDDSDRPSGIPERFSGSNS GNTATLTISRVEAGDEADYYCQV WDSSSDHWVFGGGTKLTVL (SEQ ID NO: 35) | EVQLLESGGGLVQPGGSLRLSCA ASGFTFSSYAMSWVRQAPGKGLE WVSAIGGSGGSTYYADSVKGRFT ISRDNSKNTLYLQMNSLRAEDTAM YYCARDYYAFSDPAYGGMDVWG QGTLVTVSS (SEQ ID NO: 36) |
| P08B06EE | EIVLTQSPGTLSLSPGERATLSCR ASQSVSHSYLAWYQQKPGQAP RLLIYGASFRAAGIPDRFSGSGS GTDFTLTISRLEPEDFAVYYCQQ YGSEPYTFGQGTKVEIK(SEQ ID NO: 204) | QVQLVQSGAEVKKPGSSVKVSCK ASGGTFSSYAVSWVRQAPGQGLE WMGGIIPIFGIANYAQKFQGRVTIT ADTSTSTAYMELSSLRSEDTAVYY CAIEGIGGDLRYEGYDAWGQGTL VTVSS (SEQ ID NO: 205) |
| P04A04 | EIVLTQSPGTLSLSPGERATLSCR ASQSVTSSQLAWYQQKPGQAP RLLIYDASSRATGIPDRFSGSGS GTDFTLTISRLEPEDFAVYYCQQ YGSSLLITFGQGTKVEIK (SEQ ID NO: 206) | QVQLVQSGAEVKKPGSSVKVSCK ASGGTFSSYYITVWRQAPGQGLE WMGRIMPAFGWTNYAQKFQGRV TITTDKSTSTAYMELSSLRSEDTAV YYCASDEFGAFDVWGQGTLVTVS S (SEQ ID NO: 207) |
| P01A05 | EIVLTQSPGTLSLSPGERATLSCR ASQAVDSSDLAWYQHKPGQAP RLLIYDAYTRPSGIPDRFSGSGS GTDFTLTISRLEPEDFAVYYCQQ YGSSPLTFGGGTKLEIK (SEQ ID NO: 208) | QVQLVQSGAEVKKPGSSVKVSCK ASGGVFSRYALSWVRQAPGQGLE WMGGIIPMLGFANYAQKFQGRVTI TADESTSTAYMELSSLRSEDTAVY YCATLDFGALDYWGQGTLVTVSS (SEQ ID NO: 209) |
| P08B03 | DIVMTQSPGTLSLSPGERATLSC RASQSVSSNLAWYQQKPGQAP RLLIYDAYTRATGIPARFSGSGS GTDFTLTISRLEPEDFAVYYCQQ YGSPYTFGQGTKVEIK (SEQ ID NO: 210) | QVQLVQSGAEVKKPGSSVKVSCK ASGGTFSSYDISWVRQAPGQGLE WMGRIIPSFGANYAQKFQGRVTI TADKSTSTAYMELSSLRSEDTAVY YCATDDGEGWTPPFGYWGQGTL VTVSS (SEQ ID NO: 211) |
| P5F7 | DIVMTQSPATLSLSPGERATLSC RASQSVSSNLAWYQQKPGQAP RLLIYDTFTRATGIPARFSGSGSG TDFTLTISRLEPEDFAVYYCQQY GSSPPTFGQGTRLEIK (SEQ ID NO: 212) | EVQLLESGGGLVQPGGSLRLSCA ASGFTFSSYAMNWVRQAPGKGLE WVSSISGGGRSTYYADSVKGRFTI SRDNSKNTLYLQMNSLRAEDTAV YYCARDLSPSDVGWGYGFDIWG QGTLVTVSS (SEQ ID NO: 213) |
| P5F7g | EIVLTQSPATLSLSPGERATLSCR ASQSVSSNLAWYQQKPGQAPRL LIYDTFTRATGIPARFSGSGSGTD FTLTISSLEPEDFAVYYCQQYGS SPPTFGQGTRLEIK (SEQ ID NO: 214) | EVQLLESGGGLVQPGGSLRLSCA ASGFTFSSYAMNWVRQAPGKGLE WVSSISGGGRSTYYADSVKGRFTI SRDNSKNTLYLQMNSLRAEDTAV YYCARDLSPSDVGWGYGFDIWG QGTLVTVSS (SEQ ID NO: 215) |
| P10A02g | EIVLTQSPATLSLSPGERATLSCR ASQDVSDLLAWYQQKPGQAPRL LIYDAYTRATGIPARFSGSGSGT DFTLTISSLEPEDFAVYYCQQYA SSPITFGQGTRLEIK (SEQ ID NO: 216) | EVQLLESGGGLVQPGGSLRLSCA ASGFTFSSYAMNWVRQAPGKGLE WVSSISGGGRSTYYADSVKGRFTI SRDNSKNTLYLQMNSLRAEDTAV YYCARDLSPSDVGWGYGFDIWG QGTLVTVSS (SEQ ID NO: 217) |

TABLE 1-continued

| mAb | Light Chain | Heavy Chain |
|---|---|---|
| P10A04g | EIVLTQSPATLSLSPGERATLSCR ASQKVSDLLAWYQQKPGQAPRL LIYDAYTRATGIPARFSGSGSGT DFTLTISSLEPEDFAVYYCQQYT GSPITFGQGTRLEIK (SEQ ID NO: 218) | EVQLLESGGGLVQPGGSLRLSCA ASGFTFSSYAMNWVRQAPGKGLE WVSSISGGGRSTYYADSVKGRFTI SRDNSKNTLYLQMNSLRAEDTAV YYCARDLSPSDVGWGYGFDIWG QGTLVTVSS (SEQ ID NO: 219) |
| P10A05g | EIVLTQSPATLSLSPGERATLSCR ASLSVSDLLAWYQQKPGQAPRL LIYDAYSRATGIPARFSGSGSGT DFTLTISSLEPEDFAVYYCQQYSS NPITFGQGTRLEIK (SEQ ID NO: 220) | EVQLLESGGGLVQPGGSLRLSCA ASGFTFSSYAMNWVRQAPGKGLE WVSSISGGGRSTYYADSVKGRFTI SRDNSKNTLYLQMNSLRAEDTAV YYCARDLSPSDVGWGYGFDIWG QGTLVTVSS (SEQ ID NO: 221) |
| P10A07g | EIVLTQSPATLSLSPGERATLSCR ASGSVSDLLAWYQQKPGQAPRL LIYDAYSRATGIPARFSGSGSGT DFTLTISSLEPEDFAVYYCQQYA SYPITFGQGTRLEIK (SEQ ID NO: 222) | EVQLLESGGGLVQPGGSLRLSCA ASGFTFSSYAMNWVRQAPGKGLE WVSSISGGGRSTYYADSVKGRFTI SRDNSKNTLYLQMNSLRAEDTAV YYCARDLSPSDVGWGYGFDIWG QGTLVTVSS (SEQ ID NO: 223) |
| P10B03g | EIVLTQSPATLSLSPGERATLSCR ASQSVSDLLAWYQQKPGQAPRL LIYDAFSRATGIPARFSGSGSGT DFTLTISSLEPEDFAVYYCQQYG TPPITFGQGTRLEIK (SEQ ID NO: 224) | EVQLLESGGGLVQPGGSLRLSCA ASGFTFSSYAMNWVRQAPGKGLE WVSSISGGGRSTYYADSVKGRFTI SRDNSKNTLYLQMNSLRAEDTAV YYCARDLSPSDVGWGYGFDIWG QGTLVTVSS (SEQ ID NO: 225) |
| P10B06g | EIVLTQSPATLSLSPGERATLSCR ASESVSDLLAWYQQKPGQAPRL LIYDAYSRATGIPARFSGSGSGT DFTLTISSLEPEDFAVYYCQQYS ASPITFGQGTRLEIK (SEQ ID NO: 226) | EVQLLESGGGLVQPGGSLRLSCA ASGFTFSSYAMNWVRQAPGKGLE WVSSISGGGRSTYYADSVKGRFTI SRDNSKNTLYLQMNSLRAEDTAV YYCARDLSPSDVGWGYGFDIWG QGTLVTVSS (SEQ ID NO: 227) |
| P5F7g2 | EIVLTQSPATLSLSPGERATLSCR ASQSVSSNLAWYQQKPGQAPRL LIYDTFTRATGIPARFSGSGSGTD FTLTISSLEPEDFAVYYCQQYGS SPPTFGQGTRLEIK (SEQ ID NO: 228) | EVQLLESGGGLVQPGGSLRLSCA ASGFTFSSYAMNWVRQAPGKGLE WVSAISGGGRSTYYADSVKGRFTI SRDNSKNTLYLQMNSLRAEDTAV YYCARDLSPSDVGWGYGFDIWG QGTLVTVSS (SEQ ID NO: 229) |
| P5F7g3 | EIVLTQSPATLSLSPGERATLSCR ASQSVSSLLAWYQQKPGQAPRL LIYDAYTRATGIPARFSGSGSGT DFTLTISSLEPEDFAVYYCQQYT GSPITFGQGTRLEIK (SEQ ID NO: 230) | EVQLLESGGGLVQPGGSLRLSCA ASGFTFSSYAMNWVRQAPGKGLE WVSAISGGGRSTYYADSVKGRFTI SRDNSKNTLYLQMNSLRAEDTAV YYCARDLSPSDVGWGYGFDIWG QGTLVTVSS (SEQ ID NO: 231) |
| P5F7g4 | EIVLTQSPATLSLSPGERATLSCR ASQSVSSLLAWYQQKPGQAPRL LIYDAYTRATGIPARFSGSGSGT DFTLTISSLEPEDFAVYYCQQYT GSPITFGQGTRLEIK (SEQ ID NO: 232) | EVQLLESGGGLVQPGGSLRLSCA ASGFTFSSYAMSWVRQAPGKGLE WVSAISGGGRSTYYADSVKGRFTI SRDNSKNTLYLQMNSLRAEDTAV YYCARDLSPSDVGWGYGFDIWG QGTLVTVSS (SEQ ID NO: 233) |

Also provided herein are CDR portions of antigen binding domains of antibodies to FLT3 (including Chothia, Kabat CDRs, and CDR contact regions). Determination of CDR regions is well within the skill of the art. It is understood that in some embodiments, CDRs can be a combination of the Kabat and Chothia CDR (also termed "combined CRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof. Table 2 provides examples of CDR sequences provided herein.

TABLE 2

| | Heavy Chain | | |
|---|---|---|---|
| mAb | CDRH1 | CDRH2 | CDRH3 |
| P4F6 | SYGIS (SEQ ID NO: 37) (Kabat); GGTFGSY (SEQ ID | GIIPIFGTVTYAQK FQG (SEQ ID NO: 40) (Kabat); | DSWSGATGAS DT (SEQ ID NO: 42) |

TABLE 2-continued

| | | 38) (Chothia);<br>GGTFGSYGIS (SEQ ID NO: 39) (Extended) | IPIFGT (SEQ ID NO: 41) (Chothia) | |
| --- | --- | --- | --- | --- |
| P4C7 | SYTIS (SEQ ID NO: 43) (Kabat);<br>GGTFSSY (SEQ ID NO: 44) (Chothia);<br>GGTFSSYTIS (Extended) (SEQ ID NO: 45) | GIIPAFGIANYAQKFQG (SEQ ID NO: 46) (Kabat);<br>IPAFGI (SEQ ID NO: 47) (Chothia) | GGSYSLDYFDI (SEQ ID NO: 48) | |
| P3A1 | SYDIS (SEQ ID NO: 49) (Kabat);<br>GGTFSSY (SEQ ID NO: 44) (Chothia);<br>GGTFSSYDIS (SEQ ID NO: 50) (Extended) | GIIPVSGRANYAQKFQG (SEQ ID NO: 51) (Kabat);<br>IPVSGR (SEQ ID NO: 52) (Chothia) | VRPTYWPLDY (SEQ ID NO: 53) | |
| P5A3 | SYYIG (SEQ ID NO: 54) (Kabat);<br>GGTFSSY (SEQ ID NO: 55) (Chothia);<br>GGTFSSYYIG (SEQ ID NO: 56) (Extended) | GIIPWFGTANYAQKFQG (SEQ ID NO: 57) (Kabat);<br>IPWFGT (SEQ ID NO: 58) (Chothia) | DHHDSPSGYTSGGFDV (SEQ ID NO: 59) | |
| P9B5 | SYAMS (SEQ ID NO: 60) (Kabat);<br>GFIFASY (SEQ ID NO: 61) (Chothia);<br>GFIFASYAMS (SEQ ID NO: 62) (Extended) | EISSSGGSTTYADSVKG (SEQ ID NO: 63) (Kabat);<br>SSSGGS (SEQ ID NO: 64) (Chothia) | DRVMAGLGYDPFDY (SEQ ID NO: 65) | |
| P9F1 | SFAMS (SEQ ID NO: 66) (Kabat);<br>GFIFSSF (SEQ ID NO: 67) (Chothia);<br>GFIFSSFAMS (SEQ ID NO: 68) (Extended) | DISGSGASTYYADSVKG (SEQ ID NO: 69) (Kabat);<br>SGSGAS (SEQ ID NO: 70) (Chothia) | ASGGSGSYWPYMDP (SEQ ID NO: 71) | |
| P1B4 | RYALS (SEQ ID NO: 72) (Kabat);<br>GGVFSRY (SEQ ID NO: 73) (Chothia);<br>GGVFSRYALS (SEQ ID NO: 74) (Extended) | GIIPMLGFANYAQKFQG (SEQ ID NO: 75) (Kabat);<br>IPMLGF (SEQ ID NO: 76) (Chothia) | LDFGALDY (SEQ ID NO: 77) | |
| P1B11 | SFDIS (SEQ ID NO: 78) (Kabat);<br>GGTFRSF (SEQ ID NO: 79) (Chothia);<br>GGTFRSFDIS (SEQ ID NO: 80) (Extended) | RIIPILGYANYAQKFQG (SEQ ID NO: 81) (Kabat);<br>IPILGY (SEQ ID NO: 82) (Chothia) | DLGAPWAGYPFDP (SEQ ID NO: 83) | |
| P7H3 | SYAMH (SEQ ID NO: 84) (Kabat);<br>GFTFSSY (SEQ ID NO: 85) (Chothia);<br>GFTFSSYAMH (SEQ ID NO: 86) (Extended) | AISGSGGSTYYADSVKG (SEQ ID NO: 87) (Kabat);<br>SGSGGS (SEQ ID NO: 88) (Chothia) | GTRWWWGDAFDH (SEQ ID NO: 89) | |
| P3E10 | SYAIQ (SEQ ID NO: 90) (Kabat);<br>GGTFSSY (SEQ ID NO: 91) (Chothia);<br>GGTFSSYAIQ (SEQ ID NO: 92) (Extended) | GIVGSWGLANYAQKFQG (SEQ ID NO: 93) (Kabat);<br>VGSWGL (SEQ ID NO: 94) (Chothia) | SAFGELAS (SEQ ID NO: 95) | |
| P1A5 | RYALS (SEQ ID NO: 96) (Kabat);<br>GGVFSRY (SEQ ID NO: 97) (Chothia);<br>GGVFSRYALS (SEQ ID NO: 98) (Extended) | GIIPMLGFANYAQKFQG (SEQ ID NO: 99) (Kabat);<br>IPMLGF (SEQ ID NO: 100) (Chothia) | LDFGALDY (SEQ ID NO: 101) | |
| P5F7 | SYAMN (SEQ ID NO: 102) (Kabat);<br>GFTFSSY (SEQ ID NO: 103) (Chothia);<br>GFTFSSYAMN (SEQ ID NO: 104) (Extended) | SISGGGRSTYYADSVKG (SEQ ID NO: 105) (Kabat);<br>SGGGRS (SEQ ID NO: 106) (Chothia) | DLSPSDVGWGYGFDI (SEQ ID NO: 107) | |

TABLE 2-continued

| | | | |
|---|---|---|---|
| P4H11 | SYAMN (SEQ ID NO: 108) (Kabat); GFTFSSY (SEQ ID NO: 109) (Chothia); GFTFSSYAMN (SEQ ID NO: 110) (Extended) | SISGGGRSTYYAD SVKG (SEQ ID NO: 111) (Kabat); SGGGRS (SEQ ID NO: 112) (Chothia) | DLSPSDVGWG YGFDI (SEQ ID NO: 113) |
| P15F7 | NYAMN (SEQ ID NO: 114) (Kabat); GFTFNNY (SEQ ID NO: 115) (Chothia); GFTFNNYAMN (SEQ ID NO: 116) (Extended) | VISGSGGTTYYAD SVKG (SEQ ID NO: 117) (Kabat); SGSGGT (SEQ ID NO: 118) (Chothia) | GIWDLRY (SEQ ID NO: 119) |
| P12B6 | SYAIS (SEQ ID NO: 120) (Kabat); GGTFMSY (SEQ ID NO: 121) (Chothia); GGTFMSYAIS (SEQ ID NO: 122) (Extended) | GIIPIFGIANYAQKF QG (SEQ ID NO: 123) (Kabat); IPIFGI (SEQ ID NO: 124) (Chothia) | ETLIYPIPFEL (SEQ ID NO: 125) |
| P8B6 | SYAVS (SEQ ID NO: 126) (Kabat); GGTFSSY (SEQ ID NO: 127) (Chothia); GGTFSSYAVS (SEQ ID NO: 128) (Extended) | GIIPIFGIANYAQKF QG (SEQ ID NO: 129) (Kabat); IPIFGI (SEQ ID NO: 130) (Chothia) | EGIGGDLRYD GYDA (SEQ ID NO: 131) |
| P14G2 | NYVMN (SEQ ID NO: 132) (Kabat); GFTFSNY (SEQ ID NO: 133) (Chothia); GFTFSNYVMN (SEQ ID NO: 134) (Extended) | AISGSGATTYYAD SVKG (SEQ ID NO: 135) (Kabat); SGSGAT (SEQ ID NO: 136) (Chothia) | GLWAGGI (SEQ ID NO: 137) |
| P7F9 | SYAMS (SEQ ID NO: 138) (Kabat); GFTFSSY (SEQ ID NO: 139) (Chothia); GFTFSSYAMS (SEQ ID NO: 140) (Extended) | AIGGSGGSTYYAD SVKG (SEQ ID NO: 141) (Kabat); GGSGGS (SEQ ID NO: 142) (Chothia) | DYYAFSDPAY GGMDV (SEQ ID NO: 143) |
| P08B06EE | SYAVS (SEQ ID NO: 126) (Kabat); GGTFSSY (SEQ ID NO: 127) (Chothia); GGTFSSYAVS (SEQ ID NO: 128) (Extended) | GIIPIFGIANYAQKF QG (SEQ ID NO: 129) (Kabat); IPIFGI (SEQ ID NO: 130) (Chothia) | EGIGGDLRYE GYDA (SEQ ID NO: 245) |
| P04A04 | SYYIT (SEQ ID NO: 247) GGTFSSY (SEQ ID NO: 127) (Chothia) GGTFSSYYIT (SEQ ID NO: 246) (Extended) | RIMPAFGWTNYA QKFQG (SEQ ID NO: 248) (Kabat) MPAFGW (SEQ ID NO: 249) (Chothia) | DEFGAFDV (SEQ ID NO: 250) |
| P01A05 | RYALS (SEQ ID NO: 72) (Kabat); GGVFSRY (SEQ ID NO: 73) (Chothia); GGVFSRYALS (SEQ ID NO: 74) (Extended) | IPMLGF (SEQ ID NO: 100) (Chothia) GGIIPMLGFANYA QKFQG (SEQ ID NO: 251) (Kabat) | LDFGALDY (SEQ ID NO: 77) |
| P08B03 | SYDIS (SEQ ID NO: 49) (Kabat); GGTFSSY (SEQ ID NO: 44) (Chothia); GGTFSSYDIS (SEQ ID NO: 50) (Extended) | RHPSFGAANYAQK FQG (SEQ ID NO: 253) (Kabat); IPSFGA (SEQ ID NO: 252) (Chothia ) | DDGEGWTPPF GY (SEQ ID NO: 254) |
| P5F7g; P10A02g; P10A04g; P10A05g; P10A07g; P10B03g; P10B06g | SYAMN (SEQ ID NO: 102) (Kabat); GFTFSSY (SEQ ID NO: 103) (Chothia); GFTFSSYAMN (SEQ ID NO: 104) (Extended) | SISGGGRSTYYAD SVKG (SEQ ID NO: 105) (Kabat); SGGGRS (SEQ ID NO: 106) (Chothia) | DLSPSDVGWG YGFDI (SEQ ID NO: 107) |

TABLE 2-continued

| mAb | | | |
|---|---|---|---|
| P5F7g2; P5F7g3 | SYAMN (SEQ ID NO: 102) (Kabat); GFTFSSY (SEQ ID NO: 103) (Chothia); GFTFSSYAMN (SEQ ID NO: 104) (Extended) | AISGGGRSTYYAD SVKG (SEQ ID NO: 255) (Kabat); SGGGRS (SEQ ID NO: 106) (Chothia) | DLSPSDVGWG YGFDI (SEQ ID NO: 107) |
| P5F7g4 | SYAMS (SEQ ID NO: 138) (Kabat); GFTFSSY (SEQ ID NO: 139) (Chothia); GFTFSSYAMS (SEQ ID NO: 140) (Extended) | AISGGGRSTYYAD SVKG (SEQ ID NO: 255) (Kabat); SGGGRS (SEQ ID NO: 106) (Chothia) | DLSPSDVGWG YGFDI (SEQ ID NO: 107) |

Light Chain

| mAb | CDRL1 | CDRL2 | CDRL3 |
|---|---|---|---|
| P4F6 | RASHSVSSSYLA (SEQ ID NO: 144) | GASSRAT (SEQ ID NO: 145) | QQYGSPPRT (SEQ ID NO: 146) |
| P4C7 | RASQYVSASLLA (SEQ ID NO: 147) | GASTRAT (SEQ ID NO: 148) | QQYARSST (SEQ ID NO: 149) |
| P3A1 | RASQSISSYLN (SEQ ID NO: 150) | AASSLQS (SEQ ID NO: 151) | QQSYSTPLT (SEQ ID NO: 152) |
| P5A3 | TGTSSDVGGYNYVS (SEQ ID NO: 153) | EVSKRPS (SEQ ID NO: 154) | SSYAGSNTVV (SEQ ID NO: 155) |
| P9B5 | SGSSSNIGSNYVY (SEQ ID NO: 156) | RNNQRPS (SEQ ID NO: 157) | AAWDDSLSGV V (SEQ ID NO: 158) |
| P9F1 | SGSGSNIGSNYVY (SEQ ID NO: 159) | RNNQRPS (SEQ ID NO: 160) | AAWDGSLSRP V (SEQ ID NO: 161) |
| P1B4 | RASQSVPNEQLA (SEQ ID NO: 162) | DASSRAT (SEQ ID NO: 163) | QQYGSPPLT (SEQ ID NO: 164) |
| P1B11 | RASQSVSSSELA (SEQ ID NO: 165) | DASSRAT (SEQ ID NO: 166) | QQYDSSPLT (SEQ ID NO: 167) |
| P7H3 | GGNNIGSKSVH (SEQ ID NO: 168) | YDSDRPS (SEQ ID NO: 169) | QVWDSSTAWV (SEQ ID NO: 170) |
| P3E10 | RASQSVPSSQLA (SEQ ID NO: 171) | DASSRAT (SEQ ID NO: 172) | QQYGSSPLT (SEQ ID NO: 173) |
| P1A5 | RASQAVDSSDLA (SEQ ID NO: 174) | DAYTRPS (SEQ ID NO: 175) | QQYGSSPLT (SEQ ID NO: 176) |
| P5F7 | RASQSVSSNLA (SEQ ID NO: 177) | DTFTRAT (SEQ ID NO: 178) | QQYGSSPPT (SEQ ID NO: 179) |
| P4H11 | RASQSVSNTYLA (SEQ ID NO: 180) | DTSSRAT (SEQ ID NO: 181) | QQYGSSLT (SEQ ID NO: 182) |
| P15F7 | RASQSISTYLN (SEQ ID NO: 183) | AASNLQS (SEQ ID NO: 184) | QQSYSIPLT (SEQ ID NO: 185) |
| P12B6 | RASQIVSSSYLA (SEQ ID NO: 186) | GASSRAS (SEQ ID NO: 187) | QQYGGSPYT (SEQ ID NO: 188) |

TABLE 2-continued

| | | | |
|---|---|---|---|
| P8B6 | RASQSVSHSYLA (SEQ ID NO: 189) | GASFRAA (SEQ ID NO: 190) | QQYGSDPYT (SEQ ID NO: 191) |
| P14G2 | RASQSISSYLN (SEQ ID NO: 192) | DASDLQR (SEQ ID NO: 193) | QQSYNTPWT (SEQ ID NO: 194) |
| P7F9 | TRSSGSIASNYVQ (SEQ ID NO: 195) | DDSDRPS (SEQ ID NO: 196) | QVWDSSSDHWV (SEQ ID NO: 197) |
| P08B06EE | RASQSVSHSYLA (SEQ ID NO: 189) | GASFRAA (SEQ ID NO: 190) | QQYGSEPYT (SEQ ID NO: 256) |
| P04A04 | RASQSVTSSQLA (SEQ ID NO: 257) | GASFRAA (SEQ ID NO: 190) | QQYGSSLLIT (SEQ ID NO: 258) |
| P01A05 | RASQAVDSSDLA (SEQ ID NO: 174) | DAYTRPS (SEQ ID NO: 175) | QQYGSSPLT (SEQ ID NO: 176) |
| P08B03 | RASQSVSSNLA (SEQ ID NO: 177) | DAYTRAT (SEQ ID NO: 259) | QQYGSPYT (SEQ ID NO: 260) |
| P5F7g | RASQSVSSNLA (SEQ ID NO: 177) | DTFTRAT (SEQ ID NO: 178) | QQYGSSPPT (SEQ ID NO: 179) |
| P10A02g | RASQDVSDLLA (SEQ ID NO: 261) | DAYTRAT (SEQ ID NO: 259) | QQYASSPIT (SEQ ID NO: 262) |
| P10A04g | RASQKVSDLLA (SEQ ID NO: 263) | DAYTRAT (SEQ ID NO: 259) | QQYTGSPIT (SEQ ID NO: 264) |
| P10A05g | RASLSVSDLLA (SEQ ID NO: 265) | DAYS RAT (SEQ ID NO: 266) | QQYSSNPIT (SEQ ID NO: 267) |
| P10A07g | RASGSVSDLLA (SEQ ID NO: 268) | DAYS RAT (SEQ ID NO: 266) | QQYASYPIT (SEQ ID NO: 269) |
| P10B03g | RASQSVSDLLA (SEQ ID NO: 270) | DAFSRAT (SEQ ID NO: 271) | QQYGTPPIT (SEQ ID NO: 272) |
| P10B06g | RASESVSDLLA (SEQ ID NO: 273) | DAYS RAT (SEQ ID NO: 266) | QQYSASPIT (SEQ ID NO: 274) |
| P5F7g2 | RASQSVSSNLA (SEQ ID NO: 177) | DTFTRAT (SEQ ID NO: 178) | QQYGSSPPT (SEQ ID NO: 179) |
| P5F7g3; P5F7g4 | RASQSVSSLLA (SEQ ID NO: 275) | DAYTRAT (SEQ ID NO: 259) | QQYTGSPIT (SEQ ID NO: 264) |

In some embodiments, the present invention provides an antibody that binds to FLT3 and competes with the antibody as described herein, including P4F6, P4C7, P3A, P5A3, P9B5, P9F1, P1B4, P1B11, P7H3, P3E10, P1A5, P5F7, P4H11, P15F7, P12B6, P8B6, P14G2, P7F9, P08B06EE, P04A04, P01A05, P08B03, P5F7, P5F7g, P10A02g, P10A04g, P10A05g, P10A07g, P10B03g, P10B06g, P5F7g2, P5F7g3, or P5F7g4.

In some embodiments, the invention also provides CDR portions of antibodies to FLT3 antibodies based on CDR contact regions. CDR contact regions are regions of an antibody that imbue specificity to the antibody for an antigen. In general, CDR contact regions include the residue positions in the CDRs and Vernier zones which are constrained in order to maintain proper loop structure for the antibody to bind a specific antigen. See, e.g., Makabe et al., J. Biol. Chem., 283:1156-1166, 2007. Determination of CDR contact regions is well within the skill of the art.

The binding affinity ($K_D$) of the FLT3 antibody as described herein to FLT3 (such as human FLT3 (e.g., (SEQ ID NO: 201)) can be about 0.001 to about 5000 nM. In some embodiments, the binding affinity is about any of 5000 nM, 4500 nM, 4000 nM, 3500 nM, 3000 nM, 2500 nM, 2000 nM, 1789 nM, 1583 nM, 1540 nM, 1500 nM, 1490 nM, 1064 nM, 1000 nM, 933 nM, 894 nM, 750 nM, 705 nM, 678 nM, 532 nM, 500 nM, 494 nM, 400 nM, 349 nM, 340 nM, 353 nM, 300 nM, 250 nM, 244 nM, 231 nM, 225 nM, 207 nM, 200 nM, 186 nM, 172 nM, 136 nM, 113 nM, 104 nM, 101 nM, 100 nM, 90 nM, 83 nM, 79 nM, 74 nM, 54 nM, 50 nM, 45 nM, 42 nM, 40 nM, 35 nM, 32 nM, 30 nM, 25 nM, 24 nM, 22 nM, 20 nM, 19 nM, 18 nM, 17 nM, 16 nM, 15 nM, 12 nM, 10 nM, 9 nM, 8 nM, 7.5 nM, 7 nM, 6.5 nM, 6 nM, 5.5 nM, 5 nM, 4 nM, 3 nM, 2 nM, 1 nM, 0.5 nM, 0.3 nM, 0.1 nM, 0.01 nM, or 0.001 nM. In some embodiments, the binding affinity is less than about any of 5000 nM, 4000 nM, 3000 nM, 2000 nM, 1000 nM, 900 nM, 800 nM, 250 nM, 200 nM, 100 nM, 50 nM, 30 nM, 20 nM, 10 nM, 7.5 nM, 7 nM, 6.5 nM, 6 nM, 5 nM, 4.5 nM, 4 nM, 3.5 nM, 3 nM, 2.5 nM, 2 nM, 1.5 nM, 1 nM, or 0.5 nM.

Bispecific antibodies, monoclonal antibodies that have binding specificities for at least two different antigens, can be prepared using the antibodies disclosed herein. Methods for making bispecific antibodies are known in the art (see, e.g., Suresh et al., Methods in Enzymology 121:210, 1986). Traditionally, the recombinant production of bispecific antibodies was based on the coexpression of two immunoglobulin heavy chain-light chain pairs, with the two heavy chains having different specificities (Millstein and Cuello, Nature 305, 537-539, 1983). Accordingly, in one aspect, provided is a bispecific antibody wherein the bispecific antibody is a full-length human antibody, comprising a first antibody variable domain of the bispecific antibody specifically binding to a target antigen (e.g., FLT3), and comprising a second antibody variable domain of the bispecific antibody capable of recruiting the activity of a human immune effector cell by specifically binding to an effector antigen located on the human immune effector cell.

The human immune effector cell can be any of a variety of immune effector cells known in the art. For example, the immune effector cell can be a member of the human lymphoid cell lineage, including, but not limited to, a T cell (e.g., a cytotoxic T cell), a B cell, and a natural killer (NK) cell. The immune effector cell can also be, for example without limitation, a member of the human myeloid lineage, including, but not limited to, a monocyte, a neutrophilic granulocyte, and a dendritic cell. Such immune effector cells may have either a cytotoxic or an apoptotic effect on a target cell or other desired effect upon activation by binding of an effector antigen.

The effector antigen is an antigen (e.g., a protein or a polypeptide) that is expressed on the human immune effector cell. Examples of effector antigens that can be bound by the heterodimeric protein (e.g., a heterodimeric antibody or a bispecific antibody) include, but are not limited to, human CD3 (or CD3 (Cluster of Differentiation) complex), CD16, NKG2D, NKp46, CD2, CD28, CD25, CD64, and CD89.

The target cell can be a cell that is native or foreign to humans. In a native target cell, the cell may have been transformed to be a malignant cell or pathologically modified (e.g., a native target cell infected with a virus, a plasmodium, or a bacterium). In a foreign target cell, the cell is an invading pathogen, such as a bacterium, a plasmodium, or a virus.

The target antigen is expressed on a target cell in a diseased condition (e.g., an inflammatory disease, a proliferative disease (e.g., cancer), an immunological disorder, a neurological disease, a neurodegenerative disease, an autoimmune disease, an infectious disease (e.g., a viral infection or a parasitic infection), an allergic reaction, a graft-versus-host disease or a host-versus-graft disease). A target antigen is not effector antigen. In some embodiments, the target antigen is FLT3.

In some embodiments, provided is a bispecific antibody wherein the bispecific antibody is a full-length antibody, comprising a first antibody variable domain of the bispecific antibody specifically binding to a target antigen, and comprising a second antibody variable domain of the bispecific antibody capable of recruiting the activity of a human immune effector cell by specifically binding to an effector antigen located on the human immune effector cell, wherein the first antibody variable domain binds to domain 4 of FLT3 comprising SEQ ID NO: 279.

In some embodiments, provided is a bispecific antibody, wherein the bispecific antibody is a full-length antibody, comprising a first antibody variable domain of the bispecific antibody specifically binding to a target antigen, and comprising a second antibody variable domain of the bispecific antibody capable of recruiting the activity of a human immune effector cell by specifically binding to an effector antigen located on the human immune effector cell, wherein the first antibody variable domain comprises a heavy chain variable (VH) region comprising a VH CDR1, VH CDR2, and VH CDR3 of the VH sequence shown in SEQ ID NO: 2, 4, 6, 8, 10, 12, 14, 16, 18, 20, 22, 24, 26, 28, 30, 32, 34, 36, 205, 207, 209, 211, 213, 215, 217, 219, 221, 223, 225, 227, 229, 231, or 233; and/or a light chain variable (VL) region comprising VL CDR1, VL CDR2, and VL CDR3 of the VL sequence shown in SEQ ID NO: 1, 3, 5, 7, 9, 11, 13, 15, 17, 19, 21, 23, 25, 27, 29, 31, 33, 35, 204, 206, 208, 210, 212, 214, 216, 218, 220, 222, 224, 226, 228, 230, or 232.

In some embodiments, provided is a bispecific antibody, wherein the bispecific antibody is a full-length antibody, comprising a first antibody variable domain of the bispecific antibody specifically binding to a target antigen, and comprising a second antibody variable domain of the bispecific antibody capable of recruiting the activity of a human immune effector cell by specifically binding to an effector antigen located on the human immune effector cell, wherein the first antibody variable domain comprises (a) a heavy chain variable (VH) region comprising (i) a VH complementarity determining region one (CDR1) comprising the sequence shown in SEQ ID NO: 37, 38, 39, 43, 44, 45, 49, 50, 54, 55, 56, 60, 61, 62, 66, 67, 68, 72, 73, 74, 78, 79, 80, 84, 85, 86, 90, 91, 92, 96, 97, 98, 102, 103, 104, 108, 109, 110, 114, 115, 116, 120, 121, 122, 126, 127, 128, 132, 133, 134, 138, 139, 140, 246, or 247; (ii) a VH CDR2 comprising the sequence shown in SEQ ID NO: 40, 41, 46, 47, 51, 52, 57, 58, 63, 64, 69, 70, 75, 76, 81, 82, 87, 88, 93, 94, 99, 100, 105, 106, 111, 112, 117, 118, 123, 124, 129, 130, 135, 136, 141, 142, 248, 249, 251, 252, 253, or 255; and iii) a VH CDR3 comprising the sequence shown in SEQ ID NO: 42, 48, 53, 59, 65, 71, 77, 83, 89, 95, 101, 107, 113, 119, 125, 131, 137, 143, 245, 250, or 254; and/or a light chain variable (VL) region comprising (i) a VL CDR1 comprising the sequence shown in SEQ ID NO: 144, 147, 150, 153, 156, 159, 162, 165, 168, 171, 174, 177, 180, 183, 186, 189, 192, 195, 257, 261, 263, 265, 268, 270, 273, or 275; (ii) a VL CDR2 comprising the sequence shown in SEQ ID NO: 145, 148, 151, 154, 157, 160, 163, 166, 169, 172, 175, 178, 181, 184, 187, 190, 193, 196, 259, 266, or 271; and (iii) a VL CDR3 comprising the sequence shown in SEQ ID NO: 146, 149, 152, 155, 158, 161, 164, 167, 170, 173, 176, 179, 182, 185, 188, 191, 194, 197, 256, 258, 260, 262, 264, 267, 269, 272, or 274.

In some embodiments, the first antibody variable domain comprises (a) a heavy chain variable (VH) region comprising (i) a VH complementary determining region one (CDR1) comprising the sequence shown in SEQ ID NO: 102, 103, or 104; (ii) a VH CDR2 comprising the sequence shown in SEQ ID NO: 255 or 106; and iii) a VH CDR3 comprising the sequence shown in SEQ ID NO: 107; and/or (b) a light chain variable (VL) region comprising (i) a VL CDR1 comprising the sequence shown in SEQ ID NO: 177; (ii) a VL CDR2 comprising the sequence shown in SEQ ID NO: 178; and (iii) a VL CDR3 comprising the sequence shown in SEQ ID NO: 179.

In some embodiments, the second antibody variable domain comprises a heavy chain variable (VH) region comprising a VH CDR1, VH CDR2, and VH CDR3 of the VH sequence shown in SEQ ID NO: 282; and/or a light chain variable (VL) region comprising VL CDR1, VL CDR2, and VL CDR3 of the VL sequence shown in SEQ ID NO: 281.

In some embodiments, the first antibody variable domain comprises a heavy chain variable (VH) region comprising a VH CDR1, VH CDR2, and VH CDR3 of the VH sequence shown in SEQ ID NO: 229; and/or a light chain variable (VL) region comprising VL CDR1, VL CDR2, and VL CDR3 of the VL sequence shown in SEQ ID NO: 228; and a second antibody variable domain comprising a heavy chain variable (VH) region comprising a VH CDR1, VH CDR2, and VH CDR3 of the VH sequence shown in SEQ ID NO:282; and/or a light chain variable (VL) region comprising a VL CDR1, VL CDR2, and VL CDR3 of the VL sequence shown in SEQ ID NO: 281.

In some embodiments, the second antibody variable domain comprises (a) a heavy chain variable (VH) region comprising (i) a VH complementary determining region one (CDR1) comprising the sequence shown in SEQ ID NO: 285, 286, or 287; (ii) a VH CDR2 comprising the sequence shown in SEQ ID NO: 288 or 289; and iii) a VH CDR3 comprising the sequence shown in SEQ ID NO: 290; and/or (b) a light chain variable (VL) region comprising (i) a VL CDR1 comprising the sequence shown in SEQ ID NO: 291; (ii) a VL CDR2 comprising the sequence shown in SEQ ID NO: 292; and (iii) a VL CDR3 comprising the sequence shown in SEQ ID NO: 234.

Table 3 shows the specific amino acid and nucleic acid sequences of the second antibody variable domain, which is specific to CD3. In Table 3, the underlined sequences are CDR sequences according to Kabat and in bold according to Chothia.

TABLE 3

| mAb | Light Chain | Heavy Chain |
|---|---|---|
| h2B4_HNPS_VL_TK | DIVMTQSPDSLAVSLGERATINC KSSQSLFNVRSRKNYLAWYQQK PGQPPKLLISWASTRESGVPDRF SGSGSGTDFTLTISSLQAEDVAV YYCKQSYDLFTFGSGTKLEIK (SEQ ID NO: 281) | EVQLVESGGGLVQPGGSLRLSCA ASGFTFSDYYMTWVRQAPGKGLE WVAFIRNRARGYTSDHNPSVKGR FTISRDNAKNSLYLQMNSLRAEDT AVYYCARDRPSYYVLDYWGQGTT VTVSS (SEQ ID NO: 282) |
| h2B4_HNPS_VL_TK | GACATTGTGATGACTCAATCCC CCGACTCCCTGGCTGTGTCCCT CGGCGAACGCGCAACTATCAAC TGTAAAAGCAGCCAGTCCCTGT TCAACGTCCGGTCGAGGAAGAA CTACCTGGCCTGGTATCAGCAG AAACCTGGGCAGCCGCCGAAG CTTCTGATCTCATGGGCCTCAA CTCGGGAAAGCGGAGTGCCAG ATAGATTCTCCGGATCTGGCTC CGGAACCGACTTCACCCTGACG ATTTCGAGCTTGCAAGCGGAGG ATGTGGCCGTGTACTACTGCAA GCAGTCCTACGACCTCTTCACC TTTGGTTCGGGCACCAAGCTGG AGATCAAA (SEQ ID NO: 283) | GAAGTCCAACTTGTCGAATCGGG AGGAGGCCTTGTGCAACCCGGT GGATCCCTGAGGCTGTCATGCG CGGCCTCGGGCTTCACCTTTTCC GATTACTACATGACCTGGGTCAG ACAGGCCCCTGGAAAGGGGTTG GAATGGGTGGCATTCATCCGGA ATAGAGCCCGCGGATACACTTCC GACCACAACCCCAGCGTGAAGG GGCGGTTCACCATTAGCCGCGA CAACGCCAAGAACTCCCTCTACC TCCAAATGAACAGCCTGCGGGC GGAGGATACCGCTGTGTACTACT GCGCCCGCGACCGGCCGTCCTA CTATGTGCTGGACTACTGGGGC CAGGGTACTACGGTCACCGTCT CCTCA (SEQ ID NO: 284) |

Table 4 shows the examples of CDR sequences of the second antibody variable domain, which is specific to CD3.

TABLE 4

| | Heavy Chain | | |
|---|---|---|---|
| mAb | CDRH1 | CDRH2 | CDRH3 |
| h2B4_HNPS_VL_TK | SDYYMT (SEQ ID NO: 285) (Kabat); GFTFSDY (SEQ ID NO: 286) (Chothia); GFTFSDYYMT (SEQ ID NO: 287) (Extended) | RNRARGYT (SEQ ID NO: 288) (Kabat) FIRNRARGYTSDHNPSVKG (SEQ ID NO: 289) (Extended) | DRPSYYVLDY (SEQ ID NO: 290) |

TABLE 4-continued

| | Light Chain | | |
|---|---|---|---|
| mAb | CDRH1 | CDRH2 | CDRH3 |
| h2B4_HNPS_VL_TK | KSSQSLFNVRSRKN YLA (SEQ ID NO: 291) | WASTRES (SEQ ID NO: 292) | KQSYDLFT (SEQ ID NO: 234) |

In some embodiments, a bispecific antibody provided herein which contains a CD3-specific variable domain having an anti-CD3 sequence as provided in U.S. Publication No. 20160297885, which is hereby incorporated by reference for all purposes.

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In another approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

In another approach, the bispecific antibodies are composed of amino acid modification in the first hinge region in one arm, and the substituted/replaced amino acid in the first hinge region has an opposite charge to the corresponding amino acid in the second hinge region in another arm. This approach is described in International Patent Application No. PCT/US2011/036419 (WO2011/143545).

In another approach, the formation of a desired heteromultimeric or heterodimeric protein (e.g., bispecific antibody) is enhanced by altering or engineering an interface between a first and a second immunoglobulin-like Fc region (e.g., a hinge region and/or a CH3 region). In this approach, the bispecific antibodies may be composed of a CH3 region, wherein the CH3 region comprises a first CH3 polypeptide and a second CH3 polypeptide which interact together to form a CH3 interface, wherein one or more amino acids within the CH3 interface destabilize homodimer formation and are not electrostatically unfavorable to homodimer formation. This approach is described in International Patent Application No. PCT/US2011/036419 (WO2011/143545).

In another approach, the bispecific antibodies can be generated using a glutamine-containing peptide tag engineered to the antibody directed to an epitope (e.g., FLT3) in one arm and another peptide tag (e.g., a Lys-containing peptide tag or a reactive endogenous Lys) engineered to a second antibody directed to a second epitope in another arm in the presence of transglutaminase. This approach is described in International Patent Application No. PCT/IB2011/054899 (WO2012/059882).

In some embodiments, the heterodimeric protein (e.g., bispecific antibody) as described herein comprises a full-length human antibody, wherein a first antibody variable domain of the bispecific antibody specifically binding to a target antigen (e.g., FLT3), and comprising a second antibody variable domain of the bispecific antibody capable of recruiting the activity of a human immune effector cell by specifically binding to an effector antigen (e.g., CD3) located on the human immune effector cell, wherein the first and second antibody variable domain of the heterodimeric protein comprise amino acid modifications at positions 223, 225, and 228 (e.g., (C223E or C223R), (E225E or E225R), and (P228E or P228R)) in the hinge region and at position 409 or 368 (e.g., K409R or L368E (EU numbering scheme)) in the CH3 region of human IgG2 (SEQ ID NO: 236).

In some embodiments, the first and second antibody variable domains of the heterodimeric protein comprise amino acid modifications at positions 221 and 228 (e.g., (D221R or D221E) and (P228R or P228E)) in the hinge region and at position 409 or 368 (e.g., K409R or L368E (EU numbering scheme)) in the CH3 region of human IgG1 (SEQ ID NO: 237).

In some embodiments, the first and second antibody variable domains of the heterodimeric protein comprise amino acid modifications at positions 228 (e.g., (P228E or P228R)) in the hinge region and at position 409 or 368 (e.g., R409 or L368E (EU numbering scheme)) in the CH3 region of human IgG4 (SEQ ID NO: 238).

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the FLT3 monospecific antibody or the FLT3 bispecific antibody (e.g., FLT3-CD3) as described herein is a monoclonal antibody. For example, the FLT3 monospecific antibody is a human monoclonal antibody. In another example, the FLT3 arm of the FLT3-CD3 bispecific antibody is a human monoclonal antibody, and the CD3 arm of the FLT3-CD3 bispecific antibody is a humanized monoclonal antibody.

In some embodiments, the antibody comprises a modified constant region, such as, for example without limitation, a constant region that has increased potential for provoking an immune response. For example, the constant region may be modified to have increased affinity to an Fc gamma receptor such as, e.g., FcγRI, FcγRIIA, or FcγIII.

In some embodiments, the antibody comprises a modified constant region, such as a constant region that is immunologically inert, that is, having a reduced potential for provoking an immune response. In some embodiments, the constant region is modified as described in Eur. J. Immunol., 29:2613-2624, 1999; PCT Application No. PCT/GB99/01441; and/or UK Patent Application No. 98099518. The Fc can be human IgG1, human IgG2, human IgG3, or human IgG4. The Fc can be human IgG2 containing the mutation A330P331 to S330S331 (IgG2Δa), in which the amino acid residues are numbered with reference to the wild type IgG2 sequence. Eur. J. Immunol., 29:2613-2624, 1999. In some embodiments, the antibody comprises a constant region of IgG4 comprising the following mutations (Armour et al., Molecular Immunology 40 585-593, 2003): E233F234L235 to P233V234A235 (IgG4Δc), in which the numbering is with reference to wild type IgG4. In yet another embodiment, the Fc is human IgG4 E233F234L235 to P233V234A235 with deletion G236 (IgG4Δb). In another embodiment, the Fc is any human IgG4 Fc (IgG4, IgG4Ab or IgG4Δc) containing hinge stabilizing mutation S228 to P228 (Aalberse et al., Immunology 105, 9-19, 2002). In another embodiment, the Fc can be aglycosylated Fc.

In some embodiments, the constant region is aglycosylated by mutating the oligosaccharide attachment residue (such as Asn297) and/or flanking residues that are part of the glycosylation recognition sequence in the constant region. In some embodiments, the constant region is aglycosylated for N-linked glycosylation enzymatically. The constant region may be aglycosylated for N-linked glycosylation enzymatically or by expression in a glycosylation deficient host cell.

In some embodiments, the constant region has a modified constant region that removes or reduces Fc gamma receptor binding. For example, the Fc can be human IgG2 containing the mutation D265, in which the amino acid residues are numbered with reference to the wild type IgG2 sequence (SEQ ID NO: 236). Accordingly, in some embodiments, the constant region has a modified constant region having the sequence shown in SEQ ID NO: 239:

ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCRVRCPRCPAPPVAGPSVFLFPPKPKDTLMISRTPEVTCVVVAVSHEDP

EVQFNWYVDGVEVHNAKTKPREEQFNSTFRVVSVLTVVHQDWLNGKEYKC

KVSNKGLPSSIEKTISKTKGQPREPQVYTLPPSREEMTKNQVSLTCLVKG

FYPSDIAVEWESNGQPENNYKTTPPMLDSDGSFFLYSRLTVDKSRWQQGN

VFSCSVMHEALHNHYTQKSLSLSPGK.

And the nucleic acid encoding the sequence shown in SEQ ID NO: 239 is shown in SEQ ID NO: 240.

In some embodiments, the constant region has a modified constant region having the sequence shown in SEQ ID NO: 241:

ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCEVECPECPAPPVAGPSVFLFPPKPKDTLMISRTPEVTCVVVAVSHEDP

EVQFNWYVDGVEVHNAKTKPREEQFNSTFRVVSVLTVVHQDWLNGKEYKC

KVSNKGLPSSIEKTISKTKGQPREPQVYTLPPSREEMTKNQVSLTCEVKG

FYPSDIAVEWESNGQPENNYKTTPPMLDSDGSFFLYSKLTVDKSRWQQGN

VFSCSVMHEALHNHYTQKSLSLSPGK.

And the nucleic acid encoding the sequence shown in SEQ ID NO: 241 is shown in SEQ ID NO: 242.

The amino acid of the human Kappa constant region is shown in SEQ ID NO: 243: GTVAAPSVFIFPPSD-EQLKSGTASVVCLLNNFYPREAKVQWKVD-NALQSGNSQESVT EQDSKDSTYSLSSTLTL-SKADYEKHKVYACEVTHQGLSSPVTKSFNRGEC.

And the nucleic acid encoding the sequence of SEQ ID NO: 243 is shown in SEQ ID NO: 244.

One way of determining binding affinity of antibodies to FLT3 is by measuring binding affinity of the bivalent antibody to monomeric FLT3 protein. The affinity of an FLT3 antibody can be determined by surface plasmon resonance (Biacore™3000™ surface plasmon resonance (SPR) system, Biacore™, INC, Piscataway NJ) equipped with pre-immobilized anti-mouse Fc or anti-human Fc using HBS-EP running buffer (0.01M HEPES, pH 7.4, 0.15 NaCl, 3 mM EDTA, 0.005% v/v Surfactant P20). Monomeric 8-histidine tagged human FLT3 extracellular domain can be diluted into HBS-EP buffer to a concentration of less than 0.5 μg/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound FLT3 protein while keeping the activity of FLT3 antibodies on the chip for over 200 injections. Typically, serial dilutions (spanning concentrations of 0.1-10× estimated $K_D$) of purified 8-histidine tagged FLT3 samples are injected for 1 min at 100 μL/minute and dissociation times of up to 2 hours are allowed. The concentrations of the FLT3 proteins are determined by absorbance at 280 nm based on sequence specific extinction coefficient of the 8-histidine tagged FLT3 protein. Kinetic association rates ($k_{on}$ or $k_a$) and dissociation rates ($k_{off}$ or $k_d$) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $K_{off}/K_{on}$. This protocol is suitable for use in determining binding affinity of an antibody to any monomeric FLT3, including human FLT3, FLT3 of another mammal (such as mouse FLT3, rat FLT3, or primate FLT3), as well as different forms of FLT3 (e.g., glycosylated FLT3). Binding affinity of an antibody is generally measured at 25° C., but can also be measured at 37° C.

The antibodies as described herein may be made by any method known in the art. For the production of hybridoma cell lines, the route and schedule of immunization of the host animal are generally in keeping with established and conventional techniques for antibody stimulation and production, as further described herein. General techniques for production of human and mouse antibodies are known in the art and/or are described herein.

It is contemplated that any mammalian subject including humans or antibody producing cells therefrom can be manipulated to serve as the basis for production of mammalian, including human and hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., Nature 256:495-497, 1975 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for FLT3, or portions thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with cells expressing human FLT3, a human FLT3 protein, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

If desired, the antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., J. Immunol. Methods 329, 112, 2008; U.S. Pat. No. 7,314,622.

In an alternative, the polynucleotide sequence may be used for genetic manipulation to "humanize" the antibody or to improve the affinity, or other characteristics of the antibody. For example, the constant region may be engineered to more nearly resemble human constant regions to avoid immune response if the antibody is used in clinical trials and treatments in humans. It may be desirable to genetically manipulate the antibody sequence to obtain greater affinity to FLT3 and greater efficacy in inhibiting FLT3.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen binding site derived from a non-human immunoglobulin have been described, including chimeric antibodies having rodent or modified rodent V regions and their associated CDRs fused to human constant regions. See, for example, Winter et al. Nature 349:293-299, 1991, Lobuglio et al. Proc. Nat. Acad. Sci. USA 86:4220-4224, 1989, Shaw et al. J Immunol. 138:4534-4538, 1987, and Brown et al. Cancer Res. 47:3577-3583, 1987. Other references describe rodent CDRs grafted into a human supporting framework region (FR) prior to fusion with an appropriate human antibody constant region. See, for example, Riechmann et al. Nature 332:323-327, 1988, Verhoeyen et al. Science 239:1534-1536, 1988, and Jones et al. Nature 321: 522-525, 1986. Another reference describes rodent CDRs supported by recombinantly engineered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. PCT/GB99/01441; UK Patent Application No. 9809951.8. Other methods of humanizing antibodies that may also be utilized are disclosed by Daugherty et al., Nucl. Acids Res. 19:2471-2476, 1991, and in U.S. Pat. Nos. 6,180,377; 6,054,297; 5,997,867; 5,866,692; 6,210, 671; and 6,350,861; and in PCT Publication No. WO 01/27160.

The general principles related to humanized antibodies discussed above are also applicable to customizing antibodies for use, for example, in dogs, cats, primate, equines and bovines. Further, one or more aspects of humanizing an antibody described herein may be combined, e.g., CDR grafting, framework mutation and CDR mutation.

In one variation, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, CA) and HuMAb-Mouse® and TC Mouse™ from Medarex, Inc. (Princeton, NJ).

In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743; and 6,265,150; and Winter et al., Annu. Rev. Immunol. 12:433-455, 1994. Alternatively, the phage display technology (McCafferty et al., Nature 348: 552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597, 1991, or Griffith et al., EMBO J. 12:725-734, 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783, 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for FLT3, or tumor antigens of interest.

The antibodies as described herein can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses, and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant regions in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of a monoclonal antibody herein.

The FLT3 antibodies as described herein can be identified or characterized using methods known in the art, whereby reduction of FLT3 expression levels are detected and/or measured. In some embodiments, an FLT3 antibody is identified by incubating a candidate agent with FLT3 and monitoring binding and/or attendant reduction of FLT3 expression levels. The binding assay may be performed with purified FLT3 polypeptide(s), or with cells naturally expressing, or transfected to express, FLT3 polypeptide(s). In one embodiment, the binding assay is a competitive binding assay, where the ability of a candidate antibody to compete with a known FLT3 antibody for FLT3 binding is evaluated. The assay may be performed in various formats, including the ELISA format.

Following initial identification, the activity of a candidate FLT3 antibody can be further confirmed and refined by bioassays, known to test the targeted biological activities. Alternatively, bioassays can be used to screen candidates directly. Some of the methods for identifying and characterizing antibodies are described in detail in the Examples.

FLT3 antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, New York, 1999. In an additional example, epitope mapping can be used to determine the sequence to which an antibody binds. Epitope mapping is commercially available from various sources, for example, Pepscan Systems (Edelhertweg 15, 8219 P H Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an FLT3 or other tumor antigen antibody. In another example, the epitope to which the FLT3 antibody binds can be determined in a systematic screening by using overlapping peptides derived from the FLT3 sequence and determining binding by the FLT3 antibody. According to the gene fragment expression assays, the open reading frame encoding FLT3 is fragmented either randomly or by specific genetic constructions and the reactivity of the expressed fragments of FLT3 with the antibody to be tested is determined. The gene fragments may, for example, be produced by PCR and then transcribed and translated into protein in vitro, in the presence of radioactive amino acids. The binding of the antibody to the radioactively labeled FLT3 is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant FLT3 in which various fragments of the FLT3 protein have been replaced (swapped) with sequences from FLT3 from another species (e.g., mouse), or a closely related, but antigenically distinct protein. By assessing binding of the antibody to the mutant FLT3, the importance of the particular FLT3 fragment to antibody binding can be assessed. In the case of FLT3 specific antibody (i.e. antibody that does not bind FLT3wt (wild type) or any other proteins), epitope can be deduced from the sequence alignment of FLT3 to FLT3 wt.

Yet another method which can be used to characterize an FLT3 antibody is to use competition assays with other antibodies known to bind to the same antigen, i.e., various fragments on FLT3, to determine if the FLT3 antibody binds to the same epitope as other antibodies. Competition assays are well known to those of skill in the art.

An expression vector can be used to direct expression of an FLT3 antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 263:621, 1988; Wu et al., J. Biol. Chem., 269:542, 1994; Zenke et al., Proc. Natl. Acad. Sci. USA, 87:3655, 1990; and Wu et al., J. Biol. Chem., 266:338, 1991. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1:51, 1994; Kimura, Human Gene Therapy, 5:845, 1994; Connelly, Human Gene Therapy, 1995, 1:185; and Kaplitt, Nature Genetics, 6:148, 1994). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Pat. No. 2,200,651; and EP Pat. No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 3:147, 1992); ligand-linked DNA (see, e.g., Wu, J. Biol. Chem., 264:16985, 1989); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 14:2411, 1994 and in Woffendin, Proc. Natl. Acad. Sci., 91:1581, 1994.

In some embodiments, the invention encompasses compositions, including pharmaceutical compositions, comprising antibodies described herein or made by the methods and having the characteristics described herein. As used herein, compositions comprise one or more antibodies that bind to FLT3, and/or one or more polynucleotides comprising sequences encoding one or more these antibodies. These compositions may further comprise suitable excipients, such as pharmaceutically acceptable excipients including buffers, which are well known in the art.

The invention also provides methods of making any of these antibodies. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In another alternative, the antibodies can be made recombinantly using procedures that are well known in the art. In one embodiment, a polynucleotide comprises a sequence encoding the heavy chain and/or the light chain variable regions of antibody P4F6, P4C7, P3A', P5A3, P9B5, P9F1, P1B4, P1B11, P7H3, P3E10, P1A5, P5F7, P4H11, P15F7, P12B6, P8B6, P14G2, P7F9, P08B06EE, P04A04, P01A05, P08B03, P5F7, P5F7g, P10A02g, P10A04g, P10A05g, P10A07g, P10B03g, P10B06g, P5F7g2, P5F7g3, or P5F7g4. The sequence encoding the antibody of interest may be maintained in a vector in a host cell and the host cell can then be expanded and frozen for future use. Vectors (including expression vectors) and host cells are further described herein.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

In the recombinant humanized antibodies, the Fcγ portion can be modified to avoid interaction with Fcγ receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, for example, U.S. Pat. Nos. 5,997,867 and 5,866,692.

The invention encompasses modifications to the antibodies and polypeptides of the invention including variants shown in Table 5, including functionally equivalent antibodies which do not significantly affect their properties and variants which have enhanced or decreased activity and/or affinity. For example, the amino acid sequence may be mutated to obtain an antibody with the desired binding affinity to FLT3. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 5 under the heading of "conservative substitutions." If such substitutions result in a change in biological activity, then more substantial changes, denominated "exemplary substitutions" in Table 5, or as further described below in reference to amino acid classes, may be introduced and the products screened. In some embodiments, substitution variants of antibodies provided herein have no more than 15, 14, 13, 12, 11, 10, 9, 8, 7, 6, 5, 4, 3, 2, or 1 conservative substitution in the VH or VL region as compared to the reference parent antibody. In some embodiments, the substitutions are not within a CDR of the VH or VL region.

TABLE 5

Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |

TABLE 5-continued

Amino Acid Substitutions

| Original Residue (naturally occurring amino acid) | Conservative Substitutions | Exemplary Substitutions |
|---|---|---|
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring amino acid residues are divided into groups based on common side-chain properties:

(1) Non-polar: Norleucine, Met, Ala, Val, Leu, Ile,
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDR H3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, Chem. Immunol. 65:111-128, 1997; Wright and Morrison, TibTECH 15:26-32, 1997). The oligosaccharide side chains of the immunoglobulins affect the protein's function (Boyd et al., Mol. Immunol. 32:1311-1318, 1996; Wittwe and Howard, Biochem. 29:4175-4180, 1990) and the intramolecular interaction between portions of the glycoprotein, which can affect the conformation and presented three-dimensional surface of the glycoprotein (Jefferis and Lund, supra; Wyss and Wagner, Current Opin. Biotech. 7:409-416, 1996). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., Mature Biotech. 17:176-180, 1999).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., J. Biol. Chem. 272:9062-9070, 1997).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

The invention includes affinity matured embodiments. For example, affinity matured antibodies can be produced by procedures known in the art (Marks et al., Bio/Technology, 10:779-783, 1992; Barbas et al., Proc Nat. Acad. Sci, USA 91:3809-3813, 1994; Schier et al., Gene, 169:147-155, 1995; Yelton et al., J. Immunol., 155:1994-2004, 1995; Jackson et al., J. Immunol., 154(7):3310-9, 1995, Hawkins et al., J. Mol. Biol., 226:889-896, 1992; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using Biacore™ surface plasmon resonance analysis, which detects differences in binding affinity of about 2-fold or greater. Biacore™ is particularly useful when the starting antibody already binds with a relatively high affinity, for example a $K_D$ of about 10 nM or lower. Screening using Biacore™ surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., Gene 137(1):109-18, 1993.

The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore™ surface plasmon resonance analysis, and selection using any method known in the art for selection, including phage display, yeast display, and ribosome display.

The invention also encompasses fusion proteins comprising one or more fragments or regions from the antibodies of this invention. In one embodiment, a fusion polypeptide is provided that comprises at least 10 contiguous amino acids of the variable light chain region shown in SEQ ID NOs: 1, 3, 5, 7, 9, 11, 13, 15, 17, 19, 21, 23, 25, 27, 29, 31, 33, 35, 204, 206, 208, 210, 212, 214, 216, 218, 220, 222, 224, 226, 228, 230, or 232, and/or at least 10 amino acids of the variable heavy chain region shown in SEQ ID NOs: 2, 4, 6, 8, 10, 12, 14, 16, 18, 20, 22, 24, 26, 28, 30, 32, 34, 36, 205, 207, 209, 211, 213, 215, 217, 219, 221, 223, 225, 227, 229, 231, or 233. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises one or more CDR(s). In still other embodiments, the fusion polypeptide comprises CDR H3 (VH CDR3) and/or CDR L3 (VL CDR3). For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

A fusion polypeptide can be created by methods known in the art, for example, synthetically or recombinantly. Typically, the fusion proteins of this invention are made by preparing an expressing a polynucleotide encoding them using recombinant methods described herein, although they may also be prepared by other means known in the art, including, for example, chemical synthesis.

This invention also provides compositions comprising antibodies conjugated (for example, linked) to an agent that facilitate coupling to a solid support (such as biotin or avidin). For simplicity, reference will be made generally to antibodies with the understanding that these methods apply to any of the FLT3 antibody embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The invention also provides isolated polynucleotides encoding the antibodies of the invention, and vectors and host cells comprising the polynucleotide.

Accordingly, the invention provides polynucleotides (or compositions, including pharmaceutical compositions), comprising polynucleotides encoding any of the following: P4F6, P4C7, P3A, P5A3, P9B5, P9F1, P1B4, P1B11, P7H3, P3E10, P1A5, P5F7, P4H11, P15F7, P12B6, P8B6, P14G2, P7F9, P08B06EE, P04A04, P01A05, P08b03, P5F7, P5F7g, P10A02g, P10A04g, P10A05g, P10A07g, P10B03g, P10B06g, P5F7g2, P5F7g3, P5F7g4, or any fragment or part thereof having the ability to bind FLT3.

In another aspect, the invention provides polynucleotides encoding any of the antibodies (including antibody fragments) and polypeptides described herein, such as antibodies and polypeptides having impaired effector function. Polynucleotides can be made and expressed by procedures known in the art.

In another aspect, the invention provides compositions (such as a pharmaceutical compositions) comprising any of the polynucleotides of the invention. In some embodiments, the composition comprises an expression vector comprising a polynucleotide encoding any of the antibodies described herein.

Expression vectors, and administration of polynucleotide compositions are further described herein.

In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425;

Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as E. coli or B. subtillis) and yeast (such as S. cerevisae, S. pombe; or K. lactis). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to FLT3 is effected by an immunoassay or FACS. A cell overexpressing the antibody or protein of interest can be identified.

Methods of Using the FLT3 Antibodies

The antibodies of the present invention are useful in various applications including, but are not limited to, therapeutic treatment methods and diagnostic treatment methods.

The antibodies (e.g., monospecific and bispecific) obtained by the methods described above can be used as a medicament. In some embodiments, such a medicament can be used for treating cancer. In some embodiments, the cancer is a cancer of hematopoietic origin, such as a lymphoma or leukemia. In some embodiments, the cancer is multiple myeloma malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macrogbulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, or other hematopoietic cells related cancers. In a preferred embodiment the cancer is AML. In a preferred embodiment the cancer is ALL.

In some embodiments, provided is a method of inhibiting tumor growth or progression in a subject who has malignant cells expressing FLT3, comprising administering to the subject in need thereof an effective amount of a composition comprising the FLT3 antibodies (e.g., FLT3-CD3 bispecific antibodies) as described herein. In other embodiments, provided is a method of inhibiting metastasis of cells expressing FLT3 in a subject, comprising administering to the subject in need thereof an effective amount of a composition comprising the FLT3 antibodies (e.g., FLT3-CD3 bispecific antibodies) as described herein. In other embodiments, provided is a method of inducing tumor regression in malignant cells in a subject, comprising administering to the subject in need thereof an effective amount of a composition comprising the FLT3 antibodies (e.g., FLT3-CD3 bispecific antibodies) as described herein.

In some embodiments, the antibody (e.g., FLT3-CD3 bispecific antibody) according to the invention can be used in the manufacture of a medicament for treatment of a cancer in a patient in need thereof.

In some embodiments, the treatment can be in combination with one or more therapies against a cancer selected from the group consisting of antibodies therapy, chemotherapy, cytokines therapy, targeted therapy, vaccine therapy, dendritic cell therapy, gene therapy, hormone therapy, surgical resection, laser light therapy, and radiation therapy.

In some embodiments, the cytokine used in the cytokine therapy is interleukin (IL)-1, 2, 3, 4, 5, 6, 7, 8, 9, 10, 11, 12, 13, 14, 15, 16, or 17. In some embodiments, the cytokine is IL-15, IL-12, or IL-2. For example, the FLT3 antibodies (e.g., FLT3-CD3 bispecific antibodies) of the present invention are administered to a patient in conjunction with (e.g., before, simultaneously or following) with a wild-type IL-15 (e.g., Accession number: >spIP40933|49-162 or SEQ ID NO: 293).

In some embodiments, the FLT3 antibodies (e.g., FLT3-CD3 bispecific antibodies) of the present invention are administered to a patient in conjunction with (e.g., before, simultaneously or following) treatment with a biotherapeutic agent, for example, an antibody, including but not limited to, an anti-CTLA-4 antibody, an anti-4-1BB antibody (e.g., PF-04518600), an anti-PD-1 antibody (e.g., nivolumab, pembrolizumab, or PF-06801591), an anti-PD-L1 antibody (e.g., avelumab, atezolizumab, or durvalumab), an anti-TIM3 antibody, an anti-LAG3 antibody, an anti-TIGIT antibody, an anti-OX40 antibody, an IL-8 antibody, an anti-HVEM antibody, an anti-BTLA antibody, an anti-CD40 antibody, an anti-CD40L antibody, anti-CD47 antibody, an anti-CSF1R antibody, an anti-CSF1 antibody, an anti-MARCO antibody, an anti-CXCR4 antibodies, an anti-VEGFR1 antibody, an anti-VEGFR2 antibody, an anti-TNFR1 antibody, an anti-MCSF antibody (e.g., PD-0360324), an anti-TNFR2 antibody, an anti-CD3 bispecific antibody, an anti-CD19 antibody, an anti-CD20, an anti-Her2 antibody, an anti-EGFR antibody, an anti-ICOS antibody, an anti-CD22 antibody, an anti-CD 52 antibody, an anti-CCR4 antibody, an anti-CCR8 antibody, an anti-CD200R antibody, an anti-VISG4 antibody, an anti-CCR2 antibody, an anti-LILRb2 antibody, an anti-CXCR4 antibody, an anti-CD206 antibody, an anti-CD163 antibody, an anti-KLRG1 antibody, an anti-B7-H4 antibody, an anti-B7-H3 antibody, or an anti-GITR antibody.

In some embodiments, the FLT3 antibodies (e.g., FLT3-CD3 bispecific antibodies) of the present invention are administered to a patient in conjunction with (e.g., before, simultaneously or following) treatment with a CCR2 antagonist (e.g., INC-8761), an antiviral agent, cidofovir and interleukin-2, Cytarabine (also known as ARA-C) or nataliziimab treatment for MS patients or efaliztimab treatment for psoriasis patients or other treatments for PML patients. In some embodiments, the FLT3 antibodies (e.g., FLT3-CD3 bispecific antibodies) of the present invention may be used in combination with chemotherapy, radiation, immunosuppressive agents (such as cyclosporin, azathioprine, methotrexate, mycophenolate, and FK506) or other immunoablative agents such as CAMPATH, cytotoxin, fludaribine, cyclosporin, FK506, rapamycin, mycoplienolic acid, steroids, FR901228, cytokines, and/or irradiation. These drugs inhibit either the calcium dependent phosphatase calcineurin (cyclosporine and FK506) or inhibit the p70S6 kinase that is important for growth factor induced signaling (rapamycin). In further embodiments, the FLT3 antibodies (e.g., FLT3-CD3 bispecific antibodies) of the present invention may be used in combination with kinase inhibitors, including but not limited to, mTOR inhibitors, midostaurin, lestaurtinib, sorafenib, sunitinib, quizartinib, ponatinib, crenolanib, palbociclib, and gilteritinib.

In some embodiments, the FLT3 antibodies (e.g., FLT3-CD3 bispecific antibodies) of the present invention may also be used in combination with epigenetic modulators, proteasome inhibitors, immunomodulatory agents (e.g., lenalidomide), Hedgehog inhibitors, TNFα (Tumor Necrosis Factor alpha), PAP (Phosphatidic Acid Phosphatase) inhibitors, oncolytic viruses, IDO (Indoleamine-Pyrrole 2,3-Dioxygenase) inhibitors, glutaminase GLS1 inhibitors, tumor vaccines, TLR (Toll-Like Receptor) agonists (e.g., TLR3, TLR4, TLR5, TLR7, or TLR9), or Isocitrate Dehydrogenase (IDH) inhibitors.

In a further embodiment, the FLT3 antibodies (e.g., FLT3-CD3 bispecific antibodies) of the present invention are administered to a patient in conjunction with (e.g., before, simultaneously or following) bone marrow transplantation, CART (Chimeric Antigen Receptor T) cells, T cell ablative therapy using either chemotherapy agents such as, fludarabine, external-beam radiation therapy (XRT), cyclophosphamide, or antibodies such as OKT3 or alemtuzumab.

The administration of the antibodies (e.g., monospecific or bispecific) according to the invention may be carried out in any convenient manner, including by aerosol inhalation, injection, ingestion, transfusion, implantation or transplantation. The compositions described herein may be administered to a patient subcutaneously, intradermally, intratumorally, intracranially, intranodally, intramedullary, intramuscularly, by intravenous or intralymphatic injection, or intraperitoneally. In one embodiment, the antibody compositions of the invention are preferably administered by intravenous injection.

In some embodiments, the administration of the antibodies (e.g., monospecific or bispecific) can comprise administration of, for example, about 0.01 to about 20 mg per kg body weight including all integer values of mg per kg within those ranges. In some embodiments, the administration of the antibodies can comprise administration of about 0.1 to 10 mg per kg body weight including all integer values of mg per kg within those ranges. The antibody can be administrated in one or more doses. In some embodiments, said effective amount of the antibody can be administrated as a single dose. In some embodiments, said effective amount of antibodies can be administrated as more than one dose over a period time. Timing of administration is within the judgment of managing physician and depends on the clinical condition of the patient. While individual needs vary, determination of optimal ranges of effective amounts of a given antibody (e.g., monospecific or bispecific) for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired. In some embodiments, an effective amount of heteromultimeric antibody or composition comprising those antibodies are administrated parenterally. In some embodiments, administration can be an intravenous administration. In some embodiments, administration can be directly done by injection within a tumor.

In some embodiments, anti-FLT3 antibodies provided herein may be used for diagnostic purposes, such in assays to identify FLT3 protein in samples (e.g. in immunohistochemistry assays) or in patients.

Compositions

In one aspect, the present invention provides a pharmaceutical composition comprising an antibody (e.g., monospecific or bispecific) of the invention or portion thereof as described above in a pharmaceutically acceptable carrier. In certain embodiments, the polypeptides of the invention may be present in a neutral form (including zwitter ionic forms) or as a positively or negatively-charged species. In some embodiments, the polypeptides may be complexed with a counterion to form a "pharmaceutically acceptable salt," which refers to a complex comprising one or more polypeptides and one or more counterions, where the counterions are derived from pharmaceutically acceptable inorganic and organic acids and bases.

The antibody (e.g., monospecific or bispecific) or portions thereof, may be administered alone or in combination with one or more other polypeptides of the invention or in combination with one or more other drugs (or as any combination thereof). The pharmaceutical compositions, methods and uses of the invention thus also encompass embodiments of combinations (co-administration) with other active agents, as detailed below.

As used herein, the terms "co-administration," "co-administered" and "in combination with," referring to the antibodies of the invention and one or more other therapeutic agents, is intended to mean, and does refer to and include the following: (i) simultaneous administration of such combination of an antibody disclosed herein and therapeutic agent(s) to a patient in need of treatment, when such components are formulated together into a single dosage form which releases said components at substantially the same time to said patient; (ii) substantially simultaneous administration of such combination of an antibody disclosed herein and therapeutic agent(s) to a patient in need of treatment, when such components are formulated apart from each other into separate dosage forms which are taken at substantially the same time by said patient, whereupon said components are released at substantially the same time to said patient; (iii) sequential administration of such combination of an antibody disclosed herein and therapeutic agent(s) to a patient in need of treatment, when such components are formulated apart from each other into separate dosage forms which are taken at consecutive times by said patient with a significant time interval between each administration, whereupon said components are released at substantially different times to said patient; and (iv) sequential administration of such combination of an antibody disclosed herein and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

Generally, the antibody (e.g., monospecific or bispecific) disclosed herein or portions thereof are suitable to be administered as a formulation in association with one or more pharmaceutically acceptable excipient(s). The term 'excipient' is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. Any method for administering peptides, proteins or antibodies accepted in the art may suitably be employed for the heterodimeric proteins and portions thereof disclosed herein.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Preferred embodiments include the intravenous and the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include controlled, delayed, sustained, pulsed, targeted and programmed release formulations. For example, in one aspect, sterile injectable solutions can be prepared by incorporating the heterodimeric protein, e.g., bispecific antibody, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

Generally, for administration of the antibodies described herein (monospecific or bispecific), the candidate dosage can be administered daily, every week, every other week, every three weeks, every four weeks, every five weeks, every six weeks, every seven weeks, every eight weeks, every ten weeks, every twelve weeks, or more than every twelve weeks. For repeated administrations over several days or longer, depending on the condition, the treatment is sustained until a desired suppression of symptoms occurs or until sufficient therapeutic levels are achieved, for example, to reduce symptoms associated with cancer. The progress of this therapy is easily monitored by conventional techniques and assays. The dosing regimen (including the anti-FLT monospecific or bispecific antibody used) can vary over time.

In some embodiments, the candidate dosage is administered daily with the dosage ranging from about any of 1 µg/kg to 30 µg/kg to 300 µg/kg to 3 mg/kg, to 30 mg/kg, to 100 mg/kg or more, depending on the factors mentioned above. For example, daily dosage of about 0.01 mg/kg, about 0.03 mg/kg, about 0.1 mg/kg, about 0.3 mg/kg, about 1 mg/kg, about 2.5 mg/kg, about 3 mg/kg, about 5 mg/kg, about 10 mg/kg, about 15 mg/kg, and about 25 mg/kg may be used.

In some embodiments, the candidate dosage is administered every week with the dosage ranging from about any of 1 µg/kg to 30 µg/kg to 300 µg/kg to 3 mg/kg, to 30 mg/kg, to 100 mg/kg or more, depending on the factors mentioned above. For example, a weekly dosage of about 0.01 mg/kg, about 0.03 mg/kg, about 0.1 mg/kg, about 0.3 mg/kg, about 0.5 mg/kg, about 1 mg/kg, about 2.5 mg/kg, about 3 mg/kg, about 5 mg/kg, about 10 mg/kg, about 15 mg/kg, about 25 mg/kg, and about 30 mg/kg may be used.

In some embodiments, the candidate dosage is administered every two weeks with the dosage ranging from about any of 1 µg/kg to 30 µg/kg to 300 µg/kg to 3 mg/kg, to 30 mg/kg, to 100 mg/kg or more, depending on the factors mentioned above. For example, a bi-weekly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, and about 30 mg/kg may be used.

In some embodiments, the candidate dosage is administered every three weeks with the dosage ranging from about any of 1 µg/kg to 30 µg/kg to 300 µg/kg to 3 mg/kg, to 30 mg/kg, to 100 mg/kg or more, depending on the factors mentioned above. For example, a tri-weekly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, about 30 mg/kg, about 35 mg/kg, about 40 mg/kg, about 45 mg/kg, and about 50 mg/kg may be used.

In some embodiments, the candidate dosage is administered every month or every four weeks with the dosage ranging from about any of 1 µg/kg to 30 µg/kg to 300 µg/kg to 3 mg/kg, to 30 mg/kg, to 100 mg/kg or more, depending on the factors mentioned above. For example, a monthly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, about 30 mg/kg, about 35 mg/kg, about 40 mg/kg, about 45 mg/kg, and about 50 mg/kg may be used.

In other embodiments, the candidate dosage is administered daily with the dosage ranging from about 0.01 mg to about 1200 mg or more, depending on the factors mentioned above. For example, daily dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, or about 1200 mg may be used.

In other embodiments, the candidate dosage is administered every week with the dosage ranging from about 0.01 mg to about 2000 mg or more, depending on the factors mentioned above. For example, weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg may be used.

In other embodiments, the candidate dosage is administered every two weeks with the dosage ranging from about 0.01 mg to about 2000 mg or more, depending on the factors mentioned above. For example, bi-weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg may be used.

In other embodiments, the candidate dosage is administered every three weeks with the dosage ranging from about 0.01 mg to about 2500 mg or more, depending on the factors mentioned above. For example, tri-weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, or about 2500 mg may be used.

In other embodiments, the candidate dosage is administered every four weeks or month with the dosage ranging from about 0.01 mg to about 3000 mg or more, depending on the factors mentioned above. For example, monthly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500, about 2600 mg, about 2700 mg, about 2800 mg, about 2900 mg, or about 3000 mg may be used.

Kits

The invention also provides kits for use in the instant methods. Kits of the invention include one or more containers comprising the antibody (e.g., monospecific or bispecific) as described herein and instructions for use in accordance with any of the methods of the invention described herein. Generally, these instructions comprise a description of administration of the antibody protein for the above described therapeutic treatments.

The instructions relating to the use of the antibody (e.g., monospecific or bispecific) as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a bispecific antibody. The container may further comprise a second pharmaceutically active agent.

Kits may optionally provide additional components such as buffers and interpretive information. Normally, the kit comprises a container and a label or package insert(s) on or associated with the container.

Biological Deposit

Representative materials of the present invention were deposited in the American Type Culture Collection, 10801 University Boulevard, Manassas, Va. 20110-2209, USA, on Jun. 1, 2017. Vector P5F7g2-VL having ATCC Accession No. PTA-124230 is a polynucleotide encoding the P5F7g2 light chain variable region, and vector P5F7g2-VH having ATCC Accession No. PTA-124229 is a polynucleotide encoding the P5F7g2 heavy chain variable region. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. § 122 and the Commissioner's rules pursuant thereto (including 37 C.F.R. § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Reference is also made to a material disclosed herein and deposited in the American Type Culture Collection, 10801 University Boulevard, Manassas, Va. 20110-2209, USA, on Jun. 1, 2017. Vector PE310-VL having ATCC Accession No. PTA-124228 is a polynucleotide encoding the PE310 light chain variable region, and vector P3E10-VH having ATCC Accession No. PTA-124227 is a polynucleotide encoding the PE310 heavy chain variable region. The deposits were also made under the provisions of the Budapest Treaty, in accordance with the terms and conditions thereof as summarized above.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1: Determination of Kinetics and Affinity of Human FLT3/ FLT3 Antibodies Interactions at 37° C.

This example determines the kinetics and affinity of various anti-FLT3 antibodies at 37° C. All experiments were performed on a Biacore T200 surface Plasmon resonance biosensor (GE Lifesciences, Piscataway NJ).

The sensor chip preparation was performed at 25° C. with a running buffer of 10 mM HEPES, 150 mM NaCl, 0.05% (v/v) Tween-20, pH 7.4. An anti-human Fc sensor chip was made by activating all flow cells of a Biacore CM4 sensor chip with a 1:1 (v/v) mixture of 400 mM EDC and 100 mM NHS for 7 minutes, at a flow rate of 10 μL/min. An anti-human Fc reagent (Goat Anti-Human IgG Fc, Southern Biotech Catalog #2081-01) was diluted to 30 μg/mL in 10 mM Sodium Acetate pH 4.5 and injected on all flow cells for 7 minutes at 20 μL/min. All flow cells were blocked with 100 mM ethylenediamine in 150 mM Borate buffer pH 8.5 for 7 minutes at 10 μL/min.

The experiments were performed at 37° C. using a running buffer of 10 mM HEPES, 150 mM NaCl, 0.05% (v/v) Tween-20, pH 7.4, 1 mg/mL BSA. FLT3 antibodies were captured from undiluted supernatants onto downstream flow cells (flow cells 2, 3 and 4) at a flow rate of 10 μL/min for 1 minute. Different antibodies were captured on each flow cell. Flow cell 1 was used as a reference surface. Following capture of FLT3 antibodies, analyte (buffer, hFLT3) was injected at 30 μL/min on all flow cells for two minutes. After the analyte injection, dissociation was monitored for 10 minutes followed by regeneration of all flow cells with three 1-minute injections of 75 mM Phosphoric Acid. For each captured FLT3 antibody, the following analyte injections were performed: buffer, 11 nM hFLT3, 33 nM hFLT3, 100 nM hFLT3 and 300 nM hFLT3. Buffer cycles were collected for each captured FLT3 antibody for double-referencing purposes (double-referencing as described in Myszka, D. G. Improving biosensor analysis. *J. Mol. Recognit.* 12, 279-284 (1999)). The double-referenced sensorgrams were fit globally to a simple 1:1 Langmuir with mass transport binding model.

The kinetics and affinity parameters for tested anti-FLT3 antibodies are shown in Tables 6.

Example 2: T-Cell Mediated Killing of AML Cell Lines Using Flt3-CD3 Bispecific IgG Targeting Domain 4 In Vitro This example illustrates the in vitro cytotoxicity of the Anti-Flt3/CD3 hIgG2ΔA_D265A Bispecific in Flt3 Positive Cells.

Human anti-Flt3 (P5F7p, P5F7g2, P5F7g2, P5F7g3, P5F7g4) and human anti-CD3 (h2B4-VH-hnps VL-TK ("H2B4")) antibodies were expressed as human IgG2dA_D265A engineered with EEEE on one arm and RRRR on the other arm for bispecific exchange at positions 223, 225, and 228 (e.g., (C223E or C223R), (E225E or E225R), and (P228E or P228R)) in the hinge region and at position 409 or 368 (e.g., K409R or L368E (EU numbering scheme)) in the CH3 region of human IgG2 (SEQ ID NO: 236). The FLT3/CD3 bispecific antibody also has the mutation from D to A at position 265 (EU numbering scheme).

Figure 1:
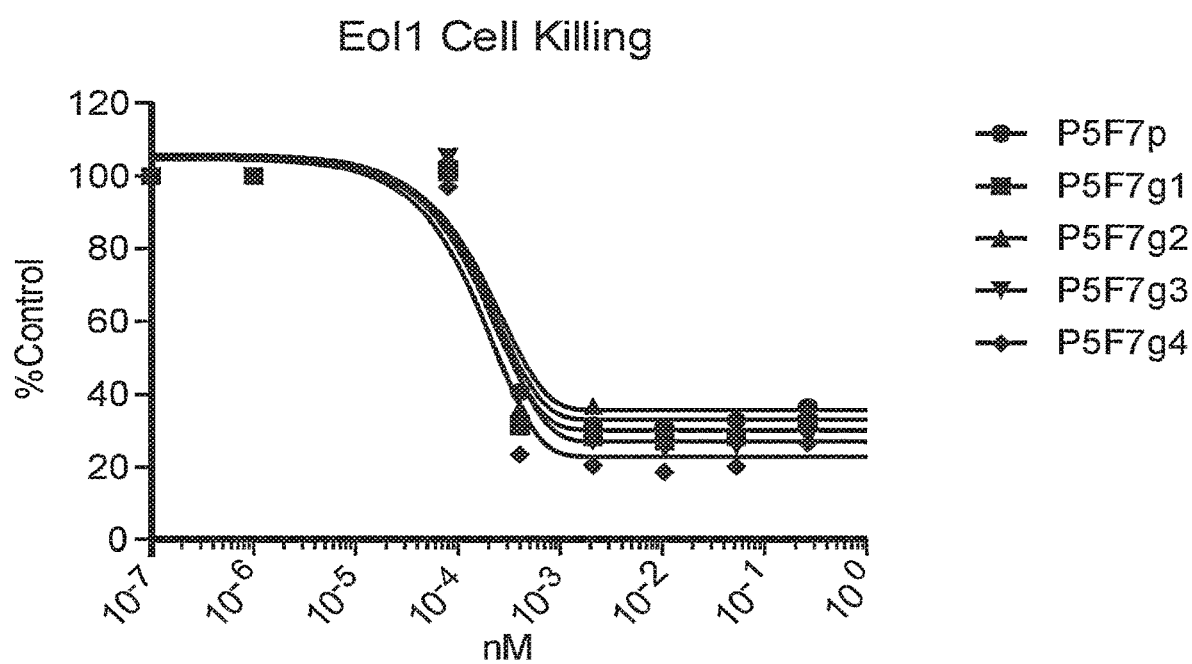
FIG. 1 shows that FLT3/CD3 bispecifics (FLT3 arm is P5F7g, P5F7g1, P5F7g2, P5F7g3, or P5F7g4) induce cytotoxicity in AML cell line Eol1.

CD3+ T cells from human PBMC were negatively selected using Pan T Cell Isolation kit, human (Miltenyi, San Diego CA). Target expressing (Eo11) cells and CD3+ T-cells were seeded on clear U-bottom plates at 20000 and 100000 cells/well respectively. Cells were treated with 8-fold serially diluted bispecific antibody. AML cell depletion was determined by flow-cytometry analysis 24 hours after treatment. Cell depletion was measured by contrast to control treated cells, in this case H2B4 only in FIG. 1. EC50 was calculated by Prism software. Cytotoxicity was observed in this Eo11 cell line as shown in FIG. 1.

Example 3: Flt3-CD3 Bispecific IgG Induces Tumor Ablation in AML Orthotopic Xenograft Model This example illustrates tumor regression and inhibition in an orthotopic Eo11 xenograft model.

In vivo efficacy study of Flt3 bispecifics was performed with Eo11, expressing luciferase and GFP, orthotopic model.

TABLE 6

| | | IgG format | | | | scFv format | | | |
|---|---|---|---|---|---|---|---|---|---|
| | | | | | huFlt3 | mFlt3 | | | |
| | domain | $k_a$ (1/Ms) | $k_d$ (1/s) | $t_{1/2}$ (min) | $K_D$ (nM) | $K_d$ (nM) | $k_a$ (1/Ms) | $k_d$ (1/s) | $t_{1/2}$ (min) | $K_D$ (nM) |
| P4F6 | 1 | 1.40E+05 | 3.50E−03 | 3.3 | 25 | 36.1 | 1.32E+05 | 1.99E−03 | 5.8 | 15.1 |
| P4C7 | 1 | 1.60E+05 | 1.20E−03 | 9.3 | 7.7 | 402.4 | 1.21E+05 | 1.64E−03 | 7 | 13.6 |
| P3A1 | 2 | 9.50E+04 | 6.00E−03 | 1.9 | 64 | — | 1.07E+05 | 1.67E−03 | 6.9 | 15.67 |
| P5A3 | 3 | 9.80E+04 | 1.00E−02 | 1.2 | 102 | 19.3 | 8.10E+04 | 1.75E−02 | 0.7 | 216 |
| P9B5 | 3 | 4.20E+04 | 4.70E−04 | 24.4 | 11 | 1.5 | 3.80E+04 | 6.87E−04 | 16.8 | 18.1 |
| P9F1 | 3 | 1.80E+05 | 2.30E−02 | 0.5 | 127 | — | 2.26E+05 | 2.86E−02 | 0.4 | 126.5 |
| P1B4 | 4 | 1.80E+05 | 5.80E−03 | 2 | 32 | — | 1.20E+05 | 3.27E−03 | 3.5 | 27.3 |
| P1B11 | 4 | 1.20E+05 | 5.50E−03 | 2.1 | 45 | — | 8.47E+04 | 2.57E−03 | 4.5 | 30.3 |
| P7H3 | 4 | 9.90E+05 | 1.80E−03 | 6.6 | 2 | 0.9 | 2.05E+05 | 1.87E−03 | 6.2 | 9.1 |
| P3E10 | 4 | 1.80E+05 | 1.90E−02 | 0.6 | 106 | — | 1.72E+05 | 1.12E−02 | 1 | 65.1 |
| P1A5 | 4 | 1.78E+06 | 3.47E−04 | 33 | 0.19 | — | 2.59E+05 | 2.92E−04 | 40 | 1.1 |
| P4A4 | 4 | 1.16E+06 | 4.69E−04 | 25 | 0.4 | — | | | | |
| P1G12 | 4 | 6.17E+05 | 2.92E−04 | 40 | 0.47 | 6.5 | | | | |
| P4E5 | 4 | 1.20E+06 | 1.51E−04 | 77 | 0.13 | 18.9 | | | | |
| P5A4 | 4 | 5.53E+05 | 1.01E−04 | 114 | 0.18 | — | | | | |
| P5F7 | 4 | 6.36E+05 | 1.52E−04 | 76 | 0.24 | — | 1.89E+05 | 1.97E−04 | 59 | 1 |
| P4H11 | 4 | 6.18E+04 | 1.44E−02 | 1 | 233 | — | 1.60E+05 | 9.33E−03 | 1 | 58.3 |
| P15F7 | 5 | 1.40E+05 | 5.50E−03 | 2.1 | 38 | — | | | | |
| P12B6 | 5 | 1.10E+05 | 9.00E−03 | 1.3 | 84 | — | | | | |
| P7D3 | 5 | 7.10E+04 | 5.20E−03 | 2.2 | 72 | — | | | | |
| P7A6 | 5 | 3.40E+04 | 3.70E−04 | 31 | 11 | — | | | | |
| P8B6 | 5 | 9.30E+04 | 2.30E−04 | 51 | 2.5 | — | | | | |
| P14G2 | 5 | 1.40E+05 | 1.10E−03 | 10.7 | 8 | — | 9.35E+04 | 3.05E−04 | 37.9 | 3.3 |
| P7F9 | 4 | 1.10E+05 | 1.30E−03 | 8.9 | 12 | 13.8 | 8.70E+04 | 2.41E−03 | 4.8 | 27.7 |

Figure 2:
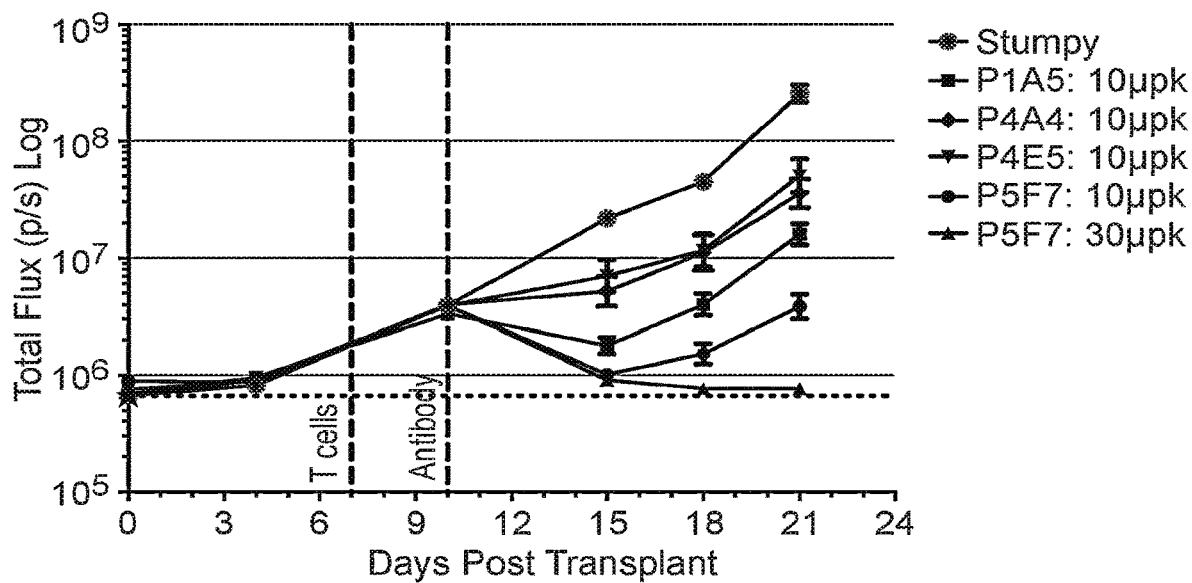
FIG. 2 shows that FLT3/CD3 bispecifics (FLT3 arm is P1F1, P4A4, P4E5, or P5F7) with FLT3 domain 4 binding epitopes are highly effective in inducing cytotoxicity in the Eol1 orthotopic model.
Figure 3:
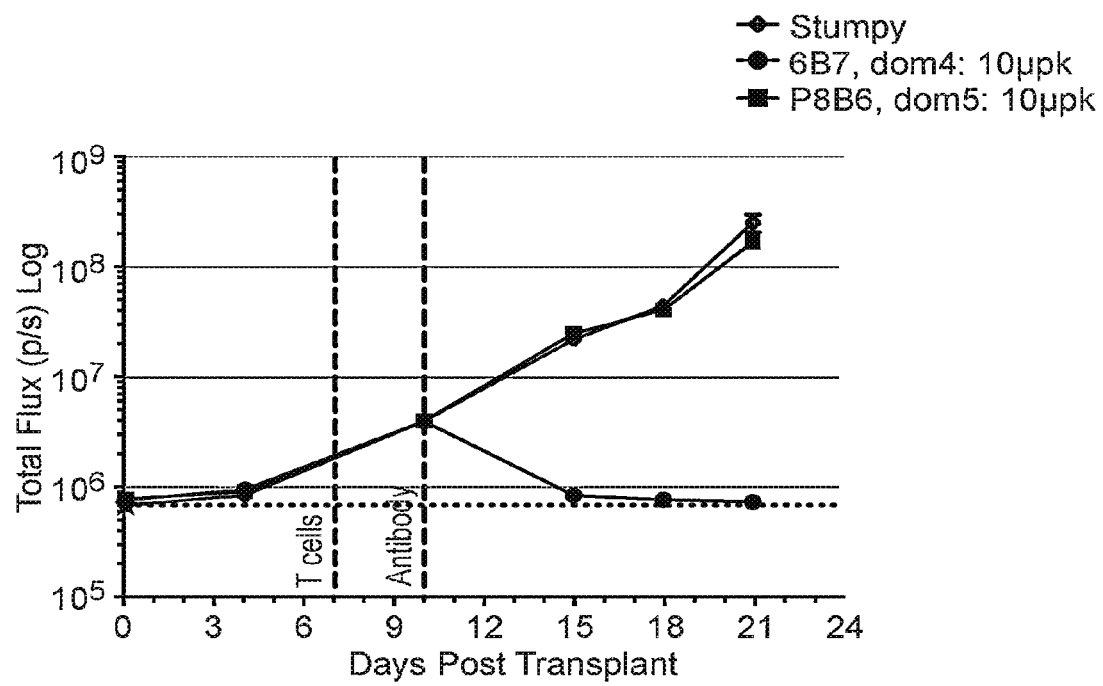
FIG. 3 shows that FLT3/CD3 bispecifics (FLT3 arm is 6B7 or P8B6) directed towards domain 4 of the FLT3 protein have improved tumor efficacy in an orthotopic xenograft in the presence of human T-cells.

Three hundred thousand Eol1 LucGFP cells were injected intravenously through the tail vein into 6-8 weeks old female Nod/Scid/IL2Rg$^{-/-}$ (NSG) animals. Intraperitoneal injection of D-luciferin (Regis Technologies, Morton Grove, IL) (200 uL per animal at 15 mg/mL), followed by anesthesia with isofluorane and subsequent whole body bioluminescence imaging (BLI) enabled monitoring of tumor burden. Bioluminescent signals emitted by the interaction between luciferase expressed by the tumor cells and luciferin were captured by imaging using an IVIS Spectrum CT (Perkin Elmer, MA) and quantified as total flux (photons/sec) using Living Image 4.4 (Caliper Life Sciences, Alameda, CA). When the total flux reached an average of 15E6 for all animals, the animals were injected through bolus tail vein with 20 million expanded T cells from PBMC. Briefly, pan-T cells purchased from Allcells (Alameda, CA) were activated with human T Cell Activation/Expansion Kit (Miltenyi, San Diego, CA). After three days, 20 ng/ml of IL2 (Miltenyi, Bergisch Gladbach, Germany) was added every two days until day 11. Cells were harvested, activation/expansion beads were magnetically removed, and cells were washed and resuspended in PBS. 2-days post T cell injection, mice were imaged as described above and animals were randomized into groups of seven mice: P1A5 10 μg/kg (ug/kg), P4A4 10 upk, P4E5 10 upk, P5F7 10 upk, P5F7 30 upk, and Stumpy (CD3 binding only bispecific control at 30 μg/kg). Three days post T-cell implant, a single dose of human anti-Flt3/CD3 (FLT3 antibody as listed above in one arm and the CD3 antibody (h2B4-VH-hnps VL-TK) in another arm) bispecific and negative (NNC) control bispecific antibody was administered via bolus tail vein injection. Animals were sacrificed when they exhibited hindlimb paralysis, an endpoint for AML orthotopic model. FIG. 2 shows that a single dose of human anti-Flt3/CD3 bispecific antibody resulted in tumor regression in a dose-dependent manner.

Example 4: Flt3-CD3 Bispecific IgGs Targeting Domain 4 Are More Potent Compared to Bispecifics Targeting Domain 5 in an AML Orthotopic Xenograft Model This example illustrates improved tumor activity of Flt3 domain 4 targeting antibodies as compared to domain 5 targeting antibodies.

Eol1 orthotopic xenograft model was performed as described in Example 3. In this instance, a domain 4 targeted bispecific 6B7 or a domain 5 targeted bispecific P8B6 was dosed at a single dose of 10 upk. Stumpy represents CD3 binding only control bispecific antibody. At the dose tested, P8B6 had no anti-tumor activity, whereas 6B7 was tumor ablative.

Example 5: EC50 Values for the Flt3 Bispecific are Significantly Reduced in the Presence of IL15 in a Long Term In Vitro Killing Assay This example illustrates the in vitro cytotoxicity of the Anti-Flt3/CD3 P5F7 Bispecific antibody in Flt3 Positive Cells, in combination with IL-15.

Previously frozen human Pan T lymphocytes were thawed and recovered in RPMI-1640 medium supplemented with 10% serum (Hyclone), 1% Pen Strep (Corning) and 15 units per mL of human IL-2 (eBioscience) for one day. Human T lymphocytes recovered for 1 day were collected and resuspended at $1\times10^6$ cells/mL in complete RPMI medium. Flt3-expressing EOL1 cells were seeded at 50,000 cells in 100 ul in a 96 well U-bottom plate. Fifty thousand (50,000) viable human CD3+ lymphocytes were added to the plated tumor cells in 25 μL of media per well. 5-point 5-fold serial dilutions of the Flt3/CD3 P5F7 bispecific antibody were prepared (dose range $1\times10^{-11}$ nM to $8\times10^{-14}$ nM final concentration). The cytotoxicity assay was initiated by adding diluted bispecific antibody to the plates and incubating at 37° C. for 2 days, 5 days or 7 days. To test the effect of IL15 on the antitumor efficacy of Flt3/CD3 bispecific antibody-redirected T cells, cell cultures received either 10 ng/ml IL15 or vehicle control. AML cell depletion was determined by luciferase analysis at respective time points. EC50 values were then determined by non-linear regression plot of percent specific cytotoxicity versus Log 10 concentration of Flt3/CD3 P5F7 bispecific using GraphPad Prism 7.0 software (GraphPad Software). FIG. 4A and FIG. 4B illustrate the improved anti-tumor activity of the Flt3/CD3 bispecific in the absence or presence of IL15 in a long term killing assay, respectively.

Example 6: Autologous T Cells Present in Bone Marrow Aspirates from AML Patients are Effective in Killing AML Blasts in the Presence of Flt3/CD3 P5F7 Bispecific This example illustrates that the anti-Flt3/CD3 P5F7 Bispecific antibody effectively redirects autologous T cells to eliminate AML blasts ex vivo.

To determine the cytotoxic activity using patient T cells and AML cells, fresh bone marrow aspirates were purchased from the Fred Hutchinson Cancer Research Center (Seattle, WA). The number of target cells (AML blasts) and effector cells (T cells) cell were determined by staining each sample with PerCP-cy5.5 anti-human CD3(BioLegend, San Diego, CA), BV 510 anti-human CD8 Antibody (BioLegend, San Diego, CA), BUV650 anti-human CD4 (BioLegend, San Diego, CA), PE-Texas Red anti-human CD33(BioLegend, San Diego, CA), APC anti-human Flt3 (BD Biosciences, San Jose, CA). Two hundred and fifty thousand (250,000) total bone marrow cells from each patient were plated on 24-well plates in 1 ml of media, and cultured at 37° C. under 5% $CO_2$ atmosphere. The P5F7 Flt3/CD3 bispecific antibody was diluted to 10 nM in complete RPMI medium and 5-point 10-fold serial dilutions were prepared (dose range 10 nM to 0.01 nM). The cytotoxicity assay was initiated by adding diluted bispecific antibody to the plates and incubating the cells at 37° C. for 4 days.

After 4 days of incubation, viability of the AML patient cells, T cell proliferation and activation were assessed by counting the number of CD33+ CD45dim AML blasts, the number of CD4+CD8+ cells, and the percentage of CD25+ CD4+ or CD25+ CD8+ cells, respectively, on a LSRII flow cytometry instrument using FACS Diva software (BD Biosciences). The results demonstrate effective killing of primary AML cells induced by increasing concentrations of FLT3/CD3 bispecific (P5F7) in the presence of autologous T cells (see FIGS. 5A, 5B, 5C, 5D, 5E, and 5F).

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

It is claimed:

1. A nucleic acid encoding an antibody, which specifically binds to Fms-like tyrosine kinase 3 (FLT3), wherein the antibody comprises:

(a) a heavy chain variable (VH) region comprising: a VH CDR1 comprising the sequence shown in SEQ ID NO: 37, 38 or 39; a VH CDR2 comprising the sequence shown in SEQ ID NO: 40 or 41; and a VH CDR3 comprising the sequence shown in SEQ ID NO: 42; and a light chain variable (VL) region comprising a VL CDR1 comprising the sequence shown in SEQ ID NO: 144; a VL CDR2 comprising the sequence shown in SEQ ID NO: 145; and a VL CDR3 comprising the sequence shown in SEQ ID NO: 146;

(b) a heavy chain variable (VH) region comprising: a VH CDR1 comprising the sequence shown in SEQ ID NO: 43, 44, or 45; a VH CDR2 comprising the sequence shown in SEQ ID NO: 46 or 47; and a VH CDR3 comprising the sequence shown in SEQ ID NO: 48; and a light chain variable (VL) region comprising a VL CDR1 comprising the sequence shown in SEQ ID NO: 147; a VL CDR2 comprising the sequence shown in SEQ ID NO: 148; and a VL CDR3 comprising the sequence shown in SEQ ID NO: 149;

(c) a heavy chain variable (VH) region comprising: a VH CDR1 comprising the sequence shown in SEQ ID NO: 54, 55 or 56; a VH CDR2 comprising the sequence shown in SEQ ID NO: 57 or 58; and a VH CDR3 comprising the sequence shown in SEQ ID NO: 59; and a light chain variable (VL) region comprising a VL CDR1 comprising the sequence shown in SEQ ID NO: 153; a VL CDR2 comprising the sequence shown in SEQ ID NO: 154; and a VL CDR3 comprising the sequence shown in SEQ ID NO: 155;

(d) a heavy chain variable (VH) region comprising: a VH CDR1 comprising the sequence shown in SEQ ID NO: 66, 67 or 68; a VH CDR2 comprising the sequence shown in SEQ ID NO: 69 or 70; and a VH CDR3 comprising the sequence shown in SEQ ID NO: 71; and a light chain variable (VL) region comprising a VL CDR1 comprising the sequence shown in SEQ ID NO: 159; a VL CDR2 comprising the sequence shown in SEQ ID NO: 160; and a VL CDR3 comprising the sequence shown in SEQ ID NO: 161;

(e) a heavy chain variable (VH) region comprising: a VH CDR1 comprising the sequence shown in SEQ ID NO: 72, 73 or 74; a VH CDR2 comprising the sequence shown in SEQ ID NO: 75 or 76; and a VH CDR3 comprising the sequence shown in SEQ ID NO: 77; and a light chain variable (VL) region comprising a VL CDR1 comprising the sequence shown in SEQ ID NO: 162; a VL CDR2 comprising the sequence shown in SEQ ID NO: 163; and a VL CDR3 comprising the sequence shown in SEQ ID NO: 164;

(f) a heavy chain variable (VH) region comprising: a VH CDR1 comprising the sequence shown in SEQ ID NO: 78, 79 or 80; a VH CDR2 comprising the sequence shown in SEQ ID NO: 81 or 82; and a VH CDR3 comprising the sequence shown in SEQ ID NO: 83; and a light chain variable (VL) region comprising a VL CDR1 comprising the sequence shown in SEQ ID NO: 165; a VL CDR2 comprising the sequence shown in SEQ ID NO: 166; and a VL CDR3 comprising the sequence shown in SEQ ID NO: 167;

(g) a heavy chain variable (VH) region comprising: a VH CDR1 comprising the sequence shown in SEQ ID NO: 96, 97 or 98; a VH CDR2 comprising the sequence shown in SEQ ID NO: 99 or 100; and a VH CDR3 comprising the sequence shown in SEQ ID NO: 101; and a light chain variable (VL) region comprising a VL CDR1 comprising the sequence shown in SEQ ID NO: 174; a VL CDR2 comprising the sequence shown in SEQ ID NO: 175; and a VL CDR3 comprising the sequence shown in SEQ ID NO: 176;

(h) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 177; a VL CDR2 comprising the sequence shown in SEQ ID NO: 178; and a VL CDR3 comprising the sequence shown in SEQ ID NO: 179;

(i) a heavy chain variable (VH) region comprising: a VH CDR1 comprising the sequence shown in SEQ ID NO: 114, 115 or 116; a VH CDR2 comprising the sequence shown in SEQ ID NO: 117 or 118; and a VH CDR3 comprising the sequence shown in SEQ ID NO: 119; and a light chain variable (VL) region comprising a VL CDR1 comprising the sequence shown in SEQ ID NO: 183; a VL CDR2 comprising the sequence shown in SEQ ID NO: 184; and a VL CDR3 comprising the sequence shown in SEQ ID NO: 185;

(j) (o) a heavy chain variable (VH) region comprising: a VH CDR1 comprising the sequence shown in SEQ ID NO: 120, 121 or 122; a VH CDR2 comprising the sequence shown in SEQ ID NO: 123 or 124; and a VH CDR3 comprising the sequence shown in SEQ ID NO: 125; and a light chain variable (VL) region comprising a VL CDR1 comprising the sequence shown in SEQ ID NO: 186; a VL CDR2 comprising the sequence shown in SEQ ID NO: 187; and a VL CDR3 comprising the sequence shown in SEQ ID NO: 188;

(k) a heavy chain variable (VH) region comprising: a VH CDR1 comprising the sequence shown in SEQ ID NO: 126, 127 or 128; a VH CDR2 comprising the sequence shown in SEQ ID NO: 129 or 130; and a VH CDR3 comprising the sequence shown in SEQ ID NO: 131; and a light chain variable (VL) region comprising a VL CDR1 comprising the sequence shown in SEQ ID NO: 189; a VL CDR2 comprising the sequence shown in SEQ ID NO: 190; and a VL CDR3 comprising the sequence shown in SEQ ID NO: 191;

(l) a heavy chain variable (VH) region comprising: a VH CDR1 comprising the sequence shown in SEQ ID NO: 132, 133 or 134; a VH CDR2 comprising the sequence shown in SEQ ID NO: 135 or 136; and a VH CDR3 comprising the sequence shown in SEQ ID NO: 137; and a light chain variable (VL) region comprising a VL CDR1 comprising the sequence shown in SEQ ID NO: 192; a VL CDR2 comprising the sequence shown in SEQ ID NO: 193; and a VL CDR3 comprising the sequence shown in SEQ ID NO: 194;

(m) a heavy chain variable (VH) region comprising: a VH CDR1 comprising the sequence shown in SEQ ID NO: 138, 139 or 140; a VH CDR2 comprising the sequence shown in SEQ ID NO: 141 or 142; and a VH CDR3 comprising the sequence shown in SEQ ID NO: 143; and a light chain variable (VL) region comprising a VL CDR1 comprising the sequence shown in SEQ ID NO: 195; a VL CDR2 comprising the sequence shown in SEQ ID NO: 196; and a VL CDR3 comprising the sequence shown in SEQ ID NO: 197;

(n) a heavy chain variable (VH) region comprising: a VH CDR1 comprising the sequence shown in SEQ ID NO: 126, 127 or 128; a VH CDR2 comprising the sequence shown in SEQ ID NO: 129 or 130; and a VH CDR3 comprising the sequence shown in SEQ ID NO: 245; and a light chain variable (VL) region comprising a VL CDR1 comprising the sequence shown in SEQ ID NO: 189; a VL CDR2 comprising the sequence shown in SEQ ID NO: 190; and a VL CDR3 comprising the sequence shown in SEQ ID NO: 256;

(o) a heavy chain variable (VH) region comprising: a VH CDR1 comprising the sequence shown in SEQ ID NO: 247, 127 or 246; a VH CDR2 comprising the sequence shown in SEQ ID NO: 248 or 249; and a VH CDR3 comprising the sequence shown in SEQ ID NO: 250; and a light chain variable (VL) region comprising a VL CDR1 comprising the sequence shown in SEQ ID NO: 257; a VL CDR2 comprising the sequence shown in SEQ ID NO: 190; and a VL CDR3 comprising the sequence shown in SEQ ID NO: 258;

(p) a heavy chain variable (VH) region comprising: a VH CDR1 comprising the sequence shown in SEQ ID NO: 72, 73 or 74; a VH CDR2 comprising the sequence shown in SEQ ID NO: 100 or 251; and a VH CDR3 comprising the sequence shown in SEQ ID NO: 77; and a light chain variable (VL) region comprising a VL CDR1 comprising the sequence shown in SEQ ID NO: 174; a VL CDR2 comprising the sequence shown in SEQ ID NO: 175; and a VL CDR3 comprising the sequence shown in SEQ ID NO: 176;

(q) a heavy chain variable (VH) region comprising: a VH CDR1 comprising the sequence shown in SEQ ID NO: 49, 44 or 50; a VH CDR2 comprising the sequence shown in SEQ ID NO: 253 or 252; and a VH CDR3 comprising the sequence shown in SEQ ID NO: 254; and a light chain variable (VL) region comprising a VL CDR1 comprising the sequence shown in SEQ ID NO: 177; a VL CDR2 comprising the sequence shown in SEQ ID NO: 259; and a VL CDR3 comprising the sequence shown in SEQ ID NO: 260;

(r) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 177; a VL CDR2 comprising the sequence shown in SEQ ID NO: 178; and a VL CDR3 comprising the sequence shown in SEQ ID NO: 179;

(s) a heavy chain variable (VH) region comprising: a VH CDR1 comprising the sequence shown in SEQ ID NO: 102, 103 or 104; a VH CDR2 comprising the sequence shown in SEQ ID NO: 255 or 106; and a VH CDR3 comprising the sequence shown in SEQ ID NO: 107; and a light chain variable (VL) region comprising a VL CDR1 comprising the sequence shown in SEQ ID NO: 177; a VL CDR2 comprising the sequence shown in SEQ ID NO: 178; and a VL CDR3 comprising the sequence shown in SEQ ID NO: 179;

(t) a heavy chain variable (VH) region comprising: a VH CDR1 comprising the sequence shown in SEQ ID NO: 138, 139 or 140; a VH CDR2 comprising the sequence shown in SEQ ID NO: 255 or 106; and a VH CDR3 comprising the sequence shown in SEQ ID NO: 107; and a light chain variable (VL) region comprising a VL CDR1 comprising the sequence shown in SEQ ID NO: 275; a VL CDR2 comprising the sequence shown in SEQ ID NO: 259; and a VL CDR3 comprising the sequence shown in SEQ ID NO: 264;

(u) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 261; a VL CDR2 comprising the sequence shown in SEQ ID NO: 259; and a VL CDR3 comprising the sequence shown in SEQ ID NO: 262;

(v) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 263; a VL CDR2 comprising the sequence shown in SEQ ID NO: 259; and a VL CDR3 comprising the sequence shown in SEQ ID NO: 264;

(w) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 265; a VL CDR2 comprising the sequence shown in SEQ ID NO: 266; and a VL CDR3 comprising the sequence shown in SEQ ID NO: 267;

(x) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 268; a VL CDR2 comprising the sequence shown in SEQ ID NO: 266; and a VL CDR3 comprising the sequence shown in SEQ ID NO: 269;

(y) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 270; a VL CDR2 comprising the sequence shown in SEQ ID NO: 271; and a VL CDR3 comprising the sequence shown in SEQ ID NO: 272;

(z) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 273; a VL CDR2 comprising the sequence shown in SEQ ID NO: 266; and a VL CDR3 comprising the sequence shown in SEQ ID NO: 274; or (aa) a heavy chain variable (VH) region comprising: a VH CDR1 comprising the sequence shown in SEQ ID NO: 102, 103 or 104; a VH CDR2 comprising the sequence shown in SEQ ID NO: 255 or 106; and a VH CDR3 comprising the sequence shown in SEQ ID NO: 107; and a light chain variable (VL) region comprising a VL CDR1 comprising the sequence shown in SEQ ID NO: 275; a VL CDR2 comprising the sequence shown in SEQ ID NO: 259; and a VL CDR3 comprising the sequence shown in SEQ ID NO: 264.

2. A nucleic acid encoding an antibody, which specifically binds to Fms-like tyrosine kinase 3 (FLT3), wherein the antibody comprises:

(a) a VH region comprising the VH sequence shown in SEQ ID NO: 2, and a VL region comprising the VL sequence shown in SEQ ID NO: 1;

(b) a VH region comprising the VH sequence shown in SEQ ID NO: 4, and a VL region comprising the VL sequence shown in SEQ ID NO: 3;

(c) a VH region comprising the VH sequence shown in SEQ ID NO: 8, and a VL region comprising the VL sequence shown in SEQ ID NO: 7;

(d) a VH region comprising the VH sequence shown in SEQ ID NO: 12, and a VL region comprising the VL sequence shown in SEQ ID NO: 11;

(e) a VH region comprising the VH sequence shown in SEQ ID NO: 14, and a VL region comprising the VL sequence shown in SEQ ID NO: 13;

(f) a VH region comprising the VH sequence shown in SEQ ID NO: 16, and a VL region comprising the VL sequence shown in SEQ ID NO: 15;

(g) a VH region comprising the VH sequence shown in SEQ ID NO: 22, and a VL region comprising the VL sequence shown in SEQ ID NO: 21;

(h) a VH region comprising the VH sequence shown in SEQ ID NO: 24, and a VL region comprising the VL sequence shown in SEQ ID NO: 23;

(i) a VH region comprising the VH sequence shown in SEQ ID NO: 28, and a VL region comprising the VL sequence shown in SEQ ID NO: 27;

(j) a VH region comprising the VH sequence shown in SEQ ID NO: 30, and a VL region comprising the VL sequence shown in SEQ ID NO: 29;

(k) a VH region comprising the VH sequence shown in SEQ ID NO: 32, and a VL region comprising the VL sequence shown in SEQ ID NO: 31;

(l) a VH region comprising the VH sequence shown in SEQ ID NO: 34, and a VL region comprising the VL sequence shown in SEQ ID NO: 33;

(m) a VH region comprising the VH sequence shown in SEQ ID NO: 36, and a VL region comprising the VL sequence shown in SEQ ID NO: 35;

(n) a VH region comprising the VH sequence shown in SEQ ID NO: 205, and a VL region comprising the VL sequence shown in SEQ ID NO: 204;

(o) a VH region comprising the VH sequence shown in SEQ ID NO: 207, and a VL region comprising the VL sequence shown in SEQ ID NO: 206;

(p) a VH region comprising the VH sequence shown in SEQ ID NO: 209, and a VL region comprising the VL sequence shown in SEQ ID NO: 208;

(q) a VH region comprising the VH sequence shown in SEQ ID NO: 211, and a VL region comprising the VL sequence shown in SEQ ID NO: 210;

(r) a VH region comprising the VH sequence shown in SEQ ID NO: 213, and a VL region comprising the VL sequence shown in SEQ ID NO: 212;

(s) VH region comprising the VH sequence shown in SEQ ID NO: 215, and a VL region comprising the VL sequence shown in SEQ ID NO: 214;
(t) a VH region comprising the VH sequence shown in SEQ ID NO: 217, and a VL region comprising the VL sequence shown in SEQ ID NO: 216;
(u) a VH region comprising the VH sequence shown in SEQ ID NO: 219, and a VL region comprising the VL sequence shown in SEQ ID NO: 218;
(v) a VH region comprising the VH sequence shown in SEQ ID NO: 221, and a VL region comprising the VL sequence shown in SEQ ID NO: 220;
(w) a VH region comprising the VH sequence shown in SEQ ID NO: 223, and a VL region comprising the VL sequence shown in SEQ ID NO: 222;
(x) a VH region comprising the VH sequence shown in SEQ ID NO: 225, and a VL region comprising the VL sequence shown in SEQ ID NO: 224;
(y) a VH region comprising the VH sequence shown in SEQ ID NO: 227, and a VL region comprising the VL sequence shown in SEQ ID NO: 226;
(z) a VH region comprising the VH sequence shown in SEQ ID NO: 229, and a VL region comprising the VL sequence shown in SEQ ID NO: 228;
(aa) a VH region comprising the VH sequence shown in SEQ ID NO: 231, and a VL region comprising the VL sequence shown in SEQ ID NO: 230; or
(bb) a VH region comprising the VH sequence shown in SEQ ID NO: 233, and a VL region comprising the VL sequence shown in SEQ ID NO: 232.

3. A vector comprising the nucleic acid of claim 1.
4. A vector comprising the nucleic acid of claim 2.
5. A cell comprising the vector of claim 3.
6. A cell comprising the vector of claim 4.
7. A method of treating a subject in need thereof comprising:
   (a) providing the antibody encoded by the nucleic acid of claim 1; and
   (b) administering said antibody to said subject.
8. A bispecific antibody wherein the bispecific antibody is a full-length antibody, comprising a first antibody variable domain of the bispecific antibody specifically binding to a target antigen, and comprising a second antibody variable domain of the bispecific antibody capable of recruiting the activity of a human immune effector cell by specifically binding to an effector antigen located on the human immune effector cell, wherein the first antibody variable domain comprises:
   (a) a heavy chain variable (VH) region comprising: a VH CDR1 comprising the sequence shown in SEQ ID NO: 37, 38 or 39; a VH CDR2 comprising the sequence shown in SEQ ID NO: 40 or 41; and a VH CDR3 comprising the sequence shown in SEQ ID NO: 42; and a light chain variable (VL) region comprising a VL CDR1 comprising the sequence shown in SEQ ID NO: 144; a VL CDR2 comprising the sequence shown in SEQ ID NO: 145; and a VL CDR3 comprising the sequence shown in SEQ ID NO: 146;
   (b) a heavy chain variable (VH) region comprising: a VH CDR1 comprising the sequence shown in SEQ ID NO: 43, 44, or 45; a VH CDR2 comprising the sequence shown in SEQ ID NO: 46 or 47; and a VH CDR3 comprising the sequence shown in SEQ ID NO: 48; and a light chain variable (VL) region comprising a VL CDR1 comprising the sequence shown in SEQ ID NO: 147; a VL CDR2 comprising the sequence shown in SEQ ID NO: 148; and a VL CDR3 comprising the sequence shown in SEQ ID NO: 149;
   (c) a heavy chain variable (VH) region comprising: a VH CDR1 comprising the sequence shown in SEQ ID NO: 54, 55 or 56; a VH CDR2 comprising the sequence shown in SEQ ID NO: 57 or 58; and a VH CDR3 comprising the sequence shown in SEQ ID NO: 59; and a light chain variable (VL) region comprising a VL CDR1 comprising the sequence shown in SEQ ID NO: 153; a VL CDR2 comprising the sequence shown in SEQ ID NO: 154; and a VL CDR3 comprising the sequence shown in SEQ ID NO: 155;
   (d) a heavy chain variable (VH) region comprising: a VH CDR1 comprising the sequence shown in SEQ ID NO: 66, 67 or 68; a VH CDR2 comprising the sequence shown in SEQ ID NO: 69 or 70; and a VH CDR3 comprising the sequence shown in SEQ ID NO: 71; and a light chain variable (VL) region comprising a VL CDR1 comprising the sequence shown in SEQ ID NO: 159; a VL CDR2 comprising the sequence shown in SEQ ID NO: 160; and a VL CDR3 comprising the sequence shown in SEQ ID NO: 161;
   (e) a heavy chain variable (VH) region comprising: a VH CDR1 comprising the sequence shown in SEQ ID NO: 72, 73 or 74; a VH CDR2 comprising the sequence shown in SEQ ID NO: 75 or 76; and a VH CDR3 comprising the sequence shown in SEQ ID NO: 77; and a light chain variable (VL) region comprising a VL CDR1 comprising the sequence shown in SEQ ID NO: 162; a VL CDR2 comprising the sequence shown in SEQ ID NO: 163; and a VL CDR3 comprising the sequence shown in SEQ ID NO: 164;
   (f) a heavy chain variable (VH) region comprising: a VH CDR1 comprising the sequence shown in SEQ ID NO: 78, 79 or 80; a VH CDR2 comprising the sequence shown in SEQ ID NO: 81 or 82; and a VH CDR3 comprising the sequence shown in SEQ ID NO: 83; and a light chain variable (VL) region comprising a VL CDR1 comprising the sequence shown in SEQ ID NO: 165; a VL CDR2 comprising the sequence shown in SEQ ID NO: 166; and a VL CDR3 comprising the sequence shown in SEQ ID NO: 167;
   (g) a heavy chain variable (VH) region comprising: a VH CDR1 comprising the sequence shown in SEQ ID NO: 96, 97 or 98; a VH CDR2 comprising the sequence shown in SEQ ID NO: 99 or 100; and a VH CDR3 comprising the sequence shown in SEQ ID NO: 101; and a light chain variable (VL) region comprising a VL CDR1 comprising the sequence shown in SEQ ID NO: 174; a VL CDR2 comprising the sequence shown in SEQ ID NO: 175; and a VL CDR3 comprising the sequence shown in SEQ ID NO: 176;
   (h) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 177; a VL CDR2 comprising the sequence shown in SEQ ID NO: 178; and a VL CDR3 comprising the sequence shown in SEQ ID NO: 179;
   (i) a heavy chain variable (VH) region comprising: a VH CDR1 comprising the sequence shown in SEQ ID NO: 114, 115 or 116; a VH CDR2 comprising the sequence shown in SEQ ID NO: 117 or 118; and a VH CDR3 comprising the sequence shown in SEQ ID NO: 119;

and a light chain variable (VL) region comprising a VL CDR1 comprising the sequence shown in SEQ ID NO: 183; a VL CDR2 comprising the sequence shown in SEQ ID NO: 184; and a VL CDR3 comprising the sequence shown in SEQ ID NO: 185;

(j) (o) a heavy chain variable (VH) region comprising: a VH CDR1 comprising the sequence shown in SEQ ID NO: 120, 121 or 122; a VH CDR2 comprising the sequence shown in SEQ ID NO: 123 or 124; and a VH CDR3 comprising the sequence shown in SEQ ID NO: 125; and a light chain variable (VL) region comprising a VL CDR1 comprising the sequence shown in SEQ ID NO: 186; a VL CDR2 comprising the sequence shown in SEQ ID NO: 187; and a VL CDR3 comprising the sequence shown in SEQ ID NO: 188;

(k) a heavy chain variable (VH) region comprising: a VH CDR1 comprising the sequence shown in SEQ ID NO: 126, 127 or 128; a VH CDR2 comprising the sequence shown in SEQ ID NO: 129 or 130; and a VH CDR3 comprising the sequence shown in SEQ ID NO: 131; and a light chain variable (VL) region comprising a VL CDR1 comprising the sequence shown in SEQ ID NO: 189; a VL CDR2 comprising the sequence shown in SEQ ID NO: 190; and a VL CDR3 comprising the sequence shown in SEQ ID NO: 191;

(l) a heavy chain variable (VH) region comprising: a VH CDR1 comprising the sequence shown in SEQ ID NO: 132, 133 or 134; a VH CDR2 comprising the sequence shown in SEQ ID NO: 135 or 136; and a VH CDR3 comprising the sequence shown in SEQ ID NO: 137; and a light chain variable (VL) region comprising a VL CDR1 comprising the sequence shown in SEQ ID NO: 192; a VL CDR2 comprising the sequence shown in SEQ ID NO: 193; and a VL CDR3 comprising the sequence shown in SEQ ID NO: 194;

(m) a heavy chain variable (VH) region comprising: a VH CDR1 comprising the sequence shown in SEQ ID NO: 138, 139 or 140; a VH CDR2 comprising the sequence shown in SEQ ID NO: 141 or 142; and a VH CDR3 comprising the sequence shown in SEQ ID NO: 143; and a light chain variable (VL) region comprising a VL CDR1 comprising the sequence shown in SEQ ID NO: 195; a VL CDR2 comprising the sequence shown in SEQ ID NO: 196; and a VL CDR3 comprising the sequence shown in SEQ ID NO: 197;

(n) a heavy chain variable (VH) region comprising: a VH CDR1 comprising the sequence shown in SEQ ID NO: 126, 127 or 128; a VH CDR2 comprising the sequence shown in SEQ ID NO: 129 or 130; and a VH CDR3 comprising the sequence shown in SEQ ID NO: 245; and a light chain variable (VL) region comprising a VL CDR1 comprising the sequence shown in SEQ ID NO: 189; a VL CDR2 comprising the sequence shown in SEQ ID NO: 190; and a VL CDR3 comprising the sequence shown in SEQ ID NO: 256;

(o) a heavy chain variable (VH) region comprising: a VH CDR1 comprising the sequence shown in SEQ ID NO: 247, 127 or 246; a VH CDR2 comprising the sequence shown in SEQ ID NO: 248 or 249; and a VH CDR3 comprising the sequence shown in SEQ ID NO: 250; and a light chain variable (VL) region comprising a VL CDR1 comprising the sequence shown in SEQ ID NO: 257; a VL CDR2 comprising the sequence shown in SEQ ID NO: 190; and a VL CDR3 comprising the sequence shown in SEQ ID NO: 258;

(p) a heavy chain variable (VH) region comprising: a VH CDR1 comprising the sequence shown in SEQ ID NO: 72, 73 or 74; a VH CDR2 comprising the sequence shown in SEQ ID NO: 100 or 251; and a VH CDR3 comprising the sequence shown in SEQ ID NO: 77; and a light chain variable (VL) region comprising a VL CDR1 comprising the sequence shown in SEQ ID NO: 174; a VL CDR2 comprising the sequence shown in SEQ ID NO: 175; and a VL CDR3 comprising the sequence shown in SEQ ID NO: 176;

(q) a heavy chain variable (VH) region comprising: a VH CDR1 comprising the sequence shown in SEQ ID NO: 49, 44 or 50; a VH CDR2 comprising the sequence shown in SEQ ID NO: 253 or 252; and a VH CDR3 comprising the sequence shown in SEQ ID NO: 254; and a light chain variable (VL) region comprising a VL CDR1 comprising the sequence shown in SEQ ID NO: 177; a VL CDR2 comprising the sequence shown in SEQ ID NO: 259; and a VL CDR3 comprising the sequence shown in SEQ ID NO: 260;

(r) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 177; a VL CDR2 comprising the sequence shown in SEQ ID NO: 178; and a VL CDR3 comprising the sequence shown in SEQ ID NO: 179;

(s) a heavy chain variable (VH) region comprising: a VH CDR1 comprising the sequence shown in SEQ ID NO: 102, 103 or 104; a VH CDR2 comprising the sequence shown in SEQ ID NO: 255 or 106; and a VH CDR3 comprising the sequence shown in SEQ ID NO: 107; and a light chain variable (VL) region comprising a VL CDR1 comprising the sequence shown in SEQ ID NO: 177; a VL CDR2 comprising the sequence shown in SEQ ID NO: 178; and a VL CDR3 comprising the sequence shown in SEQ ID NO: 179;

(t) a heavy chain variable (VH) region comprising: a VH CDR1 comprising the sequence shown in SEQ ID NO: 138, 139 or 140; a VH CDR2 comprising the sequence shown in SEQ ID NO: 255 or 106; and a VH CDR3 comprising the sequence shown in SEQ ID NO: 107; and a light chain variable (VL) region comprising a VL CDR1 comprising the sequence shown in SEQ ID NO: 275; a VL CDR2 comprising the sequence shown in SEQ ID NO: 259; and a VL CDR3 comprising the sequence shown in SEQ ID NO: 264;

(u) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 261; a VL CDR2 comprising the sequence shown in SEQ ID NO: 259; and a VL CDR3 comprising the sequence shown in SEQ ID NO: 262;

(v) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 263; a VL CDR2 comprising the sequence shown in SEQ ID NO: 259; and a VL CDR3 comprising the sequence shown in SEQ ID NO: 264;

(w) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 265; a VL CDR2 comprising the sequence shown in SEQ ID NO: 266; and a VL CDR3 comprising the sequence shown in SEQ ID NO: 267;

(x) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 268; a VL CDR2 comprising the sequence shown in SEQ ID NO: 266; and a VL CDR3 comprising the sequence shown in SEQ ID NO: 269;

(y) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 270; a VL CDR2 comprising the sequence shown in SEQ ID NO: 271; and a VL CDR3 comprising the sequence shown in SEQ ID NO: 272;

(z) a heavy chain variable (VH) region comprising: a VH CDR1 comprising the sequence shown in SEQ ID NO: 102, 103 or 104; a VH CDR2 comprising the sequence shown in SEQ ID NO: 105 or 106; and a VH CDR3 comprising the sequence shown in SEQ ID NO: 107; and a light chain variable (VL) region comprising a VL CDR1 comprising the sequence shown in SEQ ID NO: 273; a VL CDR2 comprising the sequence shown in SEQ ID NO: 266; and a VL CDR3 comprising the sequence shown in SEQ ID NO: 274; or (aa) a heavy chain variable (VH) region comprising: a VH CDR1 comprising the sequence shown in SEQ ID NO: 102, 103 or 104; a VH CDR2 comprising the sequence shown in SEQ ID NO: 255 or 106; and a VH CDR3 comprising the sequence shown in SEQ ID NO: 107; and a light chain variable (VL) region comprising a VL CDR1 comprising the sequence shown in SEQ ID NO: 275; a VL CDR2 comprising the sequence shown in SEQ ID NO: 259; and a VL CDR3 comprising the sequence shown in SEQ ID NO: 264.

* * * * *